US011525163B2

(12) United States Patent
Kinde et al.

(10) Patent No.: US 11,525,163 B2
(45) Date of Patent: Dec. 13, 2022

(54) PAPANICOLAOU TEST FOR OVARIAN AND ENDOMETRIAL CANCERS

(71) Applicant: THE JOHNS HOPKINS UNIVERSITY, Baltimore, MD (US)

(72) Inventors: Isaac Kinde, Beaumont, CA (US); Kenneth W. Kinzler, Baltimore, MD (US); Bert Vogelstein, Baltimore, MD (US); Nickolas Papadopoulos, Towson, MD (US); Luis Diaz, Ellicott City, MD (US); Chetan Bettegowda, Perry Hall, MD (US); Yuxuan Wang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 90 days.

(21) Appl. No.: 14/439,041

(22) PCT Filed: Oct. 17, 2013

(86) PCT No.: PCT/US2013/065342

§ 371 (c)(1),
(2) Date: Apr. 28, 2015

(87) PCT Pub. No.: WO2014/070462

PCT Pub. Date: May 8, 2014

(65) Prior Publication Data

US 2015/0292027 A1 Oct. 15, 2015

Related U.S. Application Data

(60) Provisional application No. 61/719,942, filed on Oct. 29, 2012.

(51) Int. Cl.

| | |
|---|---|
| ***C12Q 1/68*** | (2018.01) |
| ***C12Q 1/6886*** | (2018.01) |
| ***G01N 33/574*** | (2006.01) |
| *C12Q 1/6851* | (2018.01) |

(52) U.S. Cl.

CPC ..... *C12Q 1/6886* (2013.01); *G01N 33/57442* (2013.01); *G01N 33/57449* (2013.01); *C12Q 1/6851* (2013.01); *C12Q 2600/154* (2013.01); *C12Q 2600/156* (2013.01); *C12Q 2600/158* (2013.01); *C12Q 2600/16* (2013.01)

(58) Field of Classification Search

None

See application file for complete search history.

(56) References Cited

U.S. PATENT DOCUMENTS

| | | | |
|---|---|---|---|
| 5,750,341 | A | 5/1998 | Macevicz |
| 6,090,935 | A | 7/2000 | Breivik et al. |
| 6,156,504 | A | 12/2000 | Gocke et al. |
| 6,248,521 | B1 | 6/2001 | Van Ness et al. |
| 6,306,597 | B1 | 10/2001 | Macevicz |
| 6,361,940 | B1 | 3/2002 | Van Ness et al. |
| 6,514,736 | B1 | 2/2003 | Erlich et al. |
| 6,576,420 | B1 | 6/2003 | Carson et al. |
| 6,686,157 | B2 | 2/2004 | Ward et al. |
| 6,746,845 | B2 | 6/2004 | Kinzler et al. |
| 6,815,212 | B2 | 11/2004 | Ness et al. |
| 6,890,764 | B2 | 5/2005 | Chee et al. |
| 6,942,968 | B1 | 9/2005 | Dickinson et al. |
| 6,977,153 | B2 | 12/2005 | Kumar et al. |
| 7,056,660 | B1 | 6/2006 | Diehl et al. |
| 7,060,431 | B2 | 6/2006 | Chee et al. |
| 7,115,400 | B1 | 10/2006 | Adessi et al. |
| 7,211,390 | B2 | 5/2007 | Rothberg et al. |
| 7,232,656 | B2 | 6/2007 | Balsubramanian et al. |
| 7,264,929 | B2 | 9/2007 | Rothberg et al. |
| 7,323,305 | B2 | 1/2008 | Leamon et al. |
| 7,323,310 | B2 | 1/2008 | Peters et al. |
| 7,499,806 | B2 | 3/2009 | Kermani et al. |
| 7,682,790 | B2 | 3/2010 | Hollander et al. |
| 7,683,035 | B1 | 3/2010 | Erbacher et al. |

(Continued)

FOREIGN PATENT DOCUMENTS

| | | |
|---|---|---|
| CN | 1360059 A | 7/2002 |
| CN | 102241772 | 11/2011 |

(Continued)

OTHER PUBLICATIONS

Qiu (Nature Genetics, May 2008, vol. 40, pp. 650-655).*

(Continued)

*Primary Examiner* — Jeanine A Goldberg
*Assistant Examiner* — Wahwah T Johnson
(74) *Attorney, Agent, or Firm* — Fish & Richardson P.C.

(57) ABSTRACT

The recently developed liquid-based Papanicolaou (Pap) smear allows not only cytologic evaluation but also collection of DNA for detection of HPV, the causative agent of cervical cancer. We tested these samples to detect somatic mutations present in rare tumor cells that might accumulate in the cervix once shed from endometrial and ovarian cancers. A panel of commonly mutated genes in endometrial and ovarian cancers was assembled and used to identify mutations in all 46 endometrial or cervical cancer tissue samples. We were able also able to identify the same mutations in the DNA from liquid Pap smears in 100% of endometrial cancers (24 of 24) and in 41% of ovarian cancers (9 of 22). We developed a sequence-based method to query mutations in 12 genes in a single liquid Pap smear without prior knowledge of the tumor's genotype.

15 Claims, 11 Drawing Sheets

Specification includes a Sequence Listing.

(56) References Cited

U.S. PATENT DOCUMENTS 7,700,286 B2 4/2010 Stroun et al.
7,702,468 B2 4/2010 Chinitz et al.
7,704,687 B2 4/2010 Wang et al.
7,745,125 B2 6/2010 Gelfand et al.
7,754,429 B2 7/2010 Rigatti et al.
7,776,531 B1 8/2010 Black et al.
7,811,759 B2 10/2010 Han
7,899,626 B2 3/2011 Kruglyak et al.
7,901,897 B2 3/2011 Stuelpnagel et al.
7,948,015 B2 5/2011 Rothberg et al.
7,957,913 B2 6/2011 Chinitz et al.
7,977,108 B2 7/2011 Newhouse et al.
8,021,888 B2 9/2011 Mohammed et al.
8,026,053 B2 9/2011 Samuels et al.
8,043,834 B2 10/2011 Abarzua et al.
8,076,074 B2 12/2011 Mohammed
8,093,063 B2 1/2012 Albitar
8,150,626 B2 4/2012 Fan et al.
8,190,373 B2 5/2012 Huang et al.
8,288,103 B2 10/2012 Oliphant et al.
8,343,718 B2 1/2013 Van Der Werf et al.
8,372,637 B2 2/2013 Hollander
8,481,292 B2 7/2013 Casbon et al.
8,492,089 B2 7/2013 Owen et al.
8,658,572 B2 2/2014 Albert et al.
8,728,732 B2 5/2014 Guerrero Preston et al.
8,741,630 B2 6/2014 Dickinson et al.
8,765,419 B2 7/2014 Hirschbein et al.
8,822,158 B2 9/2014 Froehlich et al.
8,865,410 B2 10/2014 Shendure et al.
8,871,687 B2 10/2014 Strom
8,877,436 B2 11/2014 Eder et al.
8,911,942 B2 12/2014 Mohammed et al.
8,962,250 B2 2/2015 Stanley
9,012,149 B2 4/2015 Kim et al.
9,029,103 B2 5/2015 Rigatti et al.
9,045,796 B2 6/2015 Gunderson et al.
9,051,606 B2 6/2015 Liu et al.
9,074,206 B2 7/2015 Wu et al.
9,085,798 B2 7/2015 Chee et al.
9,115,410 B2 8/2015 Nazarenko et al.
9,163,283 B2 10/2015 Chee et al.
9,222,134 B2 12/2015 Mann
9,228,234 B2 1/2016 Rabinowitz et al.
9,233,125 B2 1/2016 Davila et al.
9,238,832 B2 1/2016 Will et al.
9,279,146 B2 3/2016 Gupta et al.
9,340,830 B2 5/2016 Lipson et al.
9,382,581 B2 7/2016 Froehner et al.
9,389,234 B2 7/2016 Von Hoff et al.
9,399,794 B2 7/2016 Liu
9,404,156 B2 8/2016 Hicks et al.
9,410,206 B2 8/2016 Hoon et al.
9,410,956 B1 8/2016 Cheng
9,422,593 B2 8/2016 Rothmann et al.
9,424,392 B2 8/2016 Rabinowitz et al.
9,441,267 B2 9/2016 Gunderson et al.
9,453,258 B2 9/2016 Kain et al.
9,476,095 B2 10/2016 Vogelstein et al.
9,487,823 B2 11/2016 Lasken et al.
9,546,399 B2 1/2017 Amorese et al.
9,546,404 B2 1/2017 Sanders et al.
9,556,491 B2 1/2017 Hoon
9,567,640 B2 2/2017 Hoon
9,574,234 B2 2/2017 Straus et al.
9,587,273 B2 3/2017 Stuelpnagel et al.
9,593,366 B2 3/2017 Nazarenko et al.
9,598,731 B2 3/2017 Talasaz
9,670,530 B2 6/2017 Kostem et al.
9,689,047 B2 6/2017 O'Neil et al.
9,702,004 B2 7/2017 Van Eijk et al.
9,708,655 B2 7/2017 Mandell et al.
9,745,632 B2 8/2017 Parr et al.
9,760,530 B2 9/2017 Harsha et al.
9,783,847 B2 10/2017 Chee
9,783,854 B2 10/2017 Sanders et al.
9,792,403 B2 10/2017 Sun et al.
9,797,000 B2 10/2017 Lowe et al.
9,816,139 B2 11/2017 Breen
9,828,672 B2 11/2017 Varadarajan et al.
9,834,822 B2 12/2017 Talasaz et al.
9,873,908 B2 1/2018 Gupta et al.
9,879,312 B2 1/2018 Steemers et al.
9,902,992 B2 2/2018 Talasaz et al.
9,914,973 B2 3/2018 Cheng
9,920,366 B2 3/2018 Eltoukhy et al.
9,944,924 B2 4/2018 Rigatti et al.
9,957,570 B2 5/2018 Mori et al.
9,992,598 B2 6/2018 Reiche
10,011,826 B2 7/2018 Hollander et al.
10,011,870 B2 7/2018 Zimmermann et al.
10,017,759 B2 7/2018 Kaper et al.
10,023,904 B2 7/2018 Villahermosa Jaen et al.
10,023,917 B2 7/2018 Buettner et al.
9,965,585 B2 8/2018 Lo et al.
10,041,127 B2 8/2018 Talasaz
10,102,337 B2 10/2018 Scolnick et al.
10,113,199 B2 10/2018 Morin et al.
10,227,652 B2 3/2019 Rabinowitz et al.
10,240,202 B2 3/2019 Rabinowitz et al.
10,266,893 B2 4/2019 Rabinowitz et al.
10,388,403 B2 8/2019 Rava et al.
10,422,006 B2 9/2019 Samuels et al.
10,457,995 B2 10/2019 Talasaz
10,494,678 B2 12/2019 Talasaz
10,501,793 B2 12/2019 Chee et al.
10,501,810 B2 12/2019 Talasaz
10,522,242 B2 12/2019 Rabinowitz et al.
10,526,658 B2 1/2020 Babiarz et al.
10,538,759 B2 1/2020 Stuelpnagel et al.
10,538,814 B2 1/2020 Babiarz et al.
10,557,172 B2 2/2020 Babiarz et al.
10,577,601 B2 3/2020 Shendure et al.
10,590,482 B2 3/2020 Ryan et al.
10,597,653 B2 3/2020 Sabot et al.
10,619,214 B2 4/2020 Lo et al.
10,704,085 B2 7/2020 Talasaz et al.
10,704,086 B2 7/2020 Talasaz et al.
10,704,105 B2 7/2020 Samuels et al.
10,704,108 B2 7/2020 Vogelstein et al.
10,731,220 B2 8/2020 Babiarz et al.
10,732,220 B2 8/2020 Tamura et al.
10,783,364 B2 9/2020 Gao
10,787,713 B2 9/2020 Samuels et al.
10,801,063 B2 10/2020 Eltoukhy et al.
10,822,663 B2 11/2020 Talasaz
10,894,987 B2 1/2021 Vogelstein et al.
2002/0160404 A1 10/2002 Dietmaier et al.
2003/0148335 A1 8/2003 Shen et al.
2005/0136405 A1 6/2005 Linder et al.
2005/0153313 A1 7/2005 Endege et al.
2005/0244847 A1 11/2005 Domanico et al.
2006/0127918 A1 6/2006 Mohammed et al.
2006/0263789 A1 11/2006 Kincaid
2006/0292576 A1 12/2006 Albitar et al.
2007/0020640 A1 1/2007 McCloskey
2007/0269805 A1 11/2007 Hogers
2008/0160580 A1 7/2008 Adessi et al.
2008/0161420 A1 7/2008 Shuber
2008/0286795 A1 11/2008 Kawashima et al.
2009/0088328 A1 4/2009 Mohammed et al.
2009/0105081 A1 4/2009 Rodesch et al.
2009/0215062 A1 8/2009 Lee
2009/0233802 A1 9/2009 Bignell
2009/0298187 A1 12/2009 Nazarenko et al.
2010/0041048 A1 2/2010 Diehl et al.
2010/0127186 A1 4/2010 Bykanov et al.
2010/0113758 A1 5/2010 Wilmer et al.
2010/0129874 A1 5/2010 Mitra et al.
2010/0248991 A1 9/2010 Roesler et al.
2010/0273219 A1 10/2010 May et al.
2011/0152111 A1 6/2011 Fan et al.
2011/0217309 A1 9/2011 Buck et al.
2011/0319415 A1 12/2011 Thomas et al.

(56) References Cited

U.S. PATENT DOCUMENTS

2012/0010091 A1 1/2012 Linnarson
2012/0156753 A1 6/2012 Jendrisak et al.
2012/0225428 A1 9/2012 Beck et al.
2013/0059741 A1 3/2013 Weiner
2013/0266938 A1 10/2013 Will
2013/0296176 A1* 11/2013 Marziali .............. C12Q 1/6869 435/6.12
2014/0011199 A1 1/2014 Speiser et al.
2014/0038837 A1 2/2014 Fung et al.
2014/0050788 A1 2/2014 Daniel et al.
2014/0066317 A1 3/2014 Talasaz
2014/0128270 A1 5/2014 Nakao
2014/0271635 A1 9/2014 Brogdon et al.
2014/0336996 A1 11/2014 Sun et al.
2014/0364323 A1 12/2014 Fan et al.
2015/0011416 A1 1/2015 Lei et al.
2015/0024948 A1 1/2015 Dugas et al.
2015/0051085 A1 2/2015 Vogelstein et al.
2015/0087535 A1 3/2015 Patel
2015/0093756 A1 4/2015 Wolff et al.
2015/0176071 A1 6/2015 Fisher et al.
2015/0197787 A1 7/2015 Welder et al.
2015/0225775 A1 8/2015 Satya
2015/0252415 A1 9/2015 Vogelstein et al.
2015/0275267 A1 10/2015 O'Neil et al.
2015/0307947 A1 10/2015 Basu et al.
2015/0324519 A1 11/2015 Liu
2015/0360193 A1 12/2015 Fan et al.
2016/0017320 A1 1/2016 Wang et al.
2016/0026758 A1 1/2016 Jabara et al.
2016/0048564 A1 2/2016 Bassett, Jr. et al.
2016/0092630 A1 3/2016 Chen et al.
2016/0194404 A1 7/2016 June et al.
2016/0251704 A1 9/2016 Talasaz et al.
2016/0273049 A1 9/2016 Velculescu et al.
2016/0281154 A1 9/2016 So et al.
2016/0319345 A1 11/2016 Gnerre et al.
2016/0374330 A1 12/2016 Grolz
2017/0009287 A1 1/2017 Brastaad et al.
2017/0039328 A1 2/2017 Kathleen et al.
2017/0058332 A1 3/2017 Kermani et al.
2017/0061072 A1 3/2017 Kermani et al.
2017/0101676 A1 4/2017 Teng et al.
2017/0137876 A1 5/2017 Rigatti et al.
2017/0141793 A1 5/2017 Straus et al.
2017/0165289 A1 6/2017 Minomi et al.
2017/0175197 A1 6/2017 Gatalica et al.
2017/0183742 A1 6/2017 Thierry et al.
2017/0240972 A1 8/2017 Mokhtari et al.
2017/0240973 A1 8/2017 Eltoukhy et al.
2017/0260590 A1 9/2017 Eltoukhy et al.
2017/0314081 A1 11/2017 Gutin et al.
2017/0316149 A1 11/2017 Maston
2017/0356030 A1 12/2017 Boyanov et al.
2017/0356053 A1 12/2017 Otto et al.
2018/0002738 A1 1/2018 Wang et al.
2018/0002749 A1 1/2018 Larson et al.
2018/0016640 A1 1/2018 Xu et al.
2018/0023119 A1 1/2018 Adey et al.
2018/0037950 A1 2/2018 Gunderson et al.
2018/0051329 A1 2/2018 Elzinga
2018/0087105 A1 3/2018 Larson et al.
2018/0095969 A1 4/2018 Jung et al.
2018/0100859 A1 4/2018 Cardone et al.
2018/0119216 A1 5/2018 Jamshidi et al.
2018/0120291 A1 5/2018 Eltoukhy et al.
2018/0135044 A1 5/2018 Sausen et al.
2018/0135103 A1 5/2018 Furlan et al.
2018/0141020 A1 5/2018 Gunderson et al.
2018/0142304 A1 5/2018 Sanders et al.
2018/0148716 A1 5/2018 Heitz et al.
2018/0155705 A1 6/2018 Wolf et al.
2018/0155774 A1 6/2018 Gunderson et al.
2018/0163201 A1 6/2018 Larson
2018/0171337 A1 6/2018 O'Neil et al.
2018/0195131 A1 7/2018 Mortimer
2018/0201974 A1 7/2018 Fraser
2018/0201992 A1 7/2018 Wu et al.
2018/0203974 A1 7/2018 Venn
2018/0208999 A1 7/2018 Lo et al.
2018/0258490 A1 9/2018 Wang
2019/0206510 A1 7/2019 Jiang et al.
2019/0256924 A1 8/2019 Vogelstein et al.
2019/0287654 A1 9/2019 Curtis et al.
2019/0376137 A1 12/2019 Vogelstein et al.
2020/0013482 A1 1/2020 Sikora
2020/0131568 A1 4/2020 Talasz et al.
2020/0157636 A1 5/2020 Velculescu et al.
2020/0377956 A1 12/2020 Vogelstein et al.

FOREIGN PATENT DOCUMENTS

EP 1910560 12/2010
EP 3443119 2/2019
EP 3177740 1/2021
WO WO 2001/023618 4/2001
WO WO 2002/012897 2/2002
WO WO 2002/016649 2/2002
WO WO 2002/059355 8/2002
WO WO 2002/099982 12/2002
WO WO 2008030186 3/2008
WO 2008118877 A2 10/2008
WO WO 2009/152928 12/2009
WO WO 2010/028098 3/2010
WO WO 2010/126614 11/2010
WO WO 2010/127186 11/2010
WO WO 2010/141955 12/2010
WO WO 2012/038839 3/2012
WO WO 2012/092336 7/2012
WO WO 2012/142213 10/2012
WO WO 2013/113816 8/2013
WO WO 2013/148496 10/2013
WO WO 2014183078 11/2014
WO WO 2015/198074 12/2015
WO WO 2016/130704 8/2016
WO WO 2016/135300 9/2016
WO WO 2016/140974 9/2016
WO WO 2016/141169 9/2016
WO WO 2016/170147 10/2016
WO WO 2016134136 11/2016
WO WO 2016/193490 12/2016
WO WO 2017/019456 2/2017
WO WO 2017/032808 3/2017
WO WO 2017/053915 3/2017
WO WO 2017/085321 5/2017
WO WO 2017/123316 7/2017
WO WO 2017/127741 7/2017
WO WO 2017/132276 8/2017
WO WO 2017/132438 8/2017
WO WO 2017136603 8/2017
WO WO 2017/151524 9/2017
WO WO 2017/181134 10/2017
WO WO 2017/181146 10/2017
WO WO 2017/197027 11/2017
WO WO 2017/201315 11/2017
WO WO 2017/205686 11/2017
WO WO 2017/218512 12/2017
WO WO 2018/009723 1/2018
WO WO 2018/013598 1/2018
WO WO 2018/057770 3/2018
WO WO 2018/064629 4/2018
WO WO 2018/068014 4/2018
WO WO 2018064229 4/2018
WO WO 2018/077847 5/2018
WO WO 2018/081130 5/2018
WO WO 2018/085862 5/2018
WO WO 2018/093780 5/2018
WO WO 2018/111872 6/2018
WO WO 2018/119399 6/2018
WO WO 2018/119452 6/2018
WO WO 2018119438 6/2018
WO WO 2018/125892 7/2018
WO WO 2018/136416 7/2018
WO WO 2018/137826 8/2018

(56) References Cited

FOREIGN PATENT DOCUMENTS

| | | |
|---|---|---|
| WO | WO 2018093744 | 8/2018 |
| WO | WO 2018177847 | 10/2018 |
| WO | WO 2018/218113 | 11/2018 |
| WO | WO 2018204657 | 11/2018 |
| WO | WO 2020021119 | 1/2020 |

OTHER PUBLICATIONS

The Cancer Genome Atlas Research Network (Nature, Jun. 2011, vol. 474, pp. 609-616).*
Schorge (Cancer (Cancer Cytopathol) 2002; 96:338-43).*
Sharma (EJSO 2006, vol. 32, pp. 818-824).*
McConechy (J Path 2012; 228:20-30 and supplementary table, pp. 1-11).*
Dokianakis (Clin & Exp. Metastasis 17: 293-297, 1999).*
Walsh et al. Mutations in 12 genes for inherited ovarian, fallopian tube, and peritoneal carcinoma identified by massively parallel sequencing. PNAS; 2011 108; 44: p. 1-6.(Epub Oct. 17, 2017) (Year: 2011).*
Sharma and Menon. Screening for gynaecological cancers. EJSO; 2006; vol. 32: p. 818-824. (Year: 2006).*
Kinde et al. Detection and quantification of rare mutations with massively parallel sequencing. PNAS; 2011; 108: 9530-9535. (Year: 2011).*
Dokianakis et al. Ras gene activation in malignant cells of human ovarian carcinoma peritoneal fluids. Clinical & Experimental Metastasis; 1999; 17: 293-297. (Year: 1999).*
McConechy et al. Use of mutation profiles to refine the classification of endometrial carcinomas. J Path; 2012; 228: 20-30. (Year: 2012).*
McConechy et al. Use of mutation profiles to refine the classification of endometrial carcinomas. J Path; 2012; 228: 20-30. Supplemental Table 1. (Year: 2012).*
McConechy et al. Use of mutation profiles to refine the classification of endometrial carcinomas. J Path; 2012; 228: 20-30. Supplemental Table 2. (Year: 2012).*
Kinde et al. PNAS; 2011; 108:9530-9535 cited on IDS. (Year: 2011).*
Kuhn et al. Identification of Molecular Pathway Aberrations in Uterine Serous Carcinoma by Genome-wide Analyses. J Natl Cancer Inst. 2012; 104:1503-1513. (Year: 2012).*
Kuhn et al. Identification of Molecular Pathway Aberrations in Uterine Serous Carcinoma by Genome-wide Analyses. J Natl Cancer Inst. 2012; 104:1503-1513. Supplemental Table 2. (Year: 2012).*
Moreno-Bueno et al. Abnormalities of the APC/b-catenin pathway in endometrial cancer. Oncogene; 2002; 21: 7981-7990. (Year: 2002).*
Ellenson and Wu. Focus on endometrial and cervical cancer. Cancer Cell; 2004; 5; p. 533-538. (Year: 2004).*
Sharma and Menon. EJSO; 2006; vol. 32: pp. 818-824. (Year: 2006).*
Kinde et al. PNAS; 2011; 108: 9530-9535. (Year: 2011).*
McConechy et al. J Path; 2012; 228: 20-30 and Supplementary Tables 1-2. (Year: 2012).*
Kuhn et al. J Natl Cancer Inst. Aug. 2012; 104:1503-1513. (Year: 2012).*
Moreno-Bueno et al. Oncogene; 2002; 21: 7981-7990. (Year: 2002).*
Dokianakis et al. Clinical & Experimental Metastasis; 1999; 17: 293-297. (Year: 1999).*
Walsh et al. PNAS; 2011 108; 44: p. 1-6 (Epub Oct. 17, 2017). (Year: 2011).*
Spruck et al. Cancer Research; 2002; 62, 4535-4539. (Year: 2002).*
Cassia et al. Pathol 2003; 201: 589-595. (Year: 2003).*
Akhoondi et al. Cancer Res; 2007; 67: (19): 9006-9012. (Year: 2007).*
Sams et al., 'Liquid-based Papanicolaou tests in endometrial carcinoma diagnosis. Performance, error root cause analysis, and quality improvement' American Journal of Clinical Pathology, vol. 137, No. 2, pp. 248-254 (Feb. 28, 2012).
SUH et al., 'Major clinical research advances in gynecologic cancer in 2011' Journal of Gynecologic Oncology, vol. 23, No. 1, pp. 53-64 (Jan. 9, 2012).
Kinde et al., 'Evaluation of DNA from the Papanicolaou test to detect ovarian and endometrial cancers' Science Translational Medicine. vol. 5, Issue 167, Article No. 164ra, pp. 1-10 (Jan. 9, 2013).
International Search Report and Written Opinion for PCT/US2013/065342, dated Apr. 1, 2014.
European Office Action issued in related European Application No. 13851273.6, dated Apr. 19, 2017.
Kang et al., "Inverse correlation between RASSF1A hypermethylation, KRAS and BRAF mutations in cervical adenocarcinoma," Gynecology Oncology, 105 (2007) 662-666.
Chinese Office Action dated Mar. 3, 2017 in related Chinese Application No. 201380068411.8.
Ikediobi et al., "Mutation analysis of 24 known cancer genes in the NCI-60 cell line set," Molecular Cancer Therapeutics, 5(11), Nov. 2006.
Hennessy et al., "Ovarian cancer," Lancet, vol. 374, Oct. 17, 2009.
Byron et al., "FGFR2 mutations are rare across histologic subtypes of ovarian cancer," Gynecologic Oncology 117 (2010), 125-129.
Kurman et al., "Molecular pathogenesis and extraovarian origin of epithelial ovarian cancer-Shifting the paradigm," Human Pathology (2011) 42, 918-931.
Huntsman et al. "MLL2, the second human homolog of the Drosophila trithorax gene, maps to 19q13.1 and is amplified in solid tumor cell lines," Oncogene (1999), 18, 7975-7984.
International Search Report and Writen Opinion for PCT/US2013/065342, dated Apr. 1, 2014.
Extended European Search Report issued in related European Application No. 13851273.6, dated Jun. 1, 2016.
Elmasry et al., "Genetic mutations in gynaecological cancers," Reviews in Gynaecological and Preinatal Practice, vol. 6, No. 3-4, Sep. 1, 2006, pp. 115-125.
Bell et al., "Integrated genomic analyses of ovarian carcinoma," Nature, vol. 474, No. 7353, Jun. 1, 2011, pp. 609-615.
Kuhn et al, "Identification of Molecular Pathway Aberrations in Uterine Serous Carcinoma by Genome-wide Analyses," Journal of the National Cancer Institute, vol. 104, No. 19, Aug. 23, 2012, pp. 1503-1513.
Kinde et al., "Detection and quantification of rare mutations with massively parallel sequencing," PNAS, vol. 108, No. 23, May 17, 2011, pp. 9530-9535.
Ernani et al, "Agilent's SureSelect Target Enrichment System: Brining Cost and Process Efficiency to Next-Generation Sequencing," Agilent Technologies—Product Notes, Mar. 16, 2009, pp. 1-8.
Japanese Office Action issued in related Japanese Application No. 201380068411.8, dated Apr. 19, 2016.
Zhang, "Study of Use of Liquid-based Cytologic Test in Cervical Cancer and Endometrial Carcinoma Screening," China Master Dissertations Full-text Database, 2005, No. 8, pp. 4-28.
Oda et al., "High Frequency of Coexistent Mutations of PIK3CA and PTEN Genes in Endometrial Carcinoma," Cancer Research, vol. 65, No. 23, Dec. 1, 2005, pp. 10669-10673.
Malpica et al., "Grading ovarian serous carcinoma using a two-tier system," *Am J Surg Pathol* 28, 496-504 (2004).
ACOG Committee Opinion: No. 280, Dec. 2002. The role of the generalist obstetrician-gynecologist in the early detection of ovarian cancer, Obstet Gynecol 100, 1413-1416 (2002).
ACOG Practice Bulletin. Clinical Management Guidelines for Obstetrician-Gynecologists. No. 60, Mar. 2005, Pregestational diabetes mellitus. Obstet Gynecol 1 05, 675-685 (2005).
American Cancer Society. Detailed guide: ovarian cancer—can ovarian cancer be found early? (Available at http://www.cancer.org/Cancer/OvarianCancer/DetailedGuide/ovariancancer-detection).
Vogelstein et al., Cancer genes and the pathways they control. Nat ~Med 10, 789-799 (2004).
Hamilton et al., Uterine papillary serous and clear cell carcinomas predict for poorer survival compared to grade 3 endometrioid corpus cancers. Br J Cancer 94, 642-646 (2006).

(56) References Cited

OTHER PUBLICATIONS

Gunderson et al., "Oncologic and reproductive outcomes with progestin therapy in women with endometrial hyperplasia and grade 1 adenocarcinoma: a systematic review," Gynecol Oncol 125, 477-482 (2012).
DeSimone et al., Rate of pathology from atypical glandular cell Pap tests classified by the Bethesda 2001 nomenclature. Obstet Gynecol 107, 1285-1291 (2006).
Rago, et al., Serial assessment of human tumor burdens in mice by the analysis of circulating DNA. Cancer Res 67, 9364-9370 (2007).
Geier et al., Clinical evaluation of atypical glandular cells of undetermined significance. Am J Obstet Gynecol 184, 64-69 (2001).
Barrow et al., Cumulative lifetime incidence of extracolonic cancers in Lynch syndrome: a report of 121 families with proven mutations. Clin Genet 75, 141-149 (2009).
Kuhn et al., Identification of Molecular Pathway Aberrations in Uterine Serous Carcinoma by Genome-wide Analyses. J Natl Cancer Inst, (2012).
Partridge et al., Results from four rounds of ovarian cancer screening in a randomized trial. Obstet Gynecol 113, 775-782 (2009).
Bray et al., Global estimates of cancer prevalence for 27 sites in the adult population in 2008. Int J Cancer, (2012).
Meden et al., CA 125 in benign gynecological conditions. Int J Biol Alarkers 13, 231-237 (1998).
Mitchell et al., Accuracy and survival benefit of cytological prediction of endometrial carcinoma on routine cervical smears. Int J Gynecol Pathol 12, 34-40 (1993).
Traut et al., Cancer of the Uterus: The Vaginal Smear in Its Diagnosis. Cal West J\!fed 59, 121-122 (1943).
Kinde et al., Detection andquantification of rare mutations with massively parallel sequencing. Proc Natl Acad Sci US A 108, 9530-9535 (2011).
Bell et al., Integrated genomic analyses of ovarian carcinoma. Nature 474, 609-615 (2011).
International Preliminary Report on Patentability issued in PCT/US2013/065342, dated May 5, 2015, 7 pages.
He et al., IgH gene rearrangements as plasma biomarkers in Non-Hodgkin's lymphoma patients. Oncotarget2, 178-185 (2011).
Wu et al., Recurrent GNAS mutations define an unexpected pathway for pancreatic cyst development. Sci Transl Afed 3, 92ra66 (2011).
Cooper et al., Endometrial sampling techniques in the diagnosis of abnormal uterine bleeding. Obstet Gynecol Clin North Am 27, 235-244 (2000).
Marques et al., Atypical glandular cells and cervical cancer: systematic review. Rev Assoc Af ed Bras 57, 234-238 (2011).
Carlson et al., Screening for ovarian cancer. Ann Intern Afrd 121, 124-132 (1994).
Ries et al., SEER Survival Afonograph: Cancer Survival Among Adults: US SEER Program, 1988-2001, Patient and Tumor Characteristics (NIH Pub. No. 07-6215. National Cancer Institute, Bethesda, MD, 2007).
Arbyn et al., European Guidelines for Quality Assurance in Cervical Cancer Screening. Second edition—summary document. *Ann Oncol* 21, 448-458 (2010).
Mayrand et al., Human papillomavirus DNA versus Papanicolaou screening tests for cervical cancer. N Engl J Med 357, 1579-1588 (2007).
Howlader et al., SEER Cancer Statistics Review, 1975-2009 (National Cancer Institute.Bethesda, MD, 2012).
Lindor et al.,Press, Recommendations for the care of individuals with an inherited predisposition to Lynch syndrome: a systematic review. JA,HA 296, 1507-1517 (2006).
Naucler et al.,Human papillomavirus and Papanicolaou tests to screen for cervical cancer. N Engl J 1\fed 357, 1589-1597 (2007).
Smith et al.,Transvaginal ultrasound for identifying endometrial abnormality. Acta Obstet Gynecol Scand 70, 591-594 (1991).
Bristow et al., Survival effect of maximal cytoreductive surgery for advanced ovarian carcinoma during the platinum era: a meta-analysis. J Clin Oncol 20, 1248-1259 (2002).
Insinga et al., Diagnoses and outcomes in cervical cancer screening: a population-based study. Am J Obstet Gynecol 191, 105-113 (2004).20.
Forbes et al., COSMIC: mining complete cancer genomes in the Catalogue of Somatic Mutations in Cancer. Nucleic Acids Res 39, D945-950 (2011).
Sams et al.., Liquid-based Papanicolaou tests in endometrial carcinoma diagnosis. Performance, error root cause analysis, and quality improvement. Am J Clin Pathol 137, 248-254 (2012).
Jones et al., Papadopoulos, Frequent mutations of chromatin remodeling gene ARID1A in ovarian clear cell carcinoma. Science 330, 228-231 (2010).
Jones et al., Low-grade serous carcinomas of the ovary contain very few point mutations. J Pathol 226, 413-420 (2012).
Pecorelli, Revised FIGO staging for carcinoma of the vulva, cervix, and endometrium. Int J Gynaecol Obstet 105, 103-104 (2009).
Rozen et al.,Primer3 on the WWW for general users and for biologist programmers. Methods Afol Biol 132, 365-386 (2000).
Buys et al., Effect of screening on ovarian cancer mortality: the Prostate, Lung, Colorectal and Ovarian (PLCO) Cancer Screening Randomized Controlled Trial. JAMA 305, 2295-2303 (2011).
Screening for ovarian cancer: recommendation statement. U.S. Preventive Services Task Force. Am Fam Physician 71, 759-762 (2005).
Sharpless et al., Dysplasia associated with atypical glandular cells on cervical cytology. Obstet Gynecol 1 05, 494-500 (2005).
Extended European Search Report in Application No. 18193794.7, dated Dec. 19, 2018.
Patel et al., "Endometrial carcinoma detected with SurePath liquid-based cervical cytology: comparison with conventional cytology", CYTOPATHOLOGY, vol. 20, No. 6, pp. 380-387, 2009.
"Consensus sequence" (online) Oct. 4, 2011 <https://en.wikipedia.org/w/index.php?title=Consensus_sequence&oldid=423354064>.
"Polymerase chain reaction" (online) 2011, <https://web.archive.org/web/20110203140027/https:en.wikipedia.org/wiki/Polymerase>.
Abbosh et al., "Phylogenetic ctDNA analysis depicts early-stage lung cancer evolution", Nature 545: 446-451, 2017.
Abdel-Rahman, "Denosumab versus zoledronic acid to prevent aromatase inhibitors-associated fractures in postmenopausal early breast cancer; a mixed treatment meta-analysis.", Expert Rev Anticancer Ther 16(8): 885-91, 2016.
Agus et al., "Targeting ligand-activated ErbB2 signaling inhibits breast and prostate tumor growth", Cancer Cell 2: 127-137, 2002.
Albert et al., "Direct selection of human genomic loci by microarray hybridization", Nat. Methods 4: 903-905, 2007.
Albertini et al., "In vivo somatic mutations in humans: measurement and analysis.", Annu Rev Genet 24: 305-326, 1990.
AlHilli et al., "Incidence and factors associated with synchronous ovarian and endometrial cancer: a population-based case-control study.", Gynecologic oncology 125: 109-113, 2012.
Allegra et al., "American Society of Clinical Oncology provisional clinical opinion: testing for KRAS gene mutations in patients with metastatic colorectal carcinoma to predict response to anti-epidermal growth factor receptor monoclonal antibody therapy.", J. Clin. Oncol. 27: 2091-2096, 2009.
Allen et al., "Multi-institutional Validation Study of the American Joint Commission on Cancer (8th Edition) Changes for T and N Staging in Patients With Pancreatic Adenocarcinoma.", Ann Surg 265(1): 185-191, 2017.
Allory et al., "Telomerase Reverse Transcriptase Promoter Mutations in Bladder Cancer: High Frequency Across Stages, Detection in Urine, and Lack of Association with Outcome", Eur Urol 65: 360-366, 2014.
Alvarez et al., "Widespread Hypomethylation Occurs Early and Synergizes with Gene Amplification during Esophageal Carcinogenesis", PLOS Genetics, vol. 7, issue 3, e1001356, 1-14 pages, 2011.
Alvarez-Chaver et al., "Proteomics for discovery of candidate colorectal cancer biomarkers", World J. Gastroenterol. 20(14): 3804-3 824, 2014.
Andre et al., "Improved overall survival with oxaliplatin, fluorouracil, and leucovorin as adjuvant treatment in stage II or III colon cancer in the MOSAIC trial.", J Clin Oncol 27(19): 3109-3116, 2009.

(56) References Cited

OTHER PUBLICATIONS

Anglesio et al., "Cancer-Associated Mutations in Endometriosis without Cancer", N Engl J Med 376: 1835-1848, 2017.
Ansari et al.,"Relationship between tumour size and outcome in pancreatic ductal adenocarcinoma", Br J Surg 104(5): 600-607, 2017.
Antoni et al., "Bladder Cancer Incidence and Mortality: A Global Overview and Recent Trends.", Eur Urol, 71(1), 96-108, 2017.
Araten et al., A quantitative measurement of the human somatic mutation rate., Cancer Res 65: 8111-8117, 2005.
Arnold et al., "Global burden of cancer attributable to high body-mass index in 2012: a population-based study.", The Lancet. Oncology 16, 36-46, 2015.
Audeh et al., "Oral poly(ADP-ribose) polymerase inhibitor olaparib in patients with BRCA1 or BRCA2 mutations and recurrent ovarian cancer: a proof-of-concept trial.", Lancet 376: 245-251, 2010.
Awada et al., "An open-label, dose-escalation study to evaluate the safety and pharmacokinetics of CEP-9722 (a PARP-1 and PARP-2 inhibitor) in combination with gemcitabine and cisplatin in patients with advanced solid tumors", Anticancer Drugs 27(4): 342-8, 2016.
Baard et al., Diagnostic dilemmas in patients with upper tract urothelial carcinoma., Nat Rev Urol, 14(3), 181-191, 2017.
Baehner, "The analytical validation of the Oncotype DX Recurrence Score assay", Ecancermedicalscience 10: 675, 2016.
Bahuva et al., "Morphologic abnormalities are poorly predictive of visceral pain in chronic pancreatitis.", Pancreas 42(1): 6-10, 2013.
Bainbridge et al., "Whole exome capture in solution with 3 Gbp of data" Genome Biology, 11(6): R62, 2010.
Bang et al., "Trastuzumab in combination with chemotherapy versus chemotherapy alone for treatment of HER2-positive advanced gastric or gastro-oesophageal junction cancer (ToGA): a phase 3, open-label, randomised controlled trial", Lancet 376: 687-697, 2010.
Bansal et al., "Low-and high-grade bladder cancer appraisal via serum-based proteomics approach,", Clin Chim Acta 436: 97-103, 2014.
Bardelli et al., "Liquid Biopsies, What We Do Not Know (Yet)", Cell Press, 31, 172-179, 2017.
Baretton et al., "Inerphase Cytogenetic Analysis of Prostatic Carcinomas by Use of Nonisotopic in Situ Hybridization", Cancer Research 54, 4472-4480, 1994.
Barkan et al., "The Paris System for Reporting Urinary Cytology: The Quest to Develop a Standardized Terminology,", Adv AnatPathol 23:193-201, 2016.
Barnes, "The fidelity of Taq polymerase catalyzing PCR is improved by an N-terminal deletion", Gene 112:29-35, 1992.
Barroso-Sousa et al., "Clinical Development of the CDK4/6 Inhibitors Ribociclib and Abemaciclib in Breast Cancer", Breast Care 11(3): 167-173, 2016.
Baselga et al., "Pertuzumab plus Trastuzumab plus Docetaxel for Metastatic Breast Cancer", N Engl J Med 366: 109-119, 2012.
Beddowes et al., "Predicting treatment resistance and relapse through circulating DNA.", Breast 34(Suppl 1): S3 1-S35, 2017.
Bell et al., "A simple way to treat PCR products prior to sequencing using ExoSAP-IT" BioTechniques, 2008.
Benson et al., "Colon Cancer, Version 1.2017", NCCN, vol. 15, No. 3, 370-398, 2017.
Beroukhim et al., "Assessing the significance of chromosomal aberrations in cancer: Methodology and application to glioma", Proceedings of the National Academy of Sciences, 104: 20007-20012, 2007.
Bertone et al., "Design optimization methods for genomic DNA tiling arrays", Genome Res 16(2): 271-281, 2006.
Bettegowda et al., "Detection of Circulating Tumor DNA in Early- and Late-Stage Human Malignancies", Science translational medicine 6(224): 224ra224, 2014.
Biankin et al., "Pancreatic cancer genomes reveal aberrations in axon guidance pathway genes.", Nature 491(7424): 399-405, 2012.
Bielas et al., "Quantification of random genomic mutations.", Nat. Methods, 2: 285-290, 2005.
Binladen et al., "The Use of Coded PCR Primers Enables High-Throughput Sequencing of Multiple Homolog Amplification Products by 454 Parallel Sequencing" PLoS One, 9 pages, Feb. 14, 2007.
Boyd et al., "Measurement and clinical monitoring of human lymphocyte clonality by massively parallel VDJ pyrosequencing.", Science Trans lat. Med., vol. 1, 12ra23, Supplementary material, pp. 1-30, 2009.
Bozic et al., "Evolutionary dynamics of cancer in response to targeted combination therapy", Elife 2: e00747, 2013.
Brahmer et al., "Safety and activity of anti-PD-L1 antibody in patients with advanced cancer.", N Engl J Med, 366(26): 2455-65, 2012.
Burris et al., "Phase I trial of novel kinesin spindle protein (KSP) inhibitor SB-715992 IV days 1, 8, 15 q 28 days", J. Clin. Oncol. 22: 128, 2004.
Calvez-Kelm et al., "KRAS mutations in blood circulating cell-free DNA: a pancreatic cancer case-control", ONCOTARGET, vol. 7, No. 48, 2016.
Camidge et al., "A phase I safety, tolerability, and pharmacokinetic study of enzastaurin combined with capecitabine in patients with advanced solid tumors", Anticancer Drugs 19: 77-84, 2008.
Campbell et al., "No difference in stem cell somatic mutation between the background mucosa of right-and left-sided sporadic colorectal carcinomas.", J Pathol 186: 31-35, 1998.
Cancer Genome Atlas Research Network, "Comprehensive molecular characterization of urothelial bladder carcinoma.", Nature 507: 315-322, 2014.
Cancer Genome Atlas Research, "Integrated genomic characterization of endometrial carcinoma.", Nature 497: 67-73, 2013.
Capello et al., "Sequential Validation of Blood-Based Protein Biomarker Candidates for Early-Stage Pancreatic Cancer.", J Natl Cancer Inst 109(4), 2017.
Casbon et al., "A method for counting PCR template molecules with application to next-generation sequencing," Nucleic Acids Research, 1-8, 2011.
Chai et al., Field effect in cancer-an update. Ann Clin Lab Sci 39: 331-337, 2009.
Chan et al., "Size Distributions of Maternal and Fetal DNA in Maternal Plasma", Clinical chemistry 50: 88-92, 2004.
Chan, "Consolidated guidelines on the use of antiretroviral drugs for treating and preventing HIV infection Recommendations for a public health approach", Second Edition, BOOK, 2016.
Chang et al., "CARs: Synthetic Immunoreceptors for Cancer Therapy and Beyond", Trends Mol Med 23(5): 430-450, 2017.
Chari et al., "Probability of pancreatic cancer following diabetes: a population based study". Gastroenterology 129(2): 504-511, 2005.
Chen et al., "Aristolochic acid-associated urothelial cancer in Taiwan", Proc Natl Acad Sci US A, 109(21): 8241-8246, 2012.
Chen et al., "CAR T-cell intrinsic PD-1 checkpoint blockade: A two-in-one approach for solid tumor immunotherapy", Oncoimmunology 6(2): e1273302, 2016.
Chen, "Immune checkpoint inhibitors for nonsmall cell lung cancer treatment", J. Chin Med Assoc 80(1): 7-14, 2017.
Cheng et al., "TERT Promoter Mutations Occur Frequently in Urothelial Papilloma and Papillary Urothelial Neoplasm of Low Malignant Potential.", Eur Urol 71 :497-498, 2017.
Chetverina et al., "Molecular colony diagnostics: detection and quantitation of viral nucleic acids by in-gel PCR.", Biotechniques 33: 150-152, 154, 156, 2002.
Cheung et al., "High frequency of PIK3R1 and PIK3R2 mutations in endometrial cancer elucidates a novel mechanism for regulation of PTEN protein stability.", Cancer Discov 1, 170-185, 2011.
Chiu et al., "Noninvasive prenatal diagnosis of fetal chromosomal aneuploidy by massively parallel genomic sequencing of DNA in maternal plasma", Proc Natl Acad Sci US A 105: 20458-20463, 2008.
Chu et al., J. Clin. Oncol. 22:14S, abstr 2078, 2004.
Chung et al., "A whole-genome mouse BAC microarray with 1-Mb resolution for analysis of DNA copy number changes by array comparative genomic hybridization.", Genome Res. 14(1): 188-196, 2004.
Clarke-Pearson, "Clinical Practice, Screening for ovarian cancer.", N Engl J Med., 361(2): 170-177, 2009.

(56) References Cited

OTHER PUBLICATIONS

Cohen et al., "Combined biomarker-based liquid biopsy for the earlier detection of pancreatic cancers". Proceedings of the National Academy of Sciences of the United States of America, vol. 114, No. 38, pp. 10202-102075, Sep. 2017.
Cohen et al., "Combined circulating tumor DNA and protein biomarker-based liquid biopsy for the earlier detection of pancreatic cancers", PNAS, vol. 114, No. 38, 10202-10207, 2017.
Cohen et al., "Detection and localization of surgically resectable cancers with a multi-analyte blood test", Science, 359(6378): 926-930, 2018.
Cohen et al., "Detection and localization of surgically resectable cancers with a multi-analyte liquid biopsy", Science, 82 pages, 2017.
Cole et al., "Working paper No. 3 Somatic mutant frequency, mutation rates and mutational spectra in the human population in vivo", Mutat Res 304: 33-105, 1994.
Coombs et al., "Therapy-Related Clonal Hematopoiesis in Patients with Non-hematologic Cancers Is Common and Associated with Adverse Clinical Outcomes", Cell Stem Cell 21(3): 374-382, 2017.
Corona et al., "CDK4/6 inhibitors in HER2-positive breast cancer", Cri Rev Oncol Hematol 112: 208-214, 2017.
Cortes et al., "Support-Vector Networks", Machine learning 20: 273-297, 1995.
Costello et al., "Discovery and characterization of artifactual mutations in deep coverage targeted capture sequencing data due to oxidative DNA damage during sample preparation.", Nucleic acids research 41: e67, 2013.
Cowan et al., "Detection of TERT promoter mutations in primary adenocarcinoma of the urinary bladder.", Hum Pathol., 53: 8-13, 2016.
Craig et al., "Identification of genetic variants using bar-coded multiplexed sequencing.", Nat Methods 5: 887-893, 2008.
Cree et al., "The evidence base for circulating tumour DNA blood-based biomarkers for the early detection of cancer: a systematic mapping review", BMC Cancer, 17: 697, 1-17, 2017.
D'Souza et al., "Tumor characterization by ultrasound-release of multiple protein and microRNA biomarkers, preclinical and clinical evidence", PLOS ONE, 1-17 pages, 2018.
Dalma-Weiszhausz et al., "The affymetrix GeneChip platform: an overview.", Methods Enzymol. 410: 3-28, 2006.
Darragh et al., "Tumor Detection by Imaging Proteolytic Activity", Cancer Res 70: 1505-12, 2010.
Davis et al., "Diagnosis, evaluation and follow-up of asymptomatic microhematuria (AMH) in adults: AUA guideline.", J Urol 188: 2473-2481, 2012.
Dawson et al., "Analysis of Circulating Tumor DNA to Monitor Metastatic Breast Cancer", N Engl J Med 368(13): 1199-1209, 2013.
De Boer et al., "An in vitro assay for frameshift mutations: hotspots for deletions of 1 bp by Klenow-fragment polymerase share a consensus DNA sequence.", Genetics 118: 181-191, 1988.
De Vos et al., "Novel PMS2 Pseudogenes Can Conceal Recessive Mutations Causing a Distinctive Childhood Cancer Syndrome", American journal of human genetic, 74: 954-964, 2004.
Demeure et al., "Whole-genome Sequencing of an Aggressive BRAF Wild-type Papillary Thyroid Cancer Identified EML4—ALK Translocation as a Therapeutic Target", World J Surg., 38: 1296-305, 2014.
DeRisi et al., "Use of a cDNA microarray to analyse gene expression patterns in human cancer.", Nat. Genet. 14: 457-460, 1996.
Di Renzo et al., "Expression of the MetfHepatocyte Growth Factor Receptor in Human Pancreatic Cancer", Cancer Res 55(5): 1129-1138, 1995.
Di Renzo et al., "Overexpression and amplification of the met/HGF receptor gene during the progression of colorectal cancer,", Clin Cancer Res 1(2): 147-154, 1995.
Diehl et al., "Analysis of mutations in DNA isolated from plasma and stool of colorectal cancer patients." Gastroenterology 135: 489-498, 2008.
Diehl et al., "Detection and quantification of mutations in the plasma of patients with colorectal tumors", Proceedings of the National Academy of Sciences of the United States of America, 102: 16368-16373, 2005.
Dimashkieh et al., "Evaluation of UroVysion and Cytology for Bladder Cancer Detection", Cancer Cytopathol 121: 591-597, 2013.
Dizon et al., "A Phase II Evaluation of Belinostat and Carboplatin in the Treatment of Recurrent or Persistent Platinum-Resistant Ovarian, Fallopian Tube, or Primary Peritoneal Carcinoma: A Gynecologic Oncology Group Study", Gynecol. Oncol. 125(2): 367-371, 2012.
Dizon et al., "Phase II Activity of Belinostat (PXD-101), Carboplatin, and Paclitaxel in Women With Previously Treated Ovarian Cancer", Int J. Gynecol. Cancer 23(3): 533-539, 2012.
Dohm et al., "Substantial biases in ultrashort read data sets from high-throughput DNA sequencing.", Nucleic Acids Res 36:el05, 2008.
Dong et al., "Combining markers with and without the limit of detection.", Stat Med 33(8): 1307-1320, 2014.
Douville et al., "Detection of aneuploidy in patients with cancer through amplification of long interspersed nucleotide elements (LINEs)", PNAS, vol. 115, No. 8, 1871-1876, 2018.
Dressman et al., Transforming single DNA molecules into fluorescent magnetic particles for detection and enumeration of genetic variations. Proc Natl Acad Sci US A 100(15): 8817-8822, 2003.
Drevis et al., "Phase I Clinical Study of AZD2171, an Oral Vascular Endothelial Growth Factor Signaling Inhibitor, in Patients With Advanced Solid Tumors", 25: 3045-2054, 2007.
Druley et al., "Quantification of rare allelic variants from pooled genomic DNA.", Nat Methods 6: 263-265, 2009.
D'Souza et al., "Tumor characterization by ultrasound-release of multiple protein and microRNA biomarkers, preclinical and clinical evidence", PLos One, 13: e0194268, 2018.
Durbin et al., "A map of human genome variation from population-scale sequencing.", Nature 467:1061-1073, 2010.
Dy et al., "Long-Term Survivors of Metastatic Colorectal Cancer Treated with Systemic Chemotherapy Alone: A North Central Cancer Treatment Group Review of 3811 Patients, N0144", Clin Colorectal Cancer 8(2): 88-93, 2009.
Eastman et al., "Maternal viral genotypic zidovudine resistance and infrequent failure of zidovudine therapy to prevent perinatal transmission of human immunodeficiency virus type 1 in pediatric AIDS Clinical Trials Group Protocol 076,", J Infect Dis 177:557-564, 1998.
Easton et al., "Breast and Ovarian Cancer Incidence in BRCA I-Mutation Carriers", Am. J. Hum. Genet. 56: 265-271, 1995.
Eckert et al., "High fidelity DNA synthesis by the Thermus aquaticus DNA polymerase.", Nucleic Acids Res 18: 3739-3744, 1990.
Egawa et al., "Clinicopathological aspects of small pancreatic cancer. Pancreas", 28(3): 235-240, 2004.
Ehab et al., "Profile of palbociclib in the treatment of metastatic breast cancer", Breast Cancer 8: 83-91, 2016.
Eid et al., "Real-time DNA sequencing from single polymerase molecules", Science 323: 133-138, 2009.
Eliassen et al., "Urinary Estrogens and Estrogen Metabolites and Subsequent Risk of Breast Cancer among Premenopausal Women", Cancer Research, vol. 72, issue 3, 696-706, 2012.
Ellinger et al., "Epigenetic biomarkers in the blood of patients with urological malignancies", Expert Rev Mal Diagn 15: 505-516, 2015.
Ellis et al., "Immune Checkpoint Inhibitors for Patients With Advanced NoneSmall-Cell Lung Cancer: A Systematic Review", Clin Lung Cancer pii: S1525-7304(17)30043-8, 2017.
El-Tanani et al., "The regulation and role of osteopontin in malignant transformation and cancer.", Cytokine Growth Factor Rev 17(6): 463-474, 2006.
Elzek et al., "Proteomics of ovarian cancer: functional insights and clinical applications", Cancer Metastasis Rev., 34(1): 83-96, 2015.
Erickson et al., "Detection of somatic TP53 mutations in tampons of patients with highgrade serous ovarian cancer.", Obstetrics and gynecology 124, 881-885, 2014.
Erlich et al., "Alta-Cyclic: a self-optimizing base caller for next-generation sequencing.", Nat Methods 5: 679-682, 2008.

(56) References Cited

OTHER PUBLICATIONS

Ethier et al., "Bone Modifier Use as Adjuvant Therapy for Early Breast Cancer", Curr Oncol Rep 19(3): 15, 2017.
Extended European Search Report issued in related European Application No. 12772013.4, dated Sep. 17, 2014.
Extended European Search Report issued in related European Application No. 17154750.8, dated Aug. 17, 2017.
Faias et al., "Clinical Impact of KRAS and GNAS Analysis Added to CEA and Cytology in Pancreatic Cystic Fluid Obtained by EUS-FNA", Digestive Diseases and Sciences, vol. 63, No. 9, pp. 2351-2361, 2018.
Falchook et al., "Methylation and histone deacetylase inhibition in combination with platinum treatment in patients with advanced malignancies", Investig. New Drugs 31(5): 1192-1200, 2013.
Falzoi et al., "Multiplex genotyping of CYP3A4, CYP3A5, CYP2C9 and CYP2C19 SNPs using MALDI-TOF mass spectrometry", Pharmacogenomics 11: 559-571, 2010.
Fan et al., "Noninvasive diagnosis of fetal aneuploidy by shotgun sequencing DNA from maternal blood.", Proc Natl Acad Sci US A 105: 16266-16271, 2008.
Finn et al., "Palbociclib and Letrozole in Advanced Breast Cancer", N Eng J Med 375: 1925-1936, 2016.
Fishman et al., "The role of ultrasound evaluation in the detection of early-stage epithelial ovarian cancer,", Am J Obstet Gynecol 192, 1214-1221; discussion 1221-1212, 2005.
Fong et al., "Inhibition of poly(ADP-ribose) polymerase in tumors from BRCA mutation carriers.", N Engl J Med 361: 123-134, 2009.
Forbes et al., "COSMIC: somatic cancer genetics at high-resolution", Nucleic Acids Res 45: D777-D783, 2017.
Forshew et al., "Noninvasive identification and monitoring of cancer mutations by targeted deep sequencing of plasma DNA", Sci Transl Med; 4: 136ra68, 2012.
Fradet et al., "Performance characteristics of a new monoclonal antibody test forbladder cancer: ImmunoCyt trade mark.", Can J Urol 4: 400-405, 1997 ABSTRACT.
Friedman et al., "Regularization Paths for Generalized Linear Models via Coordinate Descent", Journal of Statistical Software 33 :74862, 22 pages, 2010.
Frokjaer et al., "Fibrosis, atrophy, and ductal pathology in chronic pancreatitis are associated with pancreatic function but independent of symptoms.", Pancreas 42(7): 1182-1187, 2013.
Fu et al., "Phase 1b-2a study to reverse platinum resistance through use of a hypomethylating agent, azacitidine, in patients with platinum-resistant or platinum-refractory epithelial ovarian cancer.", Cancer 117(8): 1661-1669, 2011.
Fujiwara et al., "Evaluation of Matrix Metalloproteinase-2 (MMP-2) Activity with Film in situ Zymography for Improved Cytological Diagnosis of Breast Tumors", Breast cancer 13: 272-8, 2006.
Fukagawa et al., "MicroRNA-135a-3p as a promising biomarker and nucleic acid therapeutic agent for ovarian cancer", Cancer Science, 108, 886-896, 2017.
Fullwood et al., "Next-generation DNA sequencing of paired-end tags (PET) for transcriptome and genome analyses" Genome Research, 19: 521-532, 2009.
Gam, "Breast cancer and protein biomarkers", World J. Exp. Med. 2(5): 86-91, 2012.
Gangi et al., "Metabolomic profile in pancreatic cancer patients: a consensusbased approach to identify highly discriminating metabolites", Oncotarget, vol. 7, No. 5, 2016.
Gasi et al., "Overexpression of Full-Length ETV1 Transcripts in Clinical Prostate Cancer Due to Gene Translocation", PLOS ONE, vol. 6, issue 1, e16332, 7 pages, 2011.
Geldenhuys et al., "Sensitivity and specificity of the Pap smear for glandular lesions of the cervix and endometrium,", Acta cytologica 51, 4 7-50, 2007.
Gelmon et al., "Olaparib in patients with recurrent high-grade serous or poorly differentiated ovarian carcinoma or triple-negative breast cancer: a phase 2, multicentre, open-label, non-randomised study", Lancet Oncol. 12: 852-61, 2011.
GenBank Accession No. NM000077, "*Homo sapiens* cyclin dependent kinase inhibitor 2A (CDKN2A), transcript variant 1, mRNA", dated Oct. 21, 2018, 7 pages.
GenBank Accession No. NM000142, "*Homo sapiens* fibroblast growth factor receptor 3 (FGFR3), transcript variant 1, mRNA", dated Dec. 23, 2018, 8 pages.
GenBank Accession No. NM000245, "*Homo sapiens* MET proto-oncogene, receptor tyrosine kinase (MET), transcript variant 2, mRNA", dated Jan. 13, 2019, 7 pages.
GenBank Accession No. NM000551, "*Homo sapiens* von Hippel-Lindau tumor suppressor (VHL), transcript variant 1, mRNA", dated Dec. 23, 2018, 7 pages.
GenBank Accession No. NM001005862, "*Homo sapiens* erb-b2 receptor tyrosine kinase 2 (ERBB2), transcript variant 2, mRNA", dated Jan. 13, 2019, 8 pages.
GenBank Accession No. NM001127500, "*Homo sapiens* MET proto-oncogene, receptor tyrosine kinase (MET), transcript variant 1, mRNA",dated Jan. 13, 2019, 7 pages.
GenBank Accession No. NM001130442, "*Homo sapiens* HRas proto-oncogene, GTPase (HRAS), transcript variant 3, mRNA", dated Dec. 23, 2018, 5 pages.
GenBank Accession No. NM001163213, "*Homo sapiens* fibroblast growth factor receptor 3 (FGFR3), transcript variant 3, mRNA", dated Dec. 23, 2018, 7 pages.
GenBank Accession No. NM001195132, "*Homo sapiens* cyclin dependent kinase inhibitor 2A (CDKN2A), transcript variant 5, mRNA", dated Oct. 21, 2018, 7 pages.
GenBank Accession No. NM001289936, "*Homo sapiens* erb-b2 receptor tyrosine kinase 2 (ERBB2), transcript variant 3, mRNA", dated Jan. 13, 2019, 8 pages.
GenBank Accession No. NM001289937, "*Homo sapiens* erb-b2 receptor tyrosine kinase 2 (ERBB2), transcript variant 4, mRNA", dated Jan. 13, 2019, 8 pages.
GenBank Accession No. NM001289938, "*Homo sapiens* erb-b2 receptor tyrosine kinase 2 (ERBB2), transcript variant 5, mRNA", dated Jan. 13, 2019, 6 pages.
GenBank Accession No. NM001318054, "*Homo sapiens* HRas proto-oncogene, GTPase (HRAS), transcript variant 4, mRNA", dated Dec. 23, 2018, 5 pages.
GenBank Accession No. NM001324401, "*Homo sapiens* MET proto-oncogene, receptor tyrosine kinase (MET), transcript variant 3, mRNA", dated Jan. 13, 2019, 5 pages.
GenBank Accession No. NM001324402, "*Homo sapiens* MET proto-oncogene, receptor tyrosine kinase (MET), transcript variant 4, mRNA", dated Jan. 13, 2019, 6 pages.
GenBank Accession No. NM001354723, "*Homo sapiens* von Hippel-Lindau tumor suppressor (VHL), transcript variant 3, mRNA", dated Dec. 23, 2018, 4 pages.
GenBank Accession No. NM001354809, "*Homo sapiens* fibroblast growth factor receptor 3 (FGFR3), transcript variant 4, mRNA", dated Dec. 23, 2018, 6 pages.
GenBank Accession No. NM001354810, "*Homo sapiens* qfibroblast growth factor receptor 3 (FGFR3), transcript variant 5, mRNA", dated Dec. 23, 2018, 6 pages.
GenBank Accession No. NM003482, "*Homo sapiens* lysine methyltransferase 2D (KMT2D), mRNA", dated Jan. 13, 2019, 21 pages.
GenBank Accession No. NM004448, "*Homo sapiens* erb-b2 receptor tyrosine kinase 2 (ERBB2), transcript variant 1, mRNA", dated Jan. 13, 2019, 10 pages.
GenBank Accession No. NM004985, "*Homo sapiens* KRAS proto-oncogene, GTPase (KRAS), transcript variant b, mRNA", dated Jan. 13, 2019, 7 pages.
GenBank Accession No. NM005343, "*Homo sapiens* HRas proto-oncogene, GTPase (HRAS), transcript variant 1, mRNA", dated Dec. 29, 2018, 5 pages.
GenBank Accession No. NM022965, "*Homo sapiens* fibroblast growth factor receptor 3 (FGFR3), transcript variant 2, mRNA", dated Dec. 23, 2018, 6 pages.
GenBank Accession No. NM033360, "*Homo sapiens* KRAS proto-oncogene, GTPase (KRAS), transcript variant a, mRNA", dated Jan. 13, 2019, 8 pages.

(56) References Cited

OTHER PUBLICATIONS

GenBank Accession No. NM058195, "*Homo sapiens* cyclin dependent kinase inhibitor 2A (CDKN2A), transcript variant 4, mRNA", dated Aug. 4, 2018, 6 pages.
GenBank Accession No. NM058196, "*Homo sapiens* cyclin-dependent kinase inhibitor 2A (melanoma, p16, inhibits CDK4) (CDKN2A), transcript variant 2, mRNA", dated Dec. 21, 2003, 19 pages.
GenBank Accession No. NM176795, "*Homo sapiens* HRas proto-oncogene, GTPase (HRAS), transcript variant 2, mRNA", dated Dec. 23, 2018, 5 pages.
GenBank Accession No. NM198156, "*Homo sapiens* von Hippel-Lindau tumor suppressor (VHL), transcript variant 2, mRNA", dated Dec. 23, 2018, 7 pages.
GenBank Release Note v. 220, p. 1 (Jun. 2017).
Geng et al., "Function and clinical significance of circRNAs in solid tumors", Journal of Hematology and Oncology, 11; 98, 20 pages 2018.
Genovese et al., "Clonal hematopoiesis and blood-cancer risk inferred from blood DNA sequence.", N Engl J Med 371(26): 2477-2487, 2014.
Gerlinger et al., "Intratumor heterogeneity and branched evolution revealed by multiregion sequencing,", N Engl J Med 366, 883-892, 2012.
Ghosh et al., "Quantifying the sensitivities of EGF receptor (EGFR) tyrosine kinase inhibitors in drug resistant non-small cell lung cancer (NSCLC) cells using hydrogel-based peptide array.", Biosensors & Bioelectronics 26: 424-31, 2010.
Giacona et al.," Cell-free DNA in human blood plasma: length measurements in patients with pancreatic cancer and healthy controls.", Pancreas 17: 89-97, 1998.
Gilbert et al., "Assessment of symptomatic women for early diagnosis of ovarian cancer: results from the prospective DOvE pilot project.", The Lancet. Oncology 13, 285-291, 2012.
Giligan et al., "American Society of Clinical Oncology Clinical Practice Guideline on uses of serum tumor markers in adult males with germ cell tumors.", J. Clin. Oncol. 28: 3388-3404, 2010.
Giraldez et al., "Droplet Digital PCR for Absolute Quantification of Extracellular MicroRNAs in Plasma and Serum: Quantification of the Cancer Biomarker hsa-miR-141.", Methods Mol. Biol., 1768: 459-74, 2018.
Gomez et al., "Efficacy and safety of lapatinib as first-line therapy for ErbB2-amplified locally advanced or metastatic breast cancer.", J Clin Oncol 26: 2999-30005, 2008.
Gong et al., "Efficacy and safety of everolimus in Chinese metastatic HR positive, HER2 negative breast cancer patients: a real-world retrospective study", Oncotarget, 8(35): 59810-59822, 2017.
Gonzalez-Pons "Colorectal Cancer Biomarkers: Where Are We Now?", Biomed. Res. Int. 2015: 149014, 2015.
Goodison et al., "A multi-analyte assay for the non-invasive detection of bladder cancer.", PLoS One, 7: e47469, 2012.
Gopalakrishna et al., "Anticipatory Positive Urine Tests for Bladder Cancer.", Ann Surg Oncol., 24: 1747-1753, 2017.
Gore et al., "Somatic coding mutations in human induced pluripotent stem cells.", Nature 471: 63-67, 2011.
Grist et al., "In vivo human somatic mutation: frequency and spectmm with age.", Mutat Res 266: 189-196, 1992.
Grollman et al., "Aristolochic acid nephropathy: Harbinger of a global iatrogenic disease.", Environ Mal Mutagen, 54(1): 1-7, 2013.
Gruenberger et al., "Bevacizumab, Capecitabine, and Oxaliplatin As Neoadjuvant Therapy for Patients With Potentially Curable Metastatic Colorectal Cancer", J. Clin Oncol. 26: 1830-1835, 2008.
Guetschow et al., "Detection of prolactin inducible protein mRNA, a biomarker for breast cancer metastasis, using a molecular beacon-based assay.", Anal. Bioanaly. Chem., 404: 399-406, 2012.
Hajdinjak, "Uro Vysion FISH test for detecting urothelial cancers: meta-analysis of diagnostic accuracy and comparison with urinary cytology testing,", Urol Oncol 26: 646-651, 2008.
Halama et al., "Nesting of colon and ovarian cancer cells in the endothelial niche is associated with alterations in glycan and lipid metabolism", Scientific Reports, 7:39999, 10 pages, 2017.
Hall et al., "Linkage of Early-Onset Familial Breast Cancer to Chromosome 17q21", Science 250: 1684-1689, 1990.
Hamanishi et al., "Safety and Anti tumor Activity of Anti-PD-1 Antibody, Nivolumab, in Patients With Platinum-Resistant Ovarian Cancer.", J. Clin. Oncol. 33(34): 4015-4022, 2015.
Hamilton et al., "The Molecular Basis of Turcot's Syndrome", The New England Journal of Medicine 332: 839-847, 1995.
Hamilton et al., "Uterine papillary serous and clear cell carcinomas predict for poorer survival compared to grade 3 endometrioid corpus cancers", British journal of cancer 94: 642-646, 2006.
Hare et al., "mTOR function and therapeutic targeting in breast cancer", Am J Cancer Res 7(3): 383-404, 2017.
Harris et al., "American Society of Clinical Oncology 2007 Update of Recommendations for the Use of Tumor Markers in Breast Cancer", J. Clin. Oncol. 25: 5287-5312, 2007.
He et al., "Heteroplasmic mitochondrial DNA mutations in normal and tumour cells.", Nature 464: 610-614, 2010.
Hecht et al., "A randomized, double-blind, placebo-controlled, phase III study inpatients (Pts) with metastatic adenocarcinoma of the colon or rectum receiving fifirst-line chemotherapy with oxaliplatin/5-flfluorouracil/leucovorin and PTK787/ZK 222584 or placebo (CONFIRM-1)", ASCO Annual Meeting Proceedings J. Clin. Oncol. 23: 16S, abstr. LBA3, 2005.
Hellmann et al., "Nivolumab plus ipilimumab as first-line treatment for advanced non-small-cell lung cancer (CheckMate 012): results of an open-label, phase 1, multicohort study", Lancet Oncol. 18(1): 31-41, 2017.
Henrique et al., "DNA hypomethylation in plasma as a cancer biomarker: when less is more?", Expert Rev. Mol. Diagn., 14: 419-22, 2014.
Henry et al., "Cancer biomarkers", Mol. Oncol. 6: 140-146, 2012.
Herbst et al., "Lung cancer,", N Engl J Med, 359(13): 1367-1380, 2008.
Herman et al., "Filter-based hybridization capture of subgenomes enables resequencing and copy-number detection.", Nat Methods 6: 507-510, 2009.
Hiatt et al., "Parallel, tag-directed assembly of locallt dreived short sequence reads.", Nat Methods, (7) 119-122, 2010.
Hiatt et al., "Single molecule molecular inversion probes for targeted, high-accuracy detection of low-frequency variation,", Genome research 23, 843-854, 2013.
Hoang et al., "Mutational Signature of Aristolochic Acid Exposure as Revealed by Whole-Exome Sequencing", 2013 Science translational medicine 5: 197ral02, 2013.
Hodges et al., "High definition profiling of mammalian DNA methylation by array capture and single molecule bisulfite sequencing," Genome Research, 19: 1593-1605, 2009.
Hogenbirk et al., "Defining chromosomal translocation risks in cancer", PNAS, E3649-E3656, 2016.
Hoque et al., "High-throughput molecular analysis of urine sediment for the detection of bladder cancer by high-density single-nucleotide polymorphism array.", Cancer Res 63: 5723-5726, 2003.
Horn et al., "TERT promoter mutations in familial and sporadic melanoma." Science 339: 959-961, 2013.
Hosein et al., "Evaluating the repair of DNA derived from formalin-fixed paraffin-embedded tissues prior to genomic profiling by SNP—CGH analysis", Lab. Invest., 93, 701-710, 2013.
Hosgood et al., "Mitochondrial DNA copy number and lung cancer risk in a prospective cohort study", Carcinogen., 31: 847-9, 2010.
Hsieh et al., "Prescription profile of potentially aristolochic acid containing Chinese herbal products: an analysis of National Health Insurance data in Taiwan between 1997 and 2003", Chin Med, 3: 13, 6 pages, 2008.
Huang et al., "Comparison of Central HER2 Testing With Quantitative Total HER2 Expression and HER2 Homodimer Measurements Using a Novel Proximity-Based Assay", AM. J. Clin. Pathol. 134: 303-11, 2010.
Huang et al., "Highly recurrent TERT promoter mutations in human melanoma.", Science 339: 957-959, 2013.

(56) References Cited

OTHER PUBLICATIONS

Huang et al., "T-cell invigoration to tumour burden ratio associated with antiPD-1 response.", Nature 545(7652): 60-65, 2017.
Hughes et al., "Expression profiling using microarrays fabricated by an ink-jet oligonucleotide synthesizer,", Nat. Biotechnol. 19(4): 342-347, 2001.
Hui et al., "Pembrolizumab as first-line therapy for patients with PD-L1-positive advanced non-small cell lung cancer: a phase 1 trial", Ann Oncol 28(4): 874-881, 2017.
Hun et al., "Systems approach to characterize the metabolism of liver cancer stem cells expressing CD133", Sci. Rep. 7: 45557, 2017.
Hurst et al., "Comprehensive mutation analysis of the TERT promoter in bladder cancer and detection of mutations in voided urine.", Eur Urol 65: 367-369, 2014.
Hurwitz et al., "Bevacizumab plus Irinotecan, Fluorouracil, and Leucovorin for Metastatic Colorectal Cancer", N. Engl. J. Med. 350: 2335-2342, 2004.
Ikematsu et al., "Serum midkine levels are increased inpatients with various types of carcinomas", Br J Cancer 83(6): 701-706, 2000.
Ingvarsson et al., "Detection of pancreatic cancer using antibody microarray-based serum protein profiling.", Proteomics 8: 2211-9, 2008.
Innis et al., "Protocols for functional genomics" PCR application, (1999).
International Search Report and Written Opinion in International Application No. PCT/US2012/033207, dated Nov. 28, 2012.
International Search Report and Written Opinion in International Application No. PCT/US2018/045669, dated Nov. 28, 2018, 15 pages.
Irizarry et al., "Summaries of Affymetrix GeneChip probe level data", Nucleic Acids Res 31, 4 :el5, 2003.
Isakoff et al., "P3-16-05: A Phase II Trial Expansion Cohort of the PARP Inhibitor Veliparib (ABT888) and Temozolomide in BRCA1/2 Associated Metastatic Breast Cancer.", Cancer Res 71: P3-16-05, 2011.
Ishikawa et al., "Minute carcinoma of the pancreas measuring 1 cm or less in diameter—collective review of Japanese case reports.", Hepatogastroenterology 46(25): 8-15, 1999.
Jabara et al., "Accurate sampling and deep sequencing of the HIV-1 protease gene using a Primer ID.", Proceedings of the National Academy of Sciences of the United States of America 108, 20166-20171, 2011.
Jacobs et al., Sensitivity of transvaginal ultrasound screening for endometrial cancer in postmenopausal women: a case-control study within the UKCTOCS cohort. The Lancet. Oncology 12, 38-48, 2011.
Jahr et al., "DNA Fragments in the Blood Plasma of Cancer Patients: Quantitations and Evidence for Their Origin from Apoptotic and Necrotic Cells", Cancer Research 61: 1659-1665, 2001.
Jaiswal et al., "Age-related clonal hematopoiesis associated with adverse outcomes.", N Engl J Med 371(26): 2488-2498, 2014.
Jasmine et al., "A Genome-Wide Study of Cytogenetic Changes in Colorectal Cancer Using SNP Microarrays: Opportunities for Future Personalized Treatment", PLoS One 7(2): e31968, 18 pages, 2012.
Jelakovic et al., "Aristolactam-DNA adducts are a biomarker of environmental exposure to aristolochic acid", Kidney Int. 81(6): 559-67, 2012.
Jiao et al., "DAXX/ATRX, MEN1, and mTOR Pathway Genes Are Frequently Altered in Pancreatic Neuroendocrine Tumors", Science 331: 1199-1203, 2011.
Jones et al., "Core signaling pathways in human pancreatic cancers revealed by global genomic analyses.", Science 321(5897): 1801-1806, 2008.
Jones et al., "The epigenomics of cancer,", Cell 128: 683-692, 2007.
Ju et al., "Origins and functional consequences of somatic mitochondrial DNA mutations in human cancer", eLife 3, 28 pages, 2014.
Jung et al., "Intron retention is a widespread mechanism of tumor-suppressor inactivation.", Nat Genet 47, 1242-1248, 2015.
Kalinich et al., "An RNA-based signature enables high specificity detection of circulating tumor cells in hepatocellular carcinoma.", Proc Natl Acad Sci USA, 114(5): 1123-1128, 2017.
Kandoth et al., "Integrated genomic characterization of endometrial carcinoma.", Nature 497, 67-73, 2013.
Kandoth et al., "Mutational landscape and significance across 12 major cancer types", Nature 502: 333-339, 2013.
Karow, "Hopkins Team Develops method to Improve Rare Mutation Detection for Early Cancer Dx," Genomeweb, 3 pages, Jun. 1, 2011.
Karst et al., "Modeling high-grade serous ovarian carcinogenesis from the fallopian tube", Proc. Natl Acad Sci USA 108, 7547-7552, 2011.
Kaufamn et al., "Olaparib monotherapy in patients with advanced cancer and a germline BRCA1/2 mutation.", J Clin. Oncol. 33: 244-250, 2015.
Kawauchi et al., "9p21 index as estimated by dual-color fluorescence in situ hybridization is useful to predict urothelial carcinoma recurrence in bladder washing cytology.", Hum Pathol 40: 1783-1789, 2009.
Kennedy et al., "Detecting ultralow-frequency mutations by Duplex Sequencing.", Nature protocols 9, 2586-2606, 2014.
Kennedy et al., "Somatic mutations in aging, cancer and neurodegeneration", MechAgeing Dev 133: 118-126, 2012.
Keohavong et al., "Fidelity of DNA polymerases in DNA amplification.", Proc Natl Acad Sci US A 86: 9253-9257, 1989.
Kesmodel et al., "Gastrointestinal Cancers SymposiumSymposium: Multidisciplinary Approaches to the Prevention, Diagnosis, and Therapy of GI Cancers", abstr 234, 4 pages, 2007.
Keys et al., "Primer ID Informs Next-Generation Sequencing Platforms and Reveals Preexisting Drug Resistance Mutations in the HIV-1 Reverse Transcriptase Coding Domain.", AIDS Res Hum Retroviruses 31, 658-668, 2015.
Khadra et al., "A prospective analysis of 1,930 patients with hematuria to evaluate current diagnostic practice.", J Urol 163: 524-527, 2000.
Kidd et al., "Developing a SNP panel for forensic identification of individuals", Forensic science international 164: 20-32, 2006.
Killela et al., "TERT promoter mutations occur frequently in gliomas and a subset of tumors derived from cells with low rates of self-renewal.", Proc Natl Acad Sci USA 110:6021-6026, 2013.
Kim et al., "Clinical usefulness of carbohydrate antigen 19-9 as a screening test for pancreatic cancer in an asymptomatic population,", J Gastroenterol Hepatol 19(2): 182-186, 2004.
Kim et al., "Oligonucleotide microarray analysis of distinct gene expression patterns in colorectal cancer tissues harboring BRAF and K-ras mutations.", Carcinogenesis 27(3): 392-404, 2006.
Kinde et al., "Detection and quantification of rare mutations with massively parallel sequencing", Proceedings of the National Academy of Sciences of the United States of America 108, 9530-9535, 2011.
Kinde et al., "FAST-SeqS: a simple and efficient method for the detection of aneuploidy by massively parallel sequencing,", PloS ONE 7:e41162, 2012.
Kinde et al., "TERT promoter mutations occur early in urothelial neoplasia and are biomarkers of early disease and disease recurrence in urine.", Cancer Res 73 :7162-7167, 2013.
Kivioja et al., "Counting absolute numbers of molecules using unique molecular identifiers," Nature Methods, vol. 9, No. 1, pp. 72-74, 2012.
Kobayashi et al., "A randomized study of screening for ovarian cancer: a multi center study in Japan,", Int J Gynecol Cancer 18, 414-420, 2008.
Konecny et al., "Activity of the Dual Kinase Inhibitor Lapatinib (GW572016) against HER-2-Overexpressing and Trastuzumab-Treated Breast Cancer Cells", Cancer Res 66: 1630-1639, 2006.
Koopmann et al., "Evaluation of Osteopontin as Biomarker for Pancreatic Adenocarcinoma", Cancer Epidemiol Biomarkers Prev 13(3): 487-491, 2004.
Korpanty et al., "Biomarkers that currently affect clinical practice in lung cancer: EGFR, ALK, MET, ROS-1, and KRAS", Front Oncol. 4: 204, 2014.

(56) References Cited

OTHER PUBLICATIONS

Kosuri et al., "Scalable gene synthesis by selective amplification of DNA pools from high-fidelity microchips.", Nat Biotechnol 28: 1295-1299, 2010.
Kou et al., "Benefits and Challenges with Applying Unique Molecular Identifiers in Next Generation Sequencing to Detect Low Frequency Mutations", PLOS ONE., vol. 11, No. 1, p. e0146638, 2016.
Kozarewa et al., "Amplification-free Illumina sequencing-library preparation facilitates improved mapping and assembly of (G+C)-biased genomes", Nature Methods, vol. 6, No. 4, pp. 291-295, 2009.
Kozarewa et al., "Amplification-free library preparation for paired-end illumina sequencing", chapter 18, pp. 257-266, 2011.
Kraystberg et al.,"Single-molecuke PCR: an artifact-free PCR approach for the analysis of somatic mutations" Expert Rev. Mol. Diagn. 5(5), 809-815, 2005.
Kraystberg et al.,"Single molecule PCR in mtDNA mutational analysis: genuine mutations vs. damage bypass-derived arttifacts" NIH Public Access Methods, 46(4): 269-273, 2008.
Krimmel et al., "Ultra-deep sequencing detects ovarian cancer cells in peritoneal fluid and reveals somatic TP53 mutations in noncancerous tissues.", Proc Natl Acad Sci USA 113, 6005-6010, 2016.
Kruger et al., "Numerical aberrations of chromosome 17 and the 9p2 1 locus are independent predictors of tumor recurrence in noninvasive transitional cell carcinoma of the urinary bladder.", Int J Oncol 23 :41-48, 2003.
Kumar et al., "Application of microarray in breast cancer: An overview", J. Pharm. Bioallied Sci. 4(1): 21-26, 2012.
Kumar et al., "Association of mitochondrial copy number variation and T16189C polymorphism with colorectal cancer in North Indian population.", Tumour Biol, 39: 1010428317740296, 2017.
Kumar et al., "Cell-free mitochondrial DNA copy number variation in head and neck squamous cell carcinoma: A study of non-invasive biomarker from Northeast India.", Tumour Biol., 39: 1010428317736643, 2017.
Kumar et al., "Deep sequencing of multiple regions of glial tumors reveals spatial heterogeneity for mutations in clinically relevant genes.", Genome biology 15, 530, 2014.
Kumar et al., "Serum and Plasma Metabolomic Biomarkers for Lung Cancer", Bioinformation, 13(6); 202-208, 2017.
Kunkel, "The mutational specificity of DNA polymerase-beta during in vitro DNA synthesis.", J Biol Chem 260: 5787-5796, 1985.
Kuppusamy et al., "Proteins are potent biomarkers to detect colon cancer progression", Saudi Journal of Biological Sciences, 24, 1212-1221, 2017.
Kurman et al., "The Dualistic Model of Ovarian Carcinogenesis: Revisited, Revised, and Expanded.", Am J Pathol 186, 733-747, 2016.
Laddha et al., "Mutational Landscape of the Essential Autophagy Gene BECN1 in Human Cancers", Molecular cancer research 12: 485-490, 2014.
Laere et al., "cDNA Microarray Analysis of Inflammatory Breast Cancer Signatures", Methods Mol. Biol. 512: 71-98, 2009.
Lai et al., "Population-Based Case—Control Study of Chinese Herbal Products Containing Aristolochic Acid and Urinary Tract Cancer Risk", J Natl Cancer Inst, 102(3): 179-186, 2010.
Lalkhen et al., "Clinical tests: sensitivity and specificity", Continuing Education in Anaesthesia, Critical Care & Pain, vol. 8, No. 6, 221-223, 2008.
Langmead et al., "Fast gapped-read alignment with Bowtie 2", Nature Methods 9: 357-359, 2012.
Lee et al., "Quantification of kinase activity in cell lysates via photopatterned macroporous poly(ethylene glycol) hydrogel arrays in microfluidic channels", Biomed. Microdevices 14: 247-57, 2012.
Lennon et al., "Diagnostic and Therapeutic Response Markers.", Pancreatic Cancer, (Springer New York, New York, NY), pp. 675-701, 2010.
Lennon et al., "The Early Detection of Pancreatic Cancer: What Will It Take to Diagnose and Treat Curable Pancreatic Neoplasia?", Cancer Res 74(13): 3381-3389, 2014.
Levey et al., "Definition and classification of chronic kidney disease: a position statement from Kidney Disease: Improving Global Outcomes (KDIGO).", Kidney Int. 67(6): 2089-100, 2005.
Levey et al., "Using Standardized Seram Creatinine Values in the Modification of Diet in Renal Disease Study Equation for Estimating Glomerular Filtration Rate", Ann Intern Med. 145(4): 247-54, 2006.
Levina et al., "Biological significance of prolactin in gynecologic cancers.",Cancer Res 69(12): 5226-5233, 2009.
Li et al., "DNA Methylation in Peripheral Blood: A Potential Biomarker for Cancer Molecular Epidemiology", J. Epidemoil, 22(5): 384-394, 2012.
Li et al., "Replacing PCR with COLD-PCR enriches variant DNA sequences and redefines the sensitivity of genetic testing", Nat Med 14: 579-584, 2008.
Li et al., "Significant Predictive Factors for Prognosis of Primary Upper Urinary Tract Cancer after Radical Nephroureterectomy in Taiwanese Patients", Eur Ural. 54(5): 1127-1134, 2008.
Li et al., "Toward better understanding of artifacts in variant calling from high-coverage samples.", Bioinformatics 30: 2843-2851, 2014.
Liaw et al., "Classification and Regression by random Forest", R news 2: 18-22, 2001.
Lin et al., "A molecular inversion probe assay for detecting alternative splicing", BMC Genomics 11: 712, 2010.
Lin et al., "Benefits and harms of prostate-specific antigen screening for prostate cancer: an evidence update for the U.S. Preventive Services Task Force.", Ann. Intern. Med. 149: 192-199, 2008.
Lin et al., "Increase sensitivity in detecting superficial, low grade bladder cancer by combination analysis of hypermethylation of E-cadherin, p16, p14, RASSF1A genes in urine.", Ural Oncol 28: 597-602, 2010.
Linnarsson et al., "Recent advances in DNA sequencing methods—general principles of sample preparation", Experimental cell research., 316, 1339-1343, 2010.
Liotta et al., "The promise of proteomics.", Clin Adv Hematol Oncol 1(8): 460-462, 2003.
Lisca et al., "Prognostic significance of loss of heterozygosity at loci on chromosome 17p13.3-ter in sporadic breast cancer is evidence for a putative tumour suppressor gene", British Journal of Cancer, 80 (5/6) 821-826, 1999.
Liu et al., "Detection of extremely rare alleles by bidirectional pyrophosphorolysis-activated polymerization allele-specific amplification (Bi-PAP-A): measurement of mutation load in mammalian tissues.", Biotechniques 36: 156-166, 2004.
Liu et al., "Digital quantification of gene methylation in stool DNA by emulsion-PCR coupled with hydrogel immobilized bead-array.", Biosens Bioelectron 92: 596-601, 2017.
Livrahi et al., "PARP inhibitors in the management of breast cancer: current data and future prospects.", BMC Medicine 13: 188, 2015.
Locker et al., "ASCO 2006 Update of Recommendations for the Use of Tumor Markers in Gastrointestinal Cancer ", J. Clin. Oncol. 24: 5313-5327, 2006.
Lodato et al., "Somatic mutation in single human neurons tracks developmental and transcriptional history.", Science 350, 94-98, 2015.
Lodes et al., "Detection of Cancer with Serum miRNAs on an Oligonucleotide Microarray", PLoS One 4(7): e6229, 2009.
Lotan et al., "Sensitivity and Specificity of Commonly Available Bladder Tumor Markers Versus Cytology: Results of a Comprehensive Literature Review and Meta-Analyses", Urology 61: 109-18, 2003.
Lou et al., "Biomarkers for Hepatocellular Carcinoma", Biomark Cancer, 9: 1-9, 2017.
Louseberg et al., "Safety, Efficacy, and Patient Acceptability of Everolimus in the Treatment of Breast Cancer.", Breast Cancer 10: 239-252, 2017.
Lowe et al., "Multiplex Sensing of Protease and Kinase Enzyme Activity via Orthogonal Coupling of Quantum Dot-Peptide Conjugates", ACS nano, 6: 851-7, 2012.
Luria et al., "Mutations of Bacteria from Virus Sensitivity to Virus Resistance.", Genetics 28: 491-511, 1943.

(56) References Cited

OTHER PUBLICATIONS

Mackay et al., "cDNA microarray analysis of genes associated with ERBB2 (HER2/neu) overexpression in human mammary luminal epithelial cells", Oncogene 22: 2680-2688, 2003.
Mackay et al., "Phase II trial of the histone deacetylase inhibitor belinostat in women with platinum resistant epithelial ovarian cancer and micropapillary (LMP) ovarian tumours.", Eur. J. Cancer 46(9): 1573-1579, 2010.
Madabhushi et al., "DNA damage and its links to neurodegeneration.", Neuron 83, 266-282, 2014.
Makohon-Moore et al., "Limited heterogeneity of known driver gene mutations among the metastases of individual patients with pancreatic cancer", Nat Genet., 49(3): 358-366, 2017.
Mao et al., "The Application of Single Nucleotide Polymorphism Microarrays in Cancer Research", Curr. Genomics 8(4): 219-228, 2007.
Mao, "Recent advances in the molecular diagnosis of lung cancer.", Oncogene 21: 45, 6960-6969, 2002.
Maragh et al., "Evaluation of two mitochondrial DNA biomarkers for prostate cancer detection.", Cancer Biomark., 15: 763-73, 2015.
Matei et al., "Epigenetic Resensitization to Platinum in Ovarian Cancer", Cancer Res. 72(9): 2197-2205, 2012.
Matzas et al., "High-fidelity gene synthesis by retrieval of sequence-verified DNA identified using high-throughput pyrosequencing.", Nat Biotechnol 28: 1291-1294, 2010.
McCloskey et al., "Encoding PCR products with batch-stamps and barcodes", Biochem Genet 45: 761-767, 2007.
McMahon et al., "The HBV drug entecavir—effects on HIV-1 replication and resistance.", N Engl J Med 356: 2614-2621, 2007.
Meldrum et al., "Next-Generation Sequencing for Cancer Diagnostics: a Practical Perspective", Clin. Biochem. Rev. 32(4): 177-195, 2011.
Mendivil et al., "Increased incidence of severe gastrointestinal events with first-line paclitaxel, carboplatin, and vorinostat chemotherapy for advanced-stage epithelial ovarian, primary peritoneal, and fallopian tube cancer,", Int. J. Gynecol. Cancer 23(3): 533-539, 2013.
Menon et al., "Risk Algorithm Using Serial Biomarker Measurements Doubles the Number of Screen-Detected Cancers Compared With a Single-Threshold Rule in the United Kingdom Collaborative Trial of Ovarian Cancer Screening,", J Clin Oncol 33, 2062-2071, 2015.
Mermel et al., "GISTIC2.0 facilitates sensitive and confident localization of the targets of focal somatic copy-number alteration in human cancers", Genome biology 12: R41, 2011.
Metzker et al., "Sequencing technologies—the next generation" Nature reviews, 2010.
Michels et al., "Detection of DNA copy number alterations in cancer by array comparative genomic hybridization,", Genet. Med. 9: 574-584, 2007.
Miller et al., "Phase I trial of alvespimycin (KOS-1022; 17-DMAG) and trastuzumab (T)", J. Clin. Oncol. 25: s1 115, 2007.
Miner et al., "Molecular barcodes detect redundancy and contamination in hairpin-bisulfite PCR.", Nucleic Acids Res 32:el35, 2004.
Mirus et al., "Cross-Species Antibody Microarray Interrogation Identifies a 3-Protein Panel of Plasma Biomarkers for Early Diagnosis of Pancreas Cancer", Clin. Cancer Res. 21(7): 1764-1771, 2015.
Misek et al., "Protein Biomarkers for the Early Detection of Breast Cancer", International Journal of Proteomics, vol. 2011, article ID 343582, 9 pages, 2011.
Mishriki et al., "Diagnosis of urologic malignancies in patients with asymptomatic dipstick hematuria: prospective study with 13 years' follow-up.", Urology 71: 13-16, 2008.
Mitra et al., "Digital genotyping and haplotyping with polymerase colonies.", Proc Natl Acad Sci USA 100: 5926-5931, 2008.
Mizutani et al., "A Novel FRET-Based Biosensor for the Measurement of BCR-ABL Activity and Its Response to Drugs in Living Cells", Clin. Cancer Res. 16: 3964-75, 2010.
Mo et al., "Hyperactivation of Haras oncogene, but not Ink4a/Arf deficiency, triggers bladder tumorigenesis.", J Clin Invest 117: 314-325, 2007.
Moch et al., "The 2016 WHO Classification of Tumours of the Urinary System and Male Genital Organs—Part A: Renal, Penile, and Testicular Tumours", EAU, 70, 93-105, 2016.
Mockler et al., "Applications of DNA tiling arrays for whole-genome analysis", Genomics, 85(1): 1-15, 2005.
Modesitt et al., "A phase II study of vorinostat in the treatment of persistent or recurrent epithelial ovarian or primary peritoneal carcinoma: a Gynecologic Oncology Group study.", 109(2): 182-186, 2008.
Modi et al., "Phase II trial of the Hsp90 inhibitor tanespimycin (Tan) + trastuzumab (T) in patients (pts) with HER2-positive metastatic breast cancer (MBC)", J. Clin Oncol. 26: sl027, 2008.
Moertel et al., "Fluorouracil plus levamisole as effective adjuvant therapy after resection of stage III colon carcinoma: a final report.", Ann Intern Med 122(5): 321-326, 1995.
Monnat et al., "Nucleotide sequence preservation of human mitochondrial DNA", Proc Natl Acad Sci USA 82: 2895-2899, 1985.
Moonen et al., "UroVysion compared with cytology and quantitative cytology in the surveillance of non-muscle-invasive bladder cancer.", Eur Urol 51: 1275-80, 2007.
Moore et al., "The use of multiple novel tumor biomarkers for the detection of ovarian carcinoma in patients with a pelvic mass.", Gynecologic oncology 108, 402-408, 2008.
Moore et al., "Uterine Papillary Serous Carcinoma", Clin Obstet Gynecol 54: 278-291, 2011.
Moyer et al., "Screening for ovarian cancer: U.S. Preventive Services Task Force reaffirmation recommendation statement", Annals of internal medicine 157: 900-904, 2012.
Nair et al., "Genomic Analysis of Uterine Lavage Fluid Detects Early Endometrial Cancers and Reveals a Prevalent Landscape of Driver Mutations in Women without Histopathologic Evidence of Cancer: A Prospective Cross-Sectional Study", PLoS Med 13: e1002206, 2016.
National Toxicology Program, Aristolochic acids. Rep Carcinog, 12, 45-49, 2011.
Nazarian et al., "Melanomas acquire resistance to B-RAF(V600E) inhibition by RTK or N-RAS upregulation.", Nature 468: 973-977, 2010.
Nazli et al.," The diagnostic importance of CEA and CA 19-9 for the early diagnosis of pancreatic carcinoma.", Hepatogastroenterology 47(36): 1750-1752, 2000.
Netto et al., "Emerging Bladder Cancer Biomarkers and Targets of Therapy.", Urol Clin North Am 43:63-76, 2016.
Netto et al., "Theranostic and prognostic biomarkers: genomic applications in urological malignancies", Pathology 42: 384-394, 2010.
Netto, "Clinical applications ofrecent molecular advances in urologic malignancies: no longer chasing a "mirage"?.", Adv Anat Pathol 20: 175-203, 2013.
Netto, "Molecular biomarkers in urothelial carcinoma of the bladder: are we there yet?.", Nat Rev Urol 9: 41-51, 2011.
Ng et al., "Significance of endometrial cells in the detection of endometrial carcinoma and its precursors.", Acta cytologica 18, 356-361, 1974.
Ngan et al., "Abnormal expression and mutation of p53 in cervical cancer—a study at protein, RNA and DNA levels", Denitourin Med, 73: 54-58, 1997.
Nguyen et al., "High prevalence of TERT promoter mutations in micropapillary urothelial carcinoma.", Virchows Arch 469: 427-434, 2016.
Nolen et al., "Protein biomarkers of ovarian cancer: the forest and the trees", Future Oncol., 8(1): 55-71, 2012.
Non-Final Office Action issued in related U.S. Appl. No. 14/111,715, dated Oct. 15, 2015.
Non-Final Office Action issued in related U.S. Appl. No. 15/240,034, dated Dec. 23, 2016.
Non-Final Office Action issued in related U.S. Appl. No. 15/240,034, dated May 4, 2017.

(56) References Cited

OTHER PUBLICATIONS

Notice of Opposition in European Application No. 12772013.4, dated Jan. 11, 2018, 7 pages.
Notice of Opposition in European Application No. 12772013.4, dated Jan. 2, 2018, 22 pages.
Notice of Opposition in European Application No. 12772013.4, dated Jan. 9, 2018, 8 pages.
O'Brien et al., "Serum CA19-9 is significantly upregulated up to 2 years before diagnosis with pancreatic cancer: implications for early disease detection,", Clin Cancer Res 21(3): 622-631, 2015.
Odunsi et al., "Epigenetic potentiation of NY-ESO-1 vaccine therapy in human ovarian cancer", Cancer Immunol. Res. 2(1): 37-49, 2014.
Ogiwara et al., "Unbalanced translocation, a major chromosome alteration causing loss of heterozygosity in human lung cancer.", Oncogene, 27: 4788-97, 2008.
Ottesen et al., "Microfluidic digital PCR enables multigene analysis of individual environmental bacteria.", Science 314: 1464-1467, 2006.
Paik et al., "A Multigene Assay to Predict Recurrence of Tamoxifen-Treated, Node-Negative Breast Cancer", N. Engl. J. Med. 351: 2817-2826, 2004.
Parameswaran et al., "A pyrosequencing-tailored nucleotide barcode design unveils opportunities for large-scale sample multiplexing.", Nucleic Acids Res 35: e130, 2007.
Pardall, "The blockade of immune checkpoints in cancer immunotherapy", Nat. Rev Cancer 12: 252-264, 2012.
Park et al., "Large-scale clinical validation of biomarkers for pancreatic cancer using a mass spectrometry-based proteomics approach", Oncotarget, 8(26): 42761-42771, 2017.
Parsons et al., "Mismatch repair deficiency in phenotypically normal human cells", Science 268: 738-740, 1995.
Patz et al., "Panel of semm biomarkers for the diagnosis of lung cancer.", J Clin Oneal 25: 5578-5583, 2007.
Pengelly et al., "A SNP profiling panel for sample tracking in whole-exome sequencing studies", Genome medicine 5: 89, 2013.
Phallen et al., "Direct detection of early-stage cancers using circulating tumor DNA.", Science translational medicine 9, 2017.
Philips et al., "Targeting HER2-positive breast cancer with trastuzumab-DM1, an antibody-cytotoxic drug conjugate.", Cancer Res 68: 9280-9290, 2008.
Piccart-Gebhart et al., "Trastuzumab after adjuvant chemotherapy in HER2-positive breast cancer.", N. Engl. J. Med. 353: 1659-1672, 2005.
Pinkel et al., "Array comparative genomic hybridization and its applications in cancer", Nature Genetics, vol. 37, S11-S17, 2005.
Pinkel et al., "Summaries of Affymetrix GeneChip probe level data", Nat. Genetics 37:S11-S17, 2005.
Pinsky et al., "Prostate Cancer Screening—A Perspective on the Current State of the Evidence", The New England Journal of Medicine, 376; 13, 1285-1289, 2017.
Powers et al., "Protein analytical assays for diagnosing, monitoring, and choosing treatment for cancer patients.", J. Heathc Eng. 3(4): 503-534, 2015.
Proctor et al., "The promise of telomere length, telomerase activity and its regulation in the translocation-dependent cancer ESFT; clinical challenges and utility", Biochimica et Biophysica Acta, 260-274, 2009.
Quail et al., "A large genome center's improvements to the Illumina sequencing system.", Nat Methods 5:1005-1010, 2008.
Quail et al., "Improved Protocols for the Illumina Genome Analyzer Sequencing System," Current Protocols in Humar Genetics, Supplement 62, pp. 18.2.1-18.2.27, 2009.
Rahib et al., "Projecting Cancer Incidence and Deaths to 2030: The Unexpected Burden of Thyroid, Liver, and Pancreas Cancers in the United States", Cancer research 74, 2913-2921, 2014.
Ralla et al., "Nucleic acid-based biomarkers in body fluids of patients with urologic malignancies", Crit Rev Clin Lab Sci 51: 200-231, 2014.
Randerath et al., "Covalent DNA Damage in Tissues of Cigarette Smokers as Determined by 32P-Postlabeling Assay", Journal of the National Cancer Institute 81: 341-347, 1989.
Resta et al., "Phase I study of enzastaurin (ENZ) and bevacizumab (BV) in patients with advanced cancer", J. Clin. Oncol. 26 (May 20 suppl), abstr 3529, 2008.
Ricciuti et al., "Long-Lasting Response to Nivolumab and Immune-Related Adverse Events in a Nonsquamous Metastatic Non-Small Cell Lung Cancer Patient.", J. Thome Oncol. 12(5): e51-e55, 2017.
Roach et al., "Analysis of Genetic Inheritance in a Family Quartet by Whole Genome Sequencing", Science 328: 636-639, 2010.
Rodriguez et al., Spectrum of genetic mutations in de novo PUNLMP of the urinary bladder. Virchows Arch, vol. 471, issue 6, pp. 761-767, 2017.
Romond et al., "Trastuzumab plus Adjuvant Chemotherapy for Operable HER2-Positive Breast Cancer", N. Engl. J. Med. 353: 1673-1684, 2005.
Rosen et al., "Safety, pharmacokinetics, and efficacy of AMG 706, an oral multikinase inhibitor, in patients with advanced solid tumors.", J. Clin. Oncol. 25: 2369-76, 2007.
Rosenberg et al., "Adoptive cell transfer as personalized immunotherapy for human cancer", Science 348(6230): 62-68, 2015.
Rougemont et al., "Probabilistic base calling of Solexa sequencing data.", BMC Bioinformatics 9:431, 2008.
Roupret et al., "European Association of Urology Guidelines on Upper Urinary Tract Urothelial Cell Carcinoma: 2015 Update", Eur Ural. 68(5): 868-79, 2015.
Ryan et al., "Pancreatic adenocarcinoma.", N Engl J Med 371(22): 2140-2141, 2014.
Saltz et al., "Phase II Trial of Sunitinib in Patients With Metastatic Colorectal Cancer After Failure of Standard Therapy", J. Clin. Oncol. 25: 4793-4799, 2007.
Sandhu et al., "The poly(ADP-ribose) polymerase inhibitor niraparib (MK4827) in BRCA mutation carriers and patients with sporadic cancer: a phase 1 dose-escalation trial.", Lancet Oncol 14: 882-92, 2013.
Saraswat et al., "Comparative proteomic profiling of the serum differentiates pancreatic cancer from chronic pancreatitis", Cancer Med., vol. 6, issue 7, 1738-1751, 2017.
Sarkis et al., "Association of P53 nuclear overexpression and tumor progression in carcinoma in situ of the bladder.", J Urol 152: 388-392, 1994.
Sarkis et al., "Nuclear overexpression ofp53 protein in transitional cell bladder carcinoma: a marker for disease progression,", J Natl Cancer Inst 85:53-59, 1993.
Sarkis et al., "Prognostic value of p53 nuclear overexpression in patients with invasive bladder cancer treated with neoadjuvant MVAC.", J Clin Oncol 13: 1384-1390, 1995.
Sarojini et al., "Early Detection Biomarkers for Ovarian Cancer", J. Oncol. 2012: 709049, 2012.
Sarosdy et al., "Use of a multitarget fluorescence in situ hybridization assay to diagnose bladder cancer in patients with hematuria.", J Urol 176: 44-47, 2006.
Schmidt et al., "Pre-diagnostic metabolite concentrations and prostate cancer risk in 1077 cases and 1077 matched controls in the European Prospective Investigation into Cancer and Nutrition", BMC Med, 15: 122, 14 pages, 2012.
Schmitt et al., "Detection of ultra-rare mutations by next-generation sequencing", PNAS USA 109:14508-14513, 2012.
Schnatz et al., "Clinical significance of atypical glandular cells on cervical cytology.", Obstetrics and gynecology 107, 701-708, 2006.
Schroder et al., "Dual-color Proteomic Profiling of Complex Samples with a Microarray of 810 Cancer-related Antibodies",Mol. Cell. Proteomics 9: 1271-80, 2010.
Schulz et al., "Inhibiting the HSP90 chaperone destabilizes macrophage migration inhibitory factor and thereby inhibits breast tumor progression.", J Exp Med 209(2): 275-89, 2012.
Schwienbacher et al., "Abnormal RNA expression of 11p15 imprinted genes and kidney developmental genes in Wilms' tumor,", Cancer Res., 60: 1521-5, 2000.
Scott et al., "Mutations of the TERT promoter are common in basal cell carcinoma and squamous cell carcinoma.", Mod Pathol 27: 516-523, 2014.

(56) References Cited

OTHER PUBLICATIONS

Scott, "Niraparib: First Global Approval", Drugs, 77: 1029-1034, 2017.
Semrad et al., "Integrating Chemotherapy into the Management of Oligometastatic Colorectal Cancer: Evidence-Based Approach Using Clinical Trial Findings.", Ann Surg Oncol 22(Suppl 3): S855-862, 2015.
Serizawa et al., "Integrated genetic and epigenetic analysis of bladder cancer reveals an additive diagnostic value of FGFR3 mutations and hypermethylation events.", Int J Cancer 129(1):78-87, 2010.
Sethi et al., "Evolving Concept of Cancer Stem Cells: Role of Micro-RNAs and their Implications in Tumor Aggressiveness", J. Carcinog. Mutag. S 1-005, 2011.
Shariat et al., "Gender differences in radical nephroureterectomy for upper tract urothelial carcinoma", World J Ural. 29(4): 481-486, 2011.
Sharma et al., "Risk of epithelial ovarian cancer in asymptomatic women with ultrasound-detected ovarian masses: a prospective cohort study within the UK collaborative trial of ovarian cancer screening (UKCTOCS)", Ultrasound Obstet Gynecol 40: 338-344, 2012.
Shen et al., "BMN 673, a novel and highly potent PARP1/2 inhibitor for the treatment of human cancers with DNA repair deficiency.", Clin. Cancer Res. 19(18): 5003-5015, 2013.
Shen et al., "Mitochondrial copy number and risk of breast cancer: A pilot study", Mitochondrion, 10: 62-68, 2010.
Shi et al., "A Novel Proximity Assay for the Detection of Proteins and Protein Complexes: Quantitation of HER1 and HER2 Total Protein Expression and Homodimerization in Formalin-fixed, Paraffin-Embedded Cell Lines and Breast Cancer Tissue", Diagnostic molecular pathology: the American journal of surgical pathology, part B: 18: 11-21, 2009.
Shi et al., "LigAmp for sensitive detection of single-nucleotide differences.", Nat Methods 1: 141-147, 2007.
Shibata, "Mutation and epigenetic molecular clocks in cancer,", Carcinogenesis 32: 123-128, 2011.
Shlien et al., "Combined hereditary and somatic mutations of replication error repair genes result in rapid onset of ultra-hypermutated cancers.", Nature genetics 47: 257-262, 2015.
Sidranksy, "Nucleic acid-based methods for the detection of cancer.", Science 278(5340): 1054-9, 1997.
Sidransky et al., Identification of p53 gene mutations in bladder cancers and urine samples. Science 252: 706-709, 1991.
Siegel et al., "Cancer Statistics, 2017.", CA Cancer J Clin 67: 7-30, 2017.
Siravegna et al., "Integrating liquid biopsies into the management of cancer.", Nat Rev Clin Oncol 14, 531-548, 2017.
Skacel et al., "Multitarget Fluorescence In Situ Hybridization Assay Detects Transitional Cell Carcinoma in the Majority of Patients with Bladder Cancer and Atypical or Negative Urine Cytology", J Urol 169: 2101-2105, 2003.
Smith et al., "Epigenetic therapy for the treatment of epithelial ovarian cancer: A clinical review", Gynecol. Oncol. Rep. 20: 81-86, 2017.
Somlo et al., "Efficacy of the combination of ABT-888 (veliparib) and carboplatin in patients with BRCA-associated breast cancer.", J. Clin. Oncol. 31: 1024, 2013.
Song et al., "Prognostic factors in women with synchronous endometrial and ovarian cancers.", Int J Gynecol Cancer 24: 520-527, 2014.
Soria et al., "Epidemiology, diagnosis, preoperative evaluation and prognostic assessment of upper-tract urothelial carcinoma (UTUC)", World J Urol, 35(3), 379-387, 2017.
Sorscher, "Pembrolizumab in Non-Small-Cell Lung Cancer,", N Engl J Med 376, 10: 996-7, 2017.
Soung et al., "Exosomes in Cancer Diagnostics", Cancers 9(1):pii:E8, 2017.
Spalding et al., "Retrospective birth dating of cells in humans.", Cell 122, 133-143, 2005.
Springer et al., "A Combination of Molecular Markers and Clinical Features Improve the Classification of Pancreatic Cysts", Gastroenterology 149(6): 1501-1510, 2015.
Springer et al., "Non-invasive detection of urothelial cancer through the analysis of driver gene mutations and aneuploidy", eLIFE, 7: e32143, 27 pages, 2018.
Steensma et al., "Clonal hematopoiesis of indeterminate potential and its distinction from myelodysplastic syndromes.", Blood 126, 9-16, 2015.
Stem et al., "Mutation of the TERT promoter, switch to active chromatin, and monoallelic TERT expression in multiple cancers.", Genes Dev 29: 2219-2224, 2015.
Stratagene Catalog, p. 39, 1988.
Stratton et al., "The cancer genome.", Nature 458: 719-724, 2009.
Stromberg et al., "A high-throughput strategy for protein profiling in cell microarrays using automated image analysis.", Proteomics 7: 2142-50, 2007.
Sun et al., "Elevated expression of the centromere protein-A(CENP-A)-encoding gene as a prognostic and predictive biomarker in human cancers", Int. J. Cancer, 139, 899-907, 2016.
Sun et al., "Nivolumab effectively inhibit platinum-resistant ovarian cancer cells via induction of cell apoptosis and inhibition of ADAM17 expression", Eur Rev Med Pharmacol Sci 21(6): 1198-1205, 2017.
Tabernero et al., "Phase I study of AZD0530, an oral potent inhibitor of Src kinase: First demonstration of inhibition of Src activity in human cancers", J. Clin. Oncol. 25: 18S, abstr 3520, 2007.
Takahashi et al., "Clonal and chronological genetic analysis of multifocal cancers of the bladder and upper urinary tract.", Cancer Res 58: 5835-5841, 1998.
Tanase et al., "Prostate cancer proteomics: Current trends and future perspectives for biomarker discovery", Oncotarget., Mar. 14; 8(11): 18497-18512, 2017.
Tang et al., "A phase I study of vorinostat (VOR) in combination with capecitabine (CAP) in patients (pts) with advanced solid tumors", J. Clin. Oncol 26, May 20 suppl; abstr 4027, 2018.
Tao, "Direct intrauterine sampling: the IUMC Endometrial Sampler.", Diagnostic cytopathology 17, 153-159, 1997.
The 1000 Genomes Project Consortium, "An integrated map of genetic variation from 1,092 human genomes.", Nature 491: 56-65, 2012.
Thomas et al., "Construction of a 2-Mb resolution BAC microarray for CGH analysis of canine tumors", Genome Res. 15(12): 1831-1837, 2005.
Thomas et al., "Evaluation of semm CEA, CYFRA21-1 and CA125 for the early detection of colorectal cancer using longitudinal preclinical samples.", Br J Cancer 113(2): 268-274, 2015.
Thompson et al., "Winnowing DNA for Rare Sequences: Highly Specific Sequence and Methylation Based Enrichment", PLoS ONE, 7:e31597, 2012.
Thorpe et al., "Effects of blood collection conditions on ovarian cancer semm markers.", PLoS One 2(12): e1281, 2007.
Thunnissen, "Sputum examination for early detection of lung cancer.", J Clin Pathol 56: 805-810, 2003.
Thyagarajan et al., "Mitochondrial Copy Number is Associated With Colorectal Cancer Risk", Cancer Epidemiol Biomarkers Prev, 21(9): 1574-1581, 2012.
Tindall et al., "Fidelity of DNA synthesis by the Thermus aquaticus DNA polymerase.", Biochemistiy 27: 6008-6013, 1988.
Tomasetti et al., "Cancer etiology. Variation in cancer risk among tissues can be explained by the number of stem cell divisions.", Science 347, 78-81, 2015.
Tomasetti et al., "Half or more of the somatic mutations in cancers of self-renewing tissues originate prior to tumor initiation.", Proceedings of the National Academy of Sciences of the United States of America 110, 1999-2004, 2013.
Tsuchiya et al., "Biomarkers for the early diagnosis of hepatocellular carcinoma", World J Gastroenterol., 21(37): 10573-10583, 2015.
Tsuchiya et al., "Collective review of small carcinomas of the pancreas.", Ann Surg 203(1): 77-81, 1986.
Turner et al., "Palbociclib in Hormone-Receptor-Positive Advanced Breast Cancer", N Engl J Med 373:209-219, 2015.

(56) References Cited

OTHER PUBLICATIONS

Tutt et al., "Oral poly(ADP-ribose) polymerase inhibitor olaparib in patients with BRCA1 or BRCA2 mutations and advanced breast cancer: a proof-of-concept trial", Lancet 376: 235-44, 2010.
Uhlen et al., "Tissue-based map of the human proteome.", Science 347(6220): 1260419, 2015.
Vallania et al., High-throughput discovery of rare insertions and deletions in large cohorts. Genome Res 20: 1711-1718, 2010.
Van Beers et al., "Array-CGH and breast cancer", Breast Cancer Res. 8(3): 210, 10 pages, 2006.
Van Dongen et al., "Analysis of immunoglobulin and T cell receptor genes. Part II: Possibilities and limitations in the diagnosis and management of lymphoproliferative diseases and related disorders.", Clin Chim Acta 198: 93-174, 1991.
Vansteenkiste et al., "Prospects and progress of atezolizumab in non-small cell lung cancer", Expert Opin Biol Ther 17(6): 781-789, 2017.
Vijg et al., "Somatic mutations, genome mosaicism, cancer and aging", Current opinion in genetics & development 26: 141-149, 2014.
Vogelstein et al., "Digital PCR.", Proc NatlAcad Sci US A 96: 9236-9241, 1999.
Vogelstein et al., "The Path to Cancer—Three Strikes and You're Out", N Engl J Med 3 73: 1895-1898, 2015.
Waddell et al., "Whole genomes redefine the mutational landscape of pancreatic cancer", Nature 518(7540):495-501, 2015.
Walsh et al., Coexisting ovarian malignancy in young women with endometrial cancer. Obstetrics and gynecology 106, 693-699, 2005.
Wang et al., "Detection of somatic mutations and HPV in the saliva and plasma of patients with head and neck squamous cell carcinomas.", Science translational medicine 7(293): 293ra104, 2015.
Wang et al., "Detection of tumor-derived DNA in cerebrospinal fluid of patients with primary tumors of the brain and spinal cord.", Proc Natl Acad Sci USA 1 12(31): 9704-9709, 2015.
Wang et al., "Diagnostic potential of tumor DNA from ovarian cyst fluid.", Elife 5, 18 pages, 2016.
Wang et al., "Diagnostic significance of urinary long non-coding PCA3 RNA in prostate cancer", Oncotarget, vol. 8, No. 35, 58577-58586, 2017.
Wang et al., "Evaluation of liquid from the Papanicolaou test and other liquid biopsies for the detection of endometrial and ovarian cancers", Sci. Transl. Med., 10, eaap8796, 9 pages, 2018.
Wang et al., "Extracellular interactions and ligand degradation shape the nodal morphogen gradient", Elife 5: 10.7554/eLife.15 175, 19 pages, 2016.
Wang et al., "Molecular inversion probes: a novel microarray technology and its application in cancer research.", Cancer Genet 205(7-8): 341-55, 2012.
Wang et al., "Molecular mechanisms and clinical applications of miR-22 in regulating malignant progression in human cancer (Review)", International Journal of Oncology, 50: 345-355, 2017.
Wang et al., "PD-L1 and intratumoral immune response in breast cancer", Oncotarget, vol. 8, (No. 31), pp. 51641-51651, 2017.
Wang et al., "TERT promoter mutations are associated with distant metastases in upper tract urothelial carcinomas and serve as urinary biomarkers detected by a sensitive castPCR.", Oncotarget, 5: 12428-12439, 2014.
Wang et al., "The clinical impact of recent advances in LC-MS for cancer biomarker discovery and verification", Expert Rev Proteomics 13: 99-114, 2016.
Wang et al., "The long non-coding RNA CYTOR drives colorectal cancer progression by interacting with NCL and Sam68", Molecular Cancer, 17: 110, 16 pages, 2018.
Wei et al., "A study of the relationships between oligonucleotide properties and hybridization signal intensities from NimbleGen microarray datasets", Nucleic Acids Res 36(9): 2926-2938, 2008.
Wilcox et al., "Chronic pancreatitis pain pattern and severity are independent of abdominal imaging findings.", Clin Gastroenterol Hepatol 13(3):552-560; quiz e528-559, 2015.
Wong et al., "Chronic Pancreatitis Pain Pattern and Severity are Independent of Abdominal Imaging Findings", Clin. Cancer Res. 15: 2552-2558, 2009.
Woodbury et al., "Elevated HGF Levels in Sera from Breast Cancer Patients Detected Using a Protein Microarray ELISA", J. Proteome Res. 1: 233-237, 2002.
Wu et al., "Endometrial brush biopsy (Tao brush). Histologic diagnosis of 200 cases with complementary cytology: an accurate sampling technique for the detection of endometrial abnormalities.", American journal of clinical pathology 114, 412-418, 2000.
Wu, "Urothelial tumorigenesis: a tale of divergent pathways.", Nat Rev Cancer 5: 713-725, 2005.
Xia et al., "Lapatinib Antitumor Activity Is Not Dependent upon Phosphatase and Tensin Homologue Deleted on Chromosome 10 in ErbB2-Overexpressing Breast Cancers", Cancer Res. 67: 1170-1175, 2007.
Xie et al., "Age-related mutations associated with clonal hematopoietic expansion and malignancies.", Nat Med 20(12): 1472-1478, 2014.
Xie et al., "Lnc-PCDH9-13:1 Is a Hypersensitive and Specific Biomarker for Early Hepatocellular Carcinoma", EBioMedicine, 33, 57-67, 2018.
Xu et al., "Recent advances of highly selective CDK4/6 inhibitors in breast cancer", J Hematol. Oncol. 10(1): 97, 2017.
Yachida et al., "Clinical significance of the genetic landscape of pancreatic cancer and implications for identification of potential long-term survivors.", Clin Cancer Res 18: 6339-6347, 2012.
Yafi et al., "Prospective analysis of sensitivity and specificity of urinary cytology and other urinary biomarkers for bladder cancer.", Urol Oncol 33 :66.e25-66.e3 1, 2015.
Yang et al., "Unusually high incidence of upper urinary tract urothelial carcinoma in Taiwan.", Urology, 59( 5), 681-687, 2002.
Yee et al., "Personalized Therapy Tumor Antigen Discovery for Adoptive Cellular Therapy", Cancer J. 23(2): 144-148, 2016.
Young et al., "Clonal haematopoiesis harbouring AML-associated mutations is ubiquitous in healthy adults.", Nat Commun 7, 12484, 2016.
Yousem et al., "Pulmonary Langerhans Cell Histiocytosis. Profiling of Multifocal Tumors Using Next-Generation Sequencing Identifi es Concordant Occurrence of BRAF V600E Mutations", Chest 143: 1679-1684, 2013.
Yu et al., "LncRNA HCP5 promotes the development of cervical cancer by regulating MACC1 via suppression of microRNA-15a.", Eur. Rev. Med. Pharmacol. Sci., 22: 4812-4819, 2018.
Yu et al., "Long non-coding RNA CACNA1G-AS1 promotes cell migration, invasion and epithelial-mesenchymal transition by HNRNPA2B1 in non-small cell lung cancer", Eur. Rev. Med. Pharmacol. Sci., 22: 993-1002, 2018.
Yun et al., "Biomonitoring of aristolactam-DNA adducts in human tissues using ultra-performance liquid chromatography/ion-trap mass spectrometry.", Chem ResToxicol. 2012 25(5): 1119-31, 2012.
Zack et al., "Pan-cancer patterns of somatic copy number alteration. ", Nature genetics 45: 1134-1140, 2013.
Zaino et al., "Simultaneously Detected Endometrial and Ovarian Carcinomas—A Prospective Clinicopathologic Study of 74 Cases: A Gynecologic Oncology Group Study", Gynecologic oncology 83: 355-362, 2001.
Zamay et al., "Current and Prospective Protein Biomarkers of Lung Cancer", Cancers (Basel), 9(11): 155, 2017.
Zhai et al.,"High-grade serous carcinomas arise in the mouse oviduct via defects linked to the human disease.", The Journal of pathology 243, 16-25, 2017.
Zhang et al., "Analysis of the complex interaction of CDRlas-miRNA-protein and detection of its novel role in melanoma", Oncology Letters, 16: 1219-1225, 2018.
Zhang et al., "LncRNA DQ786243 expression as a biomarker for assessing prognosis in patients with gastric cancer.", Eur. Rev. Med. Pharmacol. Sci., 22: 2304-2309, 2018.
Zhang et al., "LncRNA H19 regulates the expression of its target gene HOXA10 in endometrial carcinoma through competing with miR-612.", Eur. Rev. Med. Pharmacol. Sci., 22: 4820-4827, 2018.
Zhang et al., "The cytomorphological features of low-grade urothelial neoplasms vary by specimen type.", Cancer Cytopathol 124: 552-564, 2016.

(56) References Cited

OTHER PUBLICATIONS

Zhao et al., "Histologic follow-up results in 662 patients with Pap test findings of atypical glandular cells: results from a large academic womens hospital laboratory employing sensitive screening methods.", Gynecologic oncology 114, 383-389, 2009.
Zhou et al., "Identifying markers for pancreatic cancer by gene expression analysis.", Cancer Epidemiol Biomarkers Prev 7(2): 109-112, 1998.
Zilbermann et al., "Genome-wide analysis of Dna methylation patterns" Development 134, 2007.
Zimmermann et al., "Digital PCR: a powerful new tool for noninvasive prenatal diagnosis?", Prenat Diagn 28: 1087-1093, 2008.
Zou et al., "More valuable than platinum: first-line pembrolizumab in advanced stage non-small-cell lung cancer.", Ann Oncol 28(4): 685-687, 2017.
Affymetrix Human Genome U133 Plus 2.0 Array, Public on Nov. 7, 2003, Gene Expression Omnibus URL: https://www.ncbi.nlm.nih.gov/geo/query/acc.cgi?acc=GPL570> [Retrieved from the internet Jun. 7, 2018].
Australian Office Action in Australian Application No. 2017203206, dated Jan. 23, 2018.
Bandiera et al., "Cancer antigen 125, human epididymis 4, kallikrein 6, osteopontin and soluble mesothelin-related peptide immunocomplexed with immunoglobulin Min epithelial ovarian cancer diagnosis.", Clinical chemistry and laboratoty medicine: CCLM I FESCC 51, 1815-1824, 2013.
Barollo et al., "Prevalence, tumorigenic role, and biochemical implications of rare BRAF alterations", Thyroid: offical journal of the american thyroid association 24, 809-819, 2014.
Bashashati et al., "Distinct evolutionary trajectories of primary high-grade serous ovarian cancers revealed through spatial mutational profiling.", The Journal of pathology, 231: 21-34, 2013.
Bast et al., "A radioimmunoassay using a monoclonal antibody to monitor the course of epithelial ovarian cancer", The New England journal of medicine 309, 883-887, 1983.
Bertotti et al., "The genomic landscape of response to EGFR blockade in colorectal cancer.", Nature, 526: 263-7, 2015.
Bowtell et al., "Rethinking ovarian cancer II: reducing mortality from high-grade serous ovarian cancer.", Nature reviews Cancer, 15: 668-79, 2015.
Buys et al., "Ovarian cancer screening in the Prostate, Lung, Colorectal and Ovarian (PLCO) cancer screening trial: findings from the initial screen of a randomized trial", American journal of obstetrics and gynecology 193, 1630-1639, 2005.
Cass et al., BRCA-mutation-associated fallopian tube carcinoma: a distinct clinical phenotype? Obstetrics and Gynecology 106: 1327-34, 2005.
Chang et al., "The clinical utility of endoscopic ultrasound-guided fine-needle aspiration in the diagnosis and staging of pancreatic carcinoma.", Gastrointestinal endoscopy 45, 387-393, 1997.
Cheng et al., "Molecular genetic analysis of ovarian serous cystadenomas", Laboratory investigation; a journal of technical methods and pathology 84, 778-784, 2004.
Christensen et al., "Functional ovarian cysts in premenopausal and gynecologically healthy women", Contraception 66, 153-157, 2002.
Cobb et al., "Adenocarcinoma of Mullerian origin: review of pathogenesis, molecular biology, and emerging treatment paradigms" Gynecologic Oncology Research and Practice, May 12, 2015 (online), vol. 5, pp. 1-16.
Conner et al., "Outcome of unexpected adnexal neoplasia discovered during risk reduction salpingo-oophorectomy in women with germ-line BRCA1 or BRCA2 mutations.", Gynecol Oncol 132: 280-6, 2014.
Cruz et al., "Absence of BRAF and NRAS mutations in uveal melanoma", Cancer research 63, 5761-5766, 2003.
Davies et al., "Mutations of the BRAF gene in human cancer", Nature 417, 949-954, 2002.
Demirol et al., "Effect of endometrioma cystectomy on IVF outcome: a prospective randomized study", Reproductive biomedicine online 12, 639-643, 2006.
Dinkelspiel et al., "Long-term mortality among women with epithelial ovarian cancer.", Gynecologic oncology 138: 421-8, 2015.
Duke et al., "Transvaginal aspiration of ovarian cysts: long-term follow-up", Cardiovascular and interventional radiology 29, 401-405, 2006.
Eberle et al., "Immunoguided laser assisted microdissection techniques for DNA methylation analysis of archival tissue specimens.", The Journal of molecular diagnostics: JMD 12: 394-401, 2010.
Eloubeidi et al., "Endoscopic ultrasound-guided fine needle aspiration biopsy of patients with suspected pancreatic cancer: diagnostic accuracy and acute and 30-day complications.", The American journal of gastroenterology 98, 2663-2668, 2003.
Falconer et al., "Ovarian cancer risk after salpingectomy: a nationwide population-based study.", J. Natl. Cancer Inst., 107,vol. 2, 2015.
Ferlay et al., "Cancer incidence and mortality patterns in Europe: estimates for 40 countries in 2012.", European Journal of cancer 49: 1374-403, 2013.
Frossard et al., "Performance of endosonography-guided fine needle aspiration and biopsy in the diagnosis of pancreatic cystic lesions", The american journal of gastroenterology 98, 1516-1524, 2003.
Grisham et al., "BRAF mutation is associated with early stage disease and improved outcome in patients with low-grade serous ovarian cancer", Cancer 119, 548-554, 2013.
"Haber et al., ""Blood-based analyses of cancer: circulating tumor cells and circulating tumor DNA,"", Cancer discoveiy 4: 650-61, 2014".
Havrilesky et al., "Predictors of clinical outcomes in the laparoscopic management of adnexal masses.", Obstetrics and gynecology 102, 243-251, 2003.
Hellstrom et al., "The HE4 (WFDC2) protein is a biomarker for ovarian carcinoma", Cancer research 63, 3695-3700, 2003.
Hilgeret et al., "Laparoscopic management of the adnexal mass.", Clinical obstetrics and gynecology 49, 535-548, 2006.
International Search Report and Written Opinion in International Application No. PCT/US2016/046453, dated Nov. 1, 2016, 11 pages.
Jacobs et al., "Ovarian cancer screening and mortality in the UK Collaborative Trial of Ovarian Cancer Screening UKCTOCS): a randomised controlled trial.", Lancet 387: 945-956, 2016.
"Jones et al., ""Comparative lesion sequencing provides insights into tumor evolution."", Proceedings of the National Academy of Sciences of the United States of America 105: 4283-8, 2008".
Jones et al., "Low-grade serous carcinomas of the ovary contain very few point mutations", The Journal of pathology 226, 413-420, 2012.
Jones et al., "Personalized genomic analyses for cancer mutation discovery and interpretation.", Science translational medicine, 7: 283ra53, 2015.
Karst et al., "Ovarian cancer pathogenesis: a model in evolution.", Journal of oncology 932371, 13 pages, 2010.
Kauff et al., "Risk-reducing salpingooophorectomy in women with a BRCA1 or BRCA2 mutation.", The New England journal of medicine, 346: 1609-15, 2002.
Kim et al., "Impact of intraoperative rupture of the ovarian capsule on prognosis in patients with early-stage epithelial ovarian cancer: a meta-analysis.", European journal of surgical oncology : the journal of the European Society of Surgical Oncology and the British Association of Surgical Oncology 39, 279-289, 2013.
Kindelberger et al., "Intraepithelial carcinoma of the fimbria and pelvic serous carcinoma: Evidence for a causal relationship.", The American journal of surgical pathology 31: 161-9, 2007.
Kristjansdottir et al., "Ovarian cyst fluid is a rich proteome resource for detection of new tumor biomarkers", Clinical Proteomics, vol. 9, internal pp. 1-9, 2012.
Kristjansdottir et al., "Potential tumor biomarkers identified in ovarian cyst fluid by quantitative proteomic analysis, iTRAQ.", Clinical proteomics 10, 4, 2013.
"Kuhn et al., ""TP53 mutations in serous tubal intraepithelial carcinoma and concurrent pelvic high-grade serous carcinoma-evidence supporting the clonal relationship of the two lesions."", The Journal of pathology, 226:421-6, 2012".

(56) References Cited

OTHER PUBLICATIONS

Kurman et al., "The origin and pathogenesis of epithelial ovarian cancer: a proposed unifying theory", The American journal of surgical pathology 34,433-443, 2010.
Kwon et al., "Prophylactic salpingectomy and delayed pophorectomy as an alternative for BRCA mutation carriers.", Obstetrics and gynecology, 121:14-24, 2013.
Lee et al., "A candidate precursor to serous carcinoma that originates in the distal fallopian tube", The journal of pathology 211, 26-35, 2007.
Levanon et al., "New insights into the pathogenesis of serous ovarian cancer and its clinical impact.", Journal of clinical oncology : official journal of the American Society of Clinical Oncology, 26: 5284-93, 2008.
Levine et al., "Management of asymptomatic pvarian and other adnexal cysts imaged at US: Society of Radiologists in Ultrasound Consensus Conference Statement", Radiology 256, 943-954, 2010.
Lin et al., "Thyroid cancer in the thyroid nodules evaluated by ultrasonography and fine-needle aspiration cytology", Thyroid: official journal of the american thyroid association 15, 708-717, 2005.
Loh et al., "Ovarian response after laparoscopic ovarian cystectomy for endometriotic cysts in 132 monitored cycles", Fertility and sterility 72, 316-321, 1999.
Longacre et al., "Recommendations for the reporting of fallopian tube neoplasms.", Hum Pathol., 38: 1160-3, 2007.
Martinez-Onsurbe et al., "Aspiration cytology of 147 adnexal cysts with histologic correlation", Acta. Cytologica 45, 941-947, 2001.
Mayr et al., "KRAS and BRAF mutations in ovarian tumors: a comprehensive study of invasive carcinomas, borderline tumors and extraovarian implants", Gyencologic oncology 103, 883-887, 2006.
McAlpine et al., "Opportunistic salpingectomy: uptake, risks, and complications of a regional initiative for ovarian cancer prevention.", American journal of obstetrics and gynecology 210: 471 e1-11, 2014.
Mcdaniel et al., "Next-Generation Sequencing of Tubal Intraepithelial Carcinomas." JAMA oncology 1: 1128-32, 2015.
Medeiros et al., "The tubal fimbria is a preferred site for early adenocarcinoma in women with familial ovarian cancer syndrome.", The American journal, vol. 30, issue 2, pahes 230-236, 2006.
Menon et al., "Ovarian cancer screening-current status, future directions.", Gynecologic oncology 132: 490-5, 2014.
Moran et al., "Cytologic examination of ovarian cyst fluid for the distinction between benign and malignant tumors", Obstetrics and gynecology 82, 444-446, 1993.
Murtaza et al., "Non-invasive analysis of acuired resistance to cancer therapy by sequencing of plasma DNA", Nature 497, 108-112, 2013.
Newman et al., "An ultrasensitive method for quantitating circulating tumor DNA with board patient coverage", Nature medicine 20, 548-554, 2014.
Ngamruengphong et al., "Preoperative endoscopic ultrasound-guided fine needle aspiration does not impair survival of patients with resected pancreatic cancer.", Gut, 2015.
Nik et al., "Origin and pathogenesis of pelvic (ovarian, tubal, and primary peritoneal) serous carcinoma.", Annual review of pathology 9: 27-45, 2014.
Niknafs et al., SubClonal Hierarchy Inference from Somatic Mutations: Automatic Reconstruction of Cancer Evolutionary Trees from Multi-region Next Generation Sequencing. PLoS computational biology, 11: e1004416, pp. 1-26, 2015.
Parker et al., "Ovarian conservation at the time of hysterectomy and long-term health outcomes in the nurses' health study.", Obstetrics and gynecology, 113: 1027-37, 2009.
Patch et al., "Whole-genome characterization of chemoresistant ovarian cancer.", Nature, 521: 489-94, 2015.
Pavlik et al., "Frequency and diposition of ovarian abnormalities followed with serial transvaginal ultrasonography", Obstetrics and gynecology 122, 210-217, 2013.
Perets et al., "It's Totally Tubular . . . Riding The New Wave of Ovarian Cancer Research.", Cancer research, 76: 10-7, 2016.
Perets et al., "Transformation of the fallopian tube secretory epithelium leads to high-grade serous ovarian cancer in Brca;Tp53;Pten models.", Cancer cell, 24: 751-65, 2013.
Piek et al., "BRCA1/2-related ovarian cancers are of tubal origin: a hypothesis.", Gynecologic oncology, 90: 491, 2003.
Piek et al., "Dysplastic changes in prophylactically removed Fallopian tubes of women predisposed to developing ovarian cancer.", The Journal of pathology, 195: 451-6, 2001.
Rebbeck et al., "Prophylactic oophorectomy in Carriers of BRCA 1 or BRCA2 mutations.", The New England journal of medicine, 346: 1616-22, 2002.
Roh et al., "High-grade fimbrial—0varian carcinomas are unified by altered p53, PTEN and PAX2 expression.", Modem pathology, 23: 1316-24, 2010.
Schmeler et al., "Neoadjuvant chemotherapy for low-grade serous carcinoma of the ovary or peritoneum", Gynecologic oncology 108, 510-514, 2008.
Sherman et al., "Survival amound women with borderline ovarian tumors and ovarian carcinoma: a population-based analysis", Cancer 100, 1045-1052, 2004.
Shih et al., "Risk factors for recurrence of ovarian boderline tumors", Gynecologic oncology 120, 480-484, 2011.
Siegel et al., Cancer statistics, 2015, CA: a cancer journal for clinicians, 65:5-29, 2015.
Singer et al., "Mutations in BRAF and KRAS characterize the development of low-grade ovarian serous carcinoma", Journal of National Cancer Institute, vol. 95, No. 6, pp. 484-486, 2003.
Sundfeldt et al., "Specific mutant tumor DNA can be detected in ovarian cystic fluid of an unknown ovarian tumor cyst", In: The American Association for Cancer Research, 2015, abstract #2839.
Tran et al., "Tract embolization with gelatin sponge slurry for prevention of pneumothorax after percutaneous computed tomography-guided lung biopsy.", Cardiovascular and interventional radiology 37, 1546-1553, 2014.
Tsang et al., "KRAS (but not BRAF) mutations in ovarian serous borderline tumour are assocaited with recurrent low-grade serous carcinoma", The Journal of pathology 231, 449-456, 2013.
Tsang et al., "Ultrasound-guided plugged percutaneous biopsy of solid organs in patients with bleeding tendencies.", Hong Kong Medical Journal, 20, 107-112, 2014.
Ueland et al., "Effectiveness of a multivariate index assay in the preoperative assessment of ovarian tumors.", Obstetrics and gynecology 117, 1289-1297, 2011.
Van Nagell et al., "Ovarian cancer screening with annual transvaginal sonography: findings of 25,000 women screened.", Cancer 109, 1887-1896, 2007.
Vogelstein et al., "Cancer genome landscapes", Science 339, 1546-1558, 2013.
Volpe et al., "Techniques, safety and accuracy of sampling of renal tumors by fine needle aspiration and core biopsy", The journal of urology 178, 379-386, 2007.
Wu et al., "Whole-exome sequencing of neoplastic cysts of the pancreas reveals recurrent mutations in components of ubiquitin-dependent pathways", PNAS 108, 21188-21193, 2011.
Yachida et al., "Distant metastasis occurs late during the Jenetic evolution of pancreatic cancer.", Nature, 467: 1114-7, 2010.
Yamada et al., "It is possible to diagnose malignancy from fluid in cystic ovarian tumors?", European journal of obstetrics, gynecology, and reproductive biology 171, 96-100, 2013.
"Nextera XT DNA Sample Preparation Guide," Illumina, Oct. 1, 2012 (Oct. 1, 2012), Part# 15031942, Rev. C, pp. 1-48. Retrieved from the Internet:<http://cmore.soest.hawaii.edu/summercourse/2015/documents/Metagenomics_06-22/nextera_xt_sample_preparation_guide_15031942_c.pdf on Sep. 19, 2010 (Sep. 19, 2010).
Alizadeh et al., "The Lymphochip: A Specialized cDNA Microarray for the Genomic-scale Analysis of Gene Expression in Normal and Malignant Lymphocytes," Cold Spring Harbor Symposia on Quantitative Biology, 1999, vol. LXIV:71-78.
Beers et al., "Array-CGH and breast cancer," Breast Cancer Res., 2006, 8(3):210, 10 pages.
Bettegowda et al. "Detection of circulating tumor DNA in early-and late-stage human malignancies," Sci Transl Med, 2014, 6(224):1-25.

(56) References Cited

OTHER PUBLICATIONS

Cancer.gov [online], "NCI Dictionary of Cancer Terms, Definition of Biomarker," available on or before Apr. 5, 2018, [retrieved on Feb. 26, 2020], retrieved from: URL<https://www.cancer.gov/publications/dictionaries/cancer-terms/def/biomarker>, 1 page.
Castelo-Branco et al., "Methylation of the TERT promoter and risk stratification of childhood brain tumours: an integrative genomic and molecular study," Lancet Oncol., 2013, 14(6):534-542.
Color Hereditary Cancer Test, "A pathogenic mutation was identified in the BRCA1 gene," tm Clinical Grade testing (www.color.com), 2015, 1-12.
Cunningham et al., Cetuximab Monotherapy and Cetuximab plus Irinotecan in Irinotecan-Refractory Metastatic Colorectal Cancer, N. Engl. J. Med., 2004, 351(4):337-345.
Eckert et al., "Genomics of Ovarian Cancer Progression Reveals Diverse Metastatic Trajectories Including Intraepithelial Metastasis to the Fallopian Tube," Cancer Discov., 2016, 6(12):1342-1351.
Gaspari et al. "Fetal ovarian cysts: an early manifestation of McCune-Albright syndrome?,"Prenatal Diagnosis, 2012, 32:859-863.
GenBank Accession No. NM_006218, "*Homo sapiens* phosphatidyhnositol-4,5-bisphosphate 3-kinase catalytic subunit alpha (PIK3CA), mRNA," Feb. 16, 2020, 7 pages.
GenBank Accession No. NM_058197, "*Homo sapiens* cyclin dependent kinase inhibitor 2A (CDKN2A), transcript variant 3, mRNA," Dec. 29, 2019, 5 pages.
GenBank Accession No. NM_000546, "*Homo sapiens* tumor protein p53 (TP53), transcript variant 1, mRNA," Feb. 13, 2020, 11 pages.
GenBank Accession No. NM_001126112, "*Homo sapiens* tumor protein p53 (TP53), transcript variant 2, mRNA," Dec. 28, 2019, 11 pages.
GenBank Accession No. NM_001126113, "*Homo sapiens* tumor protein p53 (TP53), transcript variant 4, mRNA," Dec. 8, 2019, 6 pages.
GenBank Accession No. NM_001126114, "*Homo sapiens* tumor protein p53 (TP53), transcript variant 3, mRNA," Dec. 29, 2019, 9 pages.
GenBank Accession No. NM_001276761, "*Homo sapiens* tumor protein p53 (TP53), transcript variant 2, mRNA," Dec. 23, 2019, 5 pages.
Gudmundsson et al. "Genome-Wide Association and Replication Studies Identify Four Variants Associated with Prostate Cancer Susceptibility," Nat. Genet. 2009 41:1122-6.
Haber et al. "Blood-based analyses of cancer: circulating tumor cells and circulating tumor DNA," Cancer Discov, 2014, 4(6):650-661.
Hannady et al., "Error-correcting barcoded primers for pyrosequencing hundreds of samples in multiplex," Nature Meth., 2007, 5:1-36.
Hannady et al., "Error-correcting barcoded primers for pyrosequencing hundreds of samples in multiplex," Nature Meth., 2007, 5:235-237.
Heitzer et al., "Current and future perspectives of liquid bipsies in genomics-driven oncology", Nature Reviews Genetics, 2018, 20(2):71-88.
Huber et al., "High-Resolution Liquid Chromatography of DNA Fragments on Non-Porous Poly(Styrene-Divinylbenzene) Particles," Nucleic Acids Res., 1993, 21:1061-6.
International Preliminary Report on Patentability in PCT Appln. No. PCT/US2018/045669, dated Feb. 11, 2020, 7 pages.
International Search Report and Written Opinion in International Application No. PCT/US2018/030905, dated Oct. 2, 2018, 23 pages.
International Search Report and Written Opinion in International Application No. PCT/US2019/017973, dated May 17, 2019, 7 pages.
International Search Report and Written Opinion in International Application No. PCT/US2020/014172, dated Apr. 30, 2020, 18 pages.
International Search Report and Written Opinion in International Application No. PCT/US2017/061447, dated Feb. 19, 2018, 10 pages.
Jain et al., "Personalized Therapy of Cancer," Textbook of Personalized Medicine, 2015, Chapter 10, pp. 199-381.
Jung KW, et al. (2007) Clinicopathological aspects of 542 cases of pancreatic cancer: a special emphasis on small pancreatic cancer. J Korean Med Sci 22 Suppl:S79-85.
Kato et al., "A new Packing for Separation of DNA Restriction Fragments by High Performance Liquid Chromatography," J. Biochem, 1984, 95:83-86.
Khalid et al., "Pancreatic cyst fluid DNA analysis in evaluating pancreatic cysts: a report of the PANDA study," Gastrointestinal Endoscopy, 2009, 69(6): 1095-1102.
Kinde et al., 'Detection and quantification of rare mutations with massively parallel sequencing', PNAS, 2011, 108(23):9530-9535.
Leary et al. "Detection of chromosomal alterations in the circulation of cancer patients with whole-genome sequencing," Sci Transl Med, 2012, 4(162):1-21.
Liu et al., "Comparison of Next-Generation Sequencing Systems," Journal of Biomedicine and Biotechnology, 2012, 2012(251364) 11 pages.
Newman et al., 'Integrated digital error suppression for improved detection of circulating tumor DNA', Nature Biotechnology, 2016, 34(5):547-555.
Out et al., "Deep Sequencing to Reveal New Variants in Pooled DNA Samples," Hum. Mutat. 2009, 30:1703-1712.
Peng et al., "Targeted Single Primer Enrichment Sequencing with Single End Duplex-UMI," Scientific Reports, 2019, 9:4810, 10 pages.
Peng et al., 'Reducing amplification artifacts in high multiplex amplicon sequencing by using molecular barcodes, BMC Genomics, 2015, 16(589):1-12.
Resaei-Matehkolaei et al., Use of Single-enzyme PCR-restriction Digestion Bardode Targeting the Internal Transcribed Spacers (ITS rDNA) to identify Dermatophyte Species, Iranian J. Publ. Health, 2012, 41(3):82-94.
Shendure et al., "Next-generation DNA sequencing," nature biotechnology, 2008, 26(10):1135-1145.
Tabernero et al., "Dose-and Schedule-Dependent Inhibition of the Mammalian Target of Rapamycin Pathway With Everolimus: A Phase I Tumor Pharmacodynamic Study in Patients With Advanced Solid Tumors," J. Clin. Oncol., 2008, 26: 1603-1610.
Troiano et al., "Sonographically guided therapeutic aspiration of benign-appearing ovarian cysts and endometriomas," AJR, 1998, 171:1601-1605.
Turner et al., "Massively parallel exon capture and library-free resequencing across 16 genomes," Nat. Methods, 2009, 6:315-316.
Urick et al., "PIK3R1 (p85$\alpha$) Is Somatically Mutated at High Frequency in Primary Endometrial Cancer," Cancer Research, 2011, 71(12):4062-4064.
Van Dijk et al., "Ten years of next-generation sequencing technology," Trends in Genetics, 2014, 30(9):418-426.
Al-Shannsi et al., "Molecular spectrum of KRAS, NRAS, BRAF, PIK3CA, TP53, and APC somatic gene mutations In Arab patients with colorectal cancer: determination of frequency and distribution pattern," Journal of Gastrointerstinal Oncology, 2016, 7(6):882-902.
Balmain et al., "A model for RAS mutation patterns in cancers: finding the sweet spot.," Nature Reviews, 2018, 18:767-777.
Boland et al., "Clinical next generation sequencing to identify actionable aberrations in a phase I program," Oncotarget, 2015, 6(24):20099-20110.
Kodaz et al., Frequency of RAS Mutations (KRAS, NRAS, HRAS) in Human Solid Cancer, EJMO, 2017, 1(1):1-7.
Marengo et al., "Biomarkers for pancreatic cancer: Recent achievements in proteomics and genomics through classical and multivariate statistical methods," World J. Gastroenterol, 20(37):13325-13342, Oct. 7, 2014) (Year: 2014).
McConechy et al., "Use of mutation profiles to refine the classification of endometrial carcinomas," J. Path, 2012; 228: 20-30.

(56) References Cited

OTHER PUBLICATIONS

Young et al., Validation of Biomarkers for Early Detection of Pancreatic Cancer: Summary of the Alliance of Pancreatic Cancer Consortia for Biomarkers for Early Detection Workshop., Pancreas, 2018, 47(2):135-141.

Al-Jehani et al., "Model for the molecular genetic diagnosis of endometrial cancer using K-ras mutation analysis," Journal of the National Cancer Institute 1998, 90(7):540-542.

Cancer.gov[Online], "NCI Dictionary of cancer Terms, Definition of Pap Smear," retrieved on Apr. 27, 2022], retrieved from URL:https://www.cancer.gov/publications/dictionaries/cancer-terms/def/pap-smear.> 2 pages.

Gupta et al., "Extrauterine malignancies. Role of Pap smears in diagnosis and management.," Acta Cytologica, 1999, 43(5):806-813.

Wang et al., "Primary serous peritoneal carcinoma presenting first on a routine papanicolaou smear," Acta Cytologica 2010, 54(4): 623-626.

* cited by examiner

Table 1 - Epidemiology of Ovarian and Endometrial Tumors

| Tissue | Type | Subtype | Fraction of total | Estimated New Cases in U.S., 2012 | Estimated Deaths in U.S., 2012 | 5-year Survival | Reference No. |
|---|---|---|---|---|---|---|---|
| Ovarian | Epithelial | High-grade Serous | 60% | 13,368 | 9,224 | 9% | 43, 44 |
| | | Endometrioid | 15% | 3,342 | 2,373 | 71% | 43, 45 |
| | | Clear Cell | 10% | 2,228 | 1,361 | 62% | 43, 45 |
| | | Low-grade Serous | 8% | 1,782 | 1,105 | 40% | 43, 44 |
| | | Mucinous | 2% | 446 | 348 | 65% | 43, 45 |
| | | Other | 5% | 1,114 | 722 | N/A | 43, 44, 45 |
| Endometrial | Type I: Endometrioid | Endometrioid | 85% | 40,060 | 5,180 | 91% | 43, 45 |
| | Type II: Non-Endometrioid | Papillary Serous | 10% | 4,713 | 2,194 | 45% | 43, 45 |
| | | Clear Cell | 5% | 2,357 | 650 | 68% | 43, 46 |

Fig. 5

Table 2 - Genetic Characteristics of Ovarian and Endometrial Cancers

| Tissue | Type | Subtype | Common Mutations (Frequency) | Reference No. |
|---|---|---|---|---|
| Ovarian | Epithelial | High-grade Serous | TP53 (96%) | 23 |
| | | Endometrioid | TP53 (68%) | 26 |
| | | | ARID1A (30%) | 26 |
| | | | CTNNB1 (26%) | 26 |
| | | | PTEN (17%) | 26 |
| | | | PIK3CA (15%) | 26 |
| | | | KRAS (10%) | 26 |
| | | | PPP2R1A (11%) | 26 |
| | | | CDKN2A (12%) | 26 |
| | | | BRAF (8%) | 26 |
| | | Clear Cell | ARID1A (57%) | 24 |
| | | | PIK3CA (40%) | 24 |
| | | | PPP2R1A (7.1%) | 24 |
| | | | KRAS (4.7%) | 24 |
| | | Low-grade Serous | BRAF (36%) | 25 |
| | | | KRAS (19%) | 25 |
| | | Mucinous | TP53 (56%) | 26 |
| | | | KRAS (40%) | 26 |
| | | | PPP2R1A (33%) | 26 |
| | | | CDKN2A (16%) | 26 |
| | | | PTEN (11%) | 26 |

| Tissue | Type | Subtype | Common Mutations (Frequency) | Reference No. |
|---|---|---|---|---|
| Endometrial | Type I: Endometriod | Endometrioid | PTEN (64%) | Current study |
| | | | PIK3CA (59%) | Current study |
| | | | ARID1A (55%) | Current study |
| | | | CTNNB1 (32%) | Current study |
| | | | MLL2 (32%) | Current study |
| | | | FBXW7 (27%) | Current study |
| | | | RNF43 (27%) | Current study |
| | | | APC (23%) | Current study |
| | | | FGFR2 (18%) | Current study |
| | | | KRAS (9%) | Current study |
| | | | PIK3R1 (9%) | Current study |
| | | | EGFR (14%) | Current study |
| | | | AKT1 (5%) | Current study |
| | | | NRAS (5%) | Current study |
| | | | TP53 (5%) | Current study |
| | Type II: Non-Endometrioid | Papillary serous | TP53 (81.6%) | 29 |
| | | | PIK3CA (24%) | 29 |
| | | | FBXW7 (19.7%) | 29 |
| | | | PPP2R1A (18.4%) | 29 |
| | | Clear Cell | TP53 (45%) | 26 |
| | | | PPP2R1A (33%) | 26 |
| | | | PIK3CA (29%) | 26 |
| | | | PTEN (13%) | 26 |
| | | | PIK3R1 (9%) | 26 |
| | | | KRAS (5%) | 26 |

Fig. 6

Table S1: Endometrial Cancers (Endometrioid Subtype) Studied by Whole-exome Sequencing

| Tumor ID | Age | Stage (FIGO) | Pathologic Stage (TNM class) | Number of Mutations | Microsatellite Stability Status* |
|---|---|---|---|---|---|
| PAP 003 | 53 | IB | T1bN0M0 | 847 | MSS |
| PAP 010 | 73 | IB | T1bN0M1 | 29 | MSS |
| PAP 011 | 58 | IB | T1bN0M2 | 579 | MSI-H |
| PAP 024 | 56 | IA | T1aN0 | 7 | MSS |
| PAP 026 | 86 | IA | T1a | 769 | MSI-H |
| PAP 030 | 73 | IA | T1aNx | 49 | MSS |
| PAP 031 | 61 | IA | T1aNx | 41 | MSS |
| PAP 032 | 82 | IA | T1aNx | 9 | MSS |
| PAP 033 | 68 | IA | T1aNX | 34 | MSS |
| PAP 034 | 55 | IA | T1aN0 | 454 | MSI-H |
| PAP 043 | 55 | IB | T1BN0MX | 26 | MSS |
| PAP 045 | 57 | IB | T1BN0MX | 4629 | MSS |
| PAP 046 | 44 | IIA | T2ANXMX | 40 | MSS |
| PAP 047 | 53 | IA | T1AN0MX | 1767 | MSS |
| PAP 048 | 62 | IIIC | T2AN1MX | 394 | MSI-H |
| PAP 049 | 45 | IIB | T2BN0MX | 20 | MSS |
| PAP 050 | 39 | IB | T1BN0MX | 50 | MSS |
| PAP 052 | 70 | IVB | T1AN1M1 | 164 | MSI-H |
| PAP 053 | 66 | IB | T1BN0MX | 1102 | MSI-H |
| PAP 054 | 73 | IA | T1ANXMX | 413 | MSI-H |
| PAP 055 | 61 | IA | T1AN0MX | 1195 | MSS |
| PAP 057 | 59 | IIB | T2BN0MX | 176 | MSI-H |

* MSI-H: micosatellite unstable; MSS: microsatellite stable. See Materials and Methods

Fig. 7

Table S3. Mutations Assessed in Pap Smears

| Case # | Age | Tissue | Subtype | Clinical Stage (FIGO) | Race/ Ethnicity | DNA recovered from Pap smear fluid (ug) | Mutated Gene Name | Mutated Gene ID | Nucleotide (genomic)* | Transcript | Nucleotide (transcript) | Amino Acid (protein) | Mutation Type | Fraction of mutant alleles in Pap smear fluid |
|---|---|---|---|---|---|---|---|---|---|---|---|---|---|---|
| PAP 001 | 45 | Endometrial | Endometrioid | IB | White | 30.8 | PIK3CA | ENSG00000121879 | g.chr3:180434779A>G | CCDS43171.1 | c.3140A>G | p.H1047R | Missense | 10.00% |
| PAP 002 | 39 | Ovarian | Papillary serous | IIIC | White | 3.65 | TP53 | ENSG00000141510 | g.chr17:7519215A>T | CCDS11118.1 | c.440T>A | p.V147D | Missense | 0.40% |
| PAP 003 | 53 | Endometrial | Endometrioid | IB | White | 5.2 | APC | ENSG00000134982 | g.chr5:112203538C>T | CCDS4107.1 | c.4348C>T | p.R1450X | Missense | 3.20% |
| PAP 004 | 38 | Ovarian | Papillary serous | IB | White | 0.36 | TP53 | ENSG00000141510 | g.chr17:7519154delC | CCDS11118.1 | c.501delG | Frameshift | Indel | <0.005% |
| PAP 005 | 59 | Ovarian | Borderline papillary serous cystadenocarcinoma | IIIC | White | 7.6 | NF1 | ENSG00000196712 | g.chr17:26552610insC | CCDS42292.1 | c.1241insC | Frameshift | Indel | <0.005% |
| PAP 006 | 57 | Ovarian | Papillary serous | IIIC | White | 8.2 | TP53 | ENSG00000141510 | g.chr17:7517824C>T | CCDS11118.1 | c.839G>A | p.R280K | Missense | <0.005% |
| PAP 007 | 63 | Ovarian | Papillary serous | IIIC | White | 6.8 | TP53 | ENSG00000141510 | g.chr17:7517783C>A | CCDS11118.1 | c.880G>T | p.E294X | Nonsense | <0.005% |
| PAP 010 | 73 | Endometrial | Endometrioid | IB | White | 8.6 | FBXW7 | ENSG00000109670 | g.chr4:153466817G>A | CCDS3777.1 | c.1435C>T | p.R479X | Nonsense | 15.00% |
| PAP 011 | 58 | Endometrial | Endometrioid | IB | White | 11.2 | KRAS | ENSG00000133703 | g.chr12:25289551C>G | CCDS8703.1 | c.35G>C | p.G12A | Missense | 3.50% |
| PAP 024 | 56 | Endometrial | Endometrioid with squamous differentiation | IA | White | 5.6 | CTNNB1 | ENSG00000168036 | g.chr3:41241108G>T | CCDS2694.1 | c.101G>T | p.G34V | Missense | 0.22% |
| PAP 025 | 75 | Endometrial | Serous carcinoma | IA | Black | 0.74 | TP53 | ENSG00000141510 | g.chr17:7520119_7520120delGG | CCDS11118.1 | c.292_293delCC | Frameshift | Indel | 5.70% |
| PAP 026 | 86 | Endometrial | Endometrioid carcinoma | IA | White | 17.64 | PTEN | ENSG00000171862 | g.chr10:89710752G>A | CCDS31238.1 | c.923G>A | p.R308H | Missense | 0.01% |
| PAP 027 | 65 | Ovarian | Papillary serous | IIIC | White | 16.6 | SETD2 | ENSG00000181555 | g.chr3:47138125G>A | NM_014159 | c.805C>T | p.Q269X | Nonsense | <0.005% |
| PAP 030 | 73 | Endometrial | Endometrioid | IA | White | 17.58 | MSH6 | ENSG00000116062 | g.chr2:47880779G>A | CCDS1836.1 | c.2153G>A | p.S718N | Missense | 0.24% |
| PAP 031 | 61 | Endometrial | Endometrioid | IA | Asian | 101.4 | CTNNB1 | ENSG00000168036 | g.chr3:41241117C>A | CCDS2694.1 | c.110C>A | p.S37Y | Missense | 1.30% |
| PAP 032 | 82 | Endometrial | Endometrioid | IA | White | 2.218 | PTEN | ENSG00000171862 | g.chr10:89682884C>G | CCDS31238.1 | c.388C>G | p.R130G | Missense | 0.02% |
| PAP 033 | 68 | Endometrial | Endometrioid with squamous differentiation | IA | White | 33.3 | KRAS | ENSG00000133703 | g.chr12:25289551C>A | CCDS8703.1 | c.35G>T | p.G12V | Missense | 1.53% |
| PAP 34 | 55 | Endometrial | Endometrioid | IA | White | 11.24 | CTNNB1 | ENSG00000168036 | g.chr3:41241107G>A | CCDS2694.1 | c.100G>A | p. G34R | Missense | 20.12% |
| PAP 35 | 50 | Endometrial | Endometrioid | IVB | White | 8.48 | KRAS | ENSG00000133703 | g.chr12:25289551C>T | CCDS8703.1 | c.35G>A | p.G12D | Missense | 6.34% |
| PAP 36 | 57 | Ovarian | Endometrioid with squamous differentiation | IA | White | 2.47 | PIK3CA | ENSG00000121879 | g.chr3:180418789A>T | CCDS43171.1 | c.1637A>T | p.Q546L | Missense | <0.005% |
| PAP 37 | 64 | Endometrial | Endometrioid | IA | Asian | 10.3 | PIK3CA | ENSG00000121879 | g.chr3:180434712A>G | CCDS43171.1 | c.3073A>G | p.T1025A | Missense | 0.17% |
| PAP 38 | 47 | Ovarian | Papillary serous | IA | Asian | 5.2 | TP53 | ENSG00000141510 | g.chr17:7518915T>C | CCDS11118.1 | c.659A>G | p.Y220C | Missense | 0.48% |
| PAP 39 | 73 | Ovarian | Papillary serous | IA | Asian | 9.9 | TP53 | ENSG00000141510 | g.chr17:7518244delG | CCDS11118.1 | c.871delC | Frameshift | Indel | 5.90% |
| PAP 40 | 57 | Endometrial | Endometrioid | IB | Asian | 7.7 | CTNNB1 | ENSG00000168036 | g.chr3:41241141C>A | CCDS2694.1 | c.134C>A | p.S45Y | Missense | 0.08% |
| PAP 41 | 66 | Endometrial | Papillary serous | IA | Asian | 5.7 | FGFR2 | ENSG00000066468 | g.chr10:123269667G>C | CCDS7620.2 | c.755C>G | p.S252W | Missense | 0.15% |
| PAP 41 | 66 | Endometrial | Papillary serous | IA | Asian | 5.7 | PTEN | ENSG00000171862 | g.chr10:89682902T>C | CCDS31238.1 | c.406T>C | p.C136R | Missense | 0.09% |
| PAP 42 | 45 | Ovarian | Adenosquamous Carcinoma | IIIC | White | 34.3 | TP53 | ENSG00000141510 | g.chr17:7520074insA | CCDS11118.1 | c.339insT | Frameshift | Indel | 1.47% |
| PAP 58 | 62 | Ovarian | Papillary serous | IIIC | White | 14.469 | PIK3CA | ENSG00000121879 | g.chr3:180399630G>A | CCDS43171.1 | c.323G>A | p.R108H | Missense | 0.49% |
| PAP 60 | 69 | Ovarian | Papillary serous | IIIC | White | 5.332 | TP53 | ENSG00000141510 | g.chr17:7519131C>T | CCDS11118.1 | c.524G>A | p.R175H | Missense | <0.05% |
| PAP 61 | 70 | Ovarian | Papillary serous | IIIC | White | 5.872 | TP53 | ENSG00000141510 | g.chr17:7517846G>A | CCDS11118.1 | c.817C>T | p.R273C | Missense | 0.02% |
| PAP 62 | 55 | Ovarian | Papillary serous | IIIC | White | 1.444 | TP53 | ENSG00000141510 | g.chr17:7520213_7520216delGCAT | CCDS11118.1 | c.196_199delATGC | Frameshift | Indel | <0.005% |
| PAP 63 | 66 | Ovarian | Papillary serous | IIIB | White | 7.376 | TP53 | ENSG00000141510 | g.chr17:7519131C>T | CCDS11118.1 | c.524G>A | p.R175H | Missense | <0.005% |
| PAP 64 | 50 | Ovarian | Dysgerminoma | IIIA | Asian | 5.6 | TP53 | ENSG00000141510 | g.chr17:7518233T>G | CCDS11118.1 | c.773A>C | p.E258A | Missense | 4.20% |
| PAP 66 | 70 | Endometrial | Endometrioid Adenocarcinoma, Villoglandular Type | IIIC | Asian | 7.2 | TP53 | ENSG00000141510 | g.chr17:7518980T>C | CCDS11118.1 | c.614A>G | p.Y205C | Missense | 9.48% |
| PAP 67 | 61 | Endometrial | Endometrioid | IB | Asian | 9.3 | TP53 | ENSG00000141510 | g.chr17:7518937G>A | CCDS11118.1 | c.637C>T | p.R213X | Nonsense | 2.70% |
| PAP 68 | 63 | Endometrial | Endometrioid Adenocarcinoma with Mucinous Differentiation | IB | Asian | 8.6 | PIK3CA | ENSG00000121879 | g.chr3:180410672T>C | CCDS43171.1 | c.1258T>C | p.C420R | Missense | 0.03% |
| PAP 69 | 51 | Endometrial | Endometrioid | IB | Asian | 7.4 | TP53 | ENSG00000141510 | g.chr17:7520084G>A | CCDS11118.1 | c.328C>T | p.R110C | Missense | 14.70% |
| PAP 70 | 49 | Endometrial | Endometrioid | IIIA | Asian | 3.6 | PIK3CA | ENSG00000121879 | g.chr3:180399570G>A | CCDS43171.1 | c.263G>A | p.R88Q | Missense | 29.60% |
| PAP 71 | 57 | Endometrial | Endometrioid | IA | White | 4.42 | PIK3CA | ENSG00000121879 | g.chr3:180434779A>G | CCDS43171.1 | C.3140A>G | p.H1047R | Missense | 0.37% |
| PAP 72 | 68 | Ovarian | Papillary serous | IV | White | 4.24 | TP53 | ENSG00000141510 | g.chr17:7518272C>T | CCDS11118.1 | c.734G>A | p.G245D | Missense | 0.85% |
| PAP 73 | 64 | Ovarian | Papillary serous | IIIC | White | 4.62 | TP53 | ENSG00000141510 | g.chr17:7519167T>C | CCDS11118.1 | c.488A>G | p.Y163C | Missense | <0.005% |
| PAP 74 | 73 | Ovarian | Papillary serous | IV | White | 8.28 | TP53 | ENSG00000141510 | g.chr17:7519131C>T | CCDS11118.1 | c.524G>A | p.R175H | Missense | <0.05% |
| PAP 75 | 54 | Ovarian | Papillary serous | IIIC | White | 7.42 | PIK3CA | ENSG00000121879 | g.chr3:180434768G>A | CCDS43171.1 | c.3129G>A | p.M1043I | | 0.13% |
| PAP 76 | 53 | Ovarian | Papillary serous | IIIC | White | 9.38 | TP53 | ENSG00000141510 | g.chr17:7519275G>A | CCDS11118.1 | c.380C>T | p.S127F | Missense | <0.005% |
| PAP 78 | 53 | Ovarian | Papillary serous | IIIC | White | 1.36 | TP53 | ENSG00000141510 | g.chr17:7519131C>T | CCDS11118.1 | c.524G>A | p.R175H | Missense | <0.005% |
| PAP 80 | 56 | Endometrial | Papillary serous | IIIA | Black | 7.78 | TP53 | ENSG00000141510 | g.chr17:7519005delG | CCDS11118.1 | c.566delC | Frameshift | Indel | 79.80% |
| PAP 83 | 51 | Endometrial | Endometrioid | IA | Black | 4.5 | PIK3CA | ENSG00000121879 | g.chr3:180434779A>G | CCDS43171.1 | C.3140A>G | p.H1047R | Missense | 0.14% |
| PAP 83 | 51 | Endometrial | Endometrioid | IA | Black | 4.5 | CTNNB1 | ENSG00000168036 | g.chr3:41241105C>A | CCDS2694.1 | c.98C>A | p.S33Y | Missense | 0.07% |

*Coordinates refer to the human reference genome hg18 release (NCBI 36.1, March 2006).

Fig. 8

Table S4. Primers Used to Assess Individual Mutations in Pap Smears

| Sample# | Gene | Mutation | Amplified Genomic Fragment Size (bp) | Forward Primer Sequence | Reverse Primer Sequence |
|---|---|---|---|---|---|
| PAP 001 | PIK3CA | H1047R | 82 | cgacgtaaaacgacggccagtNNNNNNNNNNNNNNGATCCAATCCATTTTTGTTGTCCAG | cacacaggaaacagctatgaccatgTGAGCAAGAGGCTTTGGAGT |
| PAP 002 | TP53 | V147D | 93 | cgacgtaaaacgacggccagtNNNNNNNNNNNNNNGGCCAAGACCTGCCCTG | cacacaggaaacagctatgaccatgTGCTGTGACTGCTTGTAGATGG |
| PAP 003 | APC | R1450X | 93 | cgacgtaaaacgacggccagtNNNNNNNNNNNNNNCCACCTCCTCAAACAGCTCAA | cacacaggaaacagctatgaccatgTGCAGCTTGCTTAGGTCCACT |
| PAP 004 | TP53 | Q167fs*(1 base deletion of C) | 85 | cgacgtaaaacgacggccagtNNNNNNNNNNNNNNTGGCCATCTACAAGCAGTCA | cacacaggaaacagctatgaccatgNNNNTCACCATCGCTATCTGAGCA |
| PAP 005 | NF1 | L414fs*(1 base insertion of C) | 74 | cgacgtaaaacgacggccagtNNNNNNNNNNNNNNCATTGGTGATGATTCGATGG | cacacaggaaacagctatgaccatgCTGCCTGGCTCAGAATTCAC |
| PAP 006 | TP53 | R280K | 90 | cgacgtaaaacgacggccagtNNNNNNNNNNNNNNCCCTTTCTTGCGGAGATTC | cacacaggaaacagctatgaccatgCTACTGGGACGGAACAGCTT |
| PAP 007 | TP53 | E294X | 87 | cgacgtaaaacgacggccagtNNNNNNNNNNNNNNGGAAGAGAATCTCCGCAAGA | cacacaggaaacagctatgaccatgGCTTCTTGTCCTGCTTGCTT |
| PAP 010 | FBXW7 | R479X | 82 | cgacgtaaaacgacggccagtNNNNNNNNNNNNNNGGCCTGTCTCAATATCCCAAA | cacacaggaaacagctatgaccatgTTGTTTTTCTGTTTCTCCCTCTG |
| PAP 011 | KRAS | G12A | 92 | cgacgtaaaacgacggccagtNNNNNNNNNNNNNNCAAGGCACTCTTGCCTACG | cacacaggaaacagctatgaccatgCATTTTCATTATTTTTATTATAAGGCCTG |
| PAP 024 | CTNNB1 | G34V | 72 | cgacgtaaaacgacggccagtNNNNNNNNNNNNNNCTGTGGTAGTGGCACCAGAA | cacacaggaaacagctatgaccatgNNNNAAGCGGCTGTTAGTCACTGG |
| PAP 025 | TP53 | P98fs*(2 base deletion of CC) | 91 | cgacgtaaaacgacggccagtNNNNNNNNNNNNNNGGCCCCTGTCATCTTCTGT | cacacaggaaacagctatgaccatgGACTTGGCTGTCCCAGAATG |
| PAP 026 | PTEN | R308H | 99 | cgacgtaaaacgacggccagtNNNNNNNNNNNNNNCAAGAAATCGATAGCATTTGCAG | cacacaggaaacagctatgaccatgTTTATTTGCTTTGTCAAGATCATTTTT |
| PAP 027 | SETD2 | Q269X | 85 | cgacgtaaaacgacggccagtNNNNNNNNNNNNNNAGGAAATATCTGCTTGCTCATTCAA | cacacaggaaacagctatgaccatgGAAGCAGATACTAAGCAGGACACTATATC |
| PAP 030 | MSH6 | S718N | 76 | cgacgtaaaacgacggccagtNNNNNNNNNNNNNNTTCCCTTGGATTCTGACACA | cacacaggaaacagctatgaccatgAGCACCATTCGTTGATAGGC |
| PAP 031 | CTNNB1 | S37Y | 85 | cgacgtaaaacgacggccagtNNNNNNNNNNNNNNCACTGGCAGCAACAGTCTTACC | cacacaggaaacagctatgaccatgGATTGCCTTTACCACTCAGAGAAG |
| PAP 032 | PTEN | R130G | 71 | cgacgtaaaacgacggccagtNNNNNNNNNNNNNNttgcagcaattcactgtaaagc | cacacaggaaacagctatgaccatgccgatgtaataaatatgcacatatcattac |
| PAP 033 | KRAS | G12V | 92 | cgacgtaaaacgacggccagtNNNNNNNNNNNNNNCAAGGCACTCTTGCCTACG | cacacaggaaacagctatgaccatgCATTTTCATTATTTTTATTATAAGGCCTG |
| PAP 034 | CTNNB1 | G34R | 85 | cgacgtaaaacgacggccagtNNNNNNNNNNNNNNCACTGGCAGCAACAGTCTTACC | cacacaggaaacagctatgaccatgGATTGCCTTTACCACTCAGAGAAG |
| PAP 035 | KRAS | G12D | 92 | cgacgtaaaacgacggccagtNNNNNNNNNNNNNNCAAGGCACTCTTGCCTACG | cacacaggaaacagctatgaccatgCATTTTCATTATTTTTATTATAAGGCCTG |
| PAP 036 | PIK3CA | Q546L | 84 | cgacgtaaaacgacggccagtNNNNNNNNNNNNNNAGCTCAAAGCAATTTCTACACGA | cacacaggaaacagctatgaccatgNNNNGCACTTACCTGTGACTCCATAGAA |
| PAP 037 | PIK3CA | T1025A | 70 | cgacgtaaaacgacggccagtNNNNNNNNNNNNNNctttgatgacattgcatacattc | cacacaggaaacagctatgaccatgNNNNactccaaagcctcttGCTCA |
| PAP 038 | TP53 | Y220C | 83 | cgacgtaaaacgacggccagtNNNNNNNNNNNNNNcagttgcaaaccagacctca | cacacaggaaacagctatgaccatgtgtggagtatttggatgacagaaa |
| PAP 039 | TP53 | I254fs*(1 base deletion of C) | 76 | cgacgtaaaacgacggccagtNNNNNNNNNNNNNNgtggcaagtggctcctga | cacacaggaaacagctatgaccatgNNNNCATGGGCGGCATGAAC |
| PAP 040 | CTNNB1 | S45Y | 90 | cgacgtaaaacgacggccagtNNNNNNNNNNNNNNactggcagcaacagtcttacct | cacacaggaaacagctatgaccatgNNNNCCTCAGGATTGCCTTTACCa |
| PAP 041 | FGFR2 | S252W | 71 | cgacgtaaaacgacggccagtNNNNNNNNNNNNNNagtccggcttGGAGGATG | cacacaggaaacagctatgaccatgtccccactcctcctttcttc |
|  | PTEN | C136R | 78 | cgacgtaaaacgacggccagtNNNNNNNNNNNNNNggaaagGGACGAACTGGTG | cacacaggaaacagctatgaccatgNNNNtagggcctcttgtgccttta |
| PAP 042 | TP53 | F113fs*(1 base insertion of T) | 80 | cgacgtaaaacgacggccagtNNNNNNNNNNNNNNtcttctgtcccttcccagaa | cacacaggaaacagctatgaccatgNNNNgacttGGCTGTCCCAGAATG |
| PAP 058 | PIK3CA | R108H | 82 | cgacgtaaaacgacggccagtNNNNNNNNNNNNNNtcatACCAATTTCTCGATTGAGG | cacacaggaaacagctatgaccatgNNNNcggcttttcaaccctttt |
| PAP 060 | TP53 | R175H | 85 | cgacgtaaaacgacggccagtNNNNNNNNNNNNNNTGGCCATCTACAAGCAGTCA | cacacaggaaacagctatgaccatgNNNNTCACCATCGCTATCTGAGCA |
| PAP 061 | TP53 | R273C | 76 | cgacgtaaaacgacggccagtNNNNNNNNNNNNNNgGACGGAACAGCTTTGAG | cacacaggaaacagctatgaccatgNNNNgcggagattctcttcctctgt |
| PAP 062 | TP53 | M66fs*(4 base deletion of GCAT | 77 | cgacgtaaaacgacggccagtNNNNNNNNNNNNNNCGGTGTAGGAGCTGCTGGT | cacacaggaaacagctatgaccatgNNNNACCCAGGTCCAGATGAAGC |
| PAP 063 | TP53 | R175H | 85 | cgacgtaaaacgacggccagtNNNNNNNNNNNNNNTGGCCATCTACAAGCAGTCA | cacacaggaaacagctatgaccatgNNNNTCACCATCGCTATCTGAGCA |
| PAP 064 | TP53 | E258A | 76 | cgacgtaaaacgacggccagtNNNNNNNNNNNNNNgtggcaagtggctcctga | cacacaggaaacagctatgaccatgNNNNCATGGGCGGCATGAAC |
| PAP 066 | TP53 | Y205C | 74 | cgacgtaaaacgacggccagtNNNNNNNNNNNNNNCGAAAAGTGTTTCTGTCATCCA | cacacaggaaacagctatgaccatgNNNNGCCCCTCCTCAGCATCTTAT |
| PAP 067 | TP53 | R213X | 83 | cgacgtaaaacgacggccagtNNNNNNNNNNNNNNcagttgcaaaccagacctca | cacacaggaaacagctatgaccatgNNNNtgtggagtatttggatgacagaaa |
| PAP 068 | PIK3CA | C420R | 90 | cgacgtaaaacgacggccagtNNNNNNNNNNNNNNTTATATTTCCCCATGCCAATG | cacacaggaaacagctatgaccatgNNNNggtgtttgaaatgtgtttataatttaga |
| PAP 069 | TP53 | R110C | 80 | cgacgtaaaacgacggccagtNNNNNNNNNNNNNNtcttctgtcccttcccagaa | cacacaggaaacagctatgaccatgNNNNgacttGGCTGTCCCAGAATG |
| PAP 070 | PIK3CA | R88Q | 66 | cgacgtaaaacgacggccagtNNNNNNNNNNNNNNGAAAAAGCCGAAGGTCACAA | cacacaggaaacagctatgaccatgNNNNCTCAAGAAGCAGAAAGGGAAGA |
| PAP 071 | PIK3CA | H1047R | 82 | cgacgtaaaacgacggccagtNNNNNNNNNNNNNNGATCCAATCCATTTTTGTTGTCCAG | cacacaggaaacagctatgaccatgNNNNTGAGCAAGAGGCTTTGGAGT |
| PAP 072 | TP53 | G245D | 74 | cgacgtaaaacgacggccagtNNNNNNNNNNNNNNTGTGATGATGGTGAGGATGg | cacacaggaaacagctatgaccatgNNNNtccacTACAACTACATGTGTAACAGTTC |
| PAP 073 | TP53 | Y163C | 84 | cgacgtaaaacgacggccagtNNNNNNNNNNNNNNCTCCGTCATGTGCTGTGACT | cacacaggaaacagctatgaccatgNNNNcagctgtgggttgattcca |
| PAP 074 | TP53 | R175H | 85 | cgacgtaaaacgacggccagtNNNNNNNNNNNNNNTGGCCATCTACAAGCAGTCA | cacacaggaaacagctatgaccatgNNNNTCACCATCGCTATCTGAGCA |
| PAP 075 | PIK3CA | M1043I | 79 | cgacgtaaaacgacggccagtNNNNNNNNNNNNNNccaatccatttttgttgtcca | cacacaggaaacagctatgaccatgNNNNTGAGCAAGAGGCTTTGGAGT |
| PAP 076 | TP53 | S127F | 82 | cgacgtaaaacgacggccagtNNNNNNNNNNNNNNcgcacagggcaggtctt | cacacaggaaacagctatgaccatgNNNNctctgtctccttcctcttcctaca |
| PAP 078 | TP53 | R175H | 85 | cgacgtaaaacgacggccagtNNNNNNNNNNNNNNTGGCCATCTACAAGCAGTCA | cacacaggaaacagctatgaccatgNNNNTCACCATCGCTATCTGAGCA |
| PAP 080 | PIK3CA | A189fs*(1 base deletion of C) | 78 | cgacgtaaaacgacggccagtNNNNNNNNNNNNNNcacgcaaATTTCCTTCCACT | cacacaggaaacagctatgaccatgNNNNggcctctgattcctcactgat |
| PAP 083 | PIK3CA | H1047R | 82 | cgacgtaaaacgacggccagtNNNNNNNNNNNNNNGATCCAATCCATTTTTGTTGTCCAG | cacacaggaaacagctatgaccatgNNNNTGAGCAAGAGGCTTTGGAGT |
|  | CTNNB1 | S33Y | 90 | cgacgtaaaacgacggccagtNNNNNNNNNNNNNNactggcagcaacagtcttacct | cacacaggaaacagctatgaccatgNNNNCCTCAGGATTGCCTTTACCa |

Fig. 9

Table S5. Primers Used to Simultaneously Assess 12 Genes in Pap Smears

| Set | Gene and Codons Covered by Amplicon | Amplicon Length (bp) | Forward Primer Sequence | Reverse Primer sequence |
|---|---|---|---|---|
| | CTNNB1 005 To 064 | 251 | cgacgtaaaacgacggccagtNNNNNNNNNNNNNNAAAGTAACATTTCCAATCTACTAATGCT | cacacaggaaacagctatgaccatgNNNNtgagaaaatccctgttcccac |
| | EGFR 697 to 728 | 264 | cgacgtaaaacgacggccagtNNNNNNNNNNNNNNTGGAGCCTCTTACACCCAGT | cacacaggaaacagctatgaccatgNNNNAAAAACACTGGAGTTTCCCAAA |
| | PIK3CA 0023 to 88 | 241 | cgacgtaaaacgacggccagtNNNNNNNNNNNNNNgaaaAAGCCGAAGGTCACAA | cacacaggaaacagctatgaccatgNNNNATGCCCCCAAGAATCCTAGT |
| #1 | PTEN 001 to 026 | 257 | cgacgtaaaacgacggccagtNNNNNNNNNNNNNNcatccgtctactcccacgtt | cacacaggaaacagctatgaccatgNNNNatcagctaccgccaagtcc |
| | PTEN 085 to 123 | 261 | cgacgtaaaacgacggccagtNNNNNNNNNNNNNNTTCGTCCCTTTCCAGCTTTA | cacacaggaaacagctatgaccatgNNNNggaatccagtgtttcttttaaatacct |
| | TP53 126 to 186 | 259 | cgacgtaaaacgacggccagtNNNNNNNNNNNNNNaccagccctgtcgtctctc | cacacaggaaacagctatgaccatgNNNNgccctgactttcaactctgtct |
| | TP53 308 To 331 | 259 | cgacgtaaaacgacggccagtNNNNNNNNNNNNNNgcctcagattcactttatcacct | cacacaggaaacagctatgaccatgNNNNaccaggagccattgtctttg |
| | BRAF 439 to 475 | 251 | cgacgtaaaacgacggccagtNNNNNNNNNNNNNNTCACCACATTACATACTTACCATGC | cacacaggaaacagctatgaccatgNNNNaaggggatctcttcctgtatcc |
| | EGFR 738 to 761 | 279 | cgacgtaaaacgacggccagtNNNNNNNNNNNNNNTCTGGATCCCAGAAGGTGAG | cacacaggaaacagctatgaccatgNNNNGGCCAGTGCTGTCTCTAAGG |
| | KRAS 001 to 021 | 281 | cgacgtaaaacgacggccagtNNNNNNNNNNNNNNGTCCACAAAATGATTCTGAATTAGC | cacacaggaaacagctatgaccatgNNNNACGATACACGTCTGCAGTCAAC |
| #2 | PIK3CA 0062 to 0117 | 269 | cgacgtaaaacgacggccagtNNNNNNNNNNNNNNACAGAAATATTTTAGAAAGGGACAACA | cacacaggaaacagctatgaccatgNNNNAGAAAATACCCCCTCCATCAAC |
| | PIK3CA 0980 to 1049 | 272 | cgacgtaaaacgacggccagtNNNNNNNNNNNNNNGATCCAATCCATTTTTGTTGTCCAG | cacacaggaaacagctatgaccatgNNNNTCCAAACTGACCAAACTGTTCTTA |
| | PTEN 100 to 164 | 294 | cgacgtaaaacgacggccagtNNNNNNNNNNNNNNgaaacccaaaatctgttttcca | cacacaggaaacagctatgaccatgNNNNGACCATAACCCACCACAGCTA |
| | TP53 186 to 224 | 251 | cgacgtaaaacgacggccagtNNNNNNNNNNNNNNctcctcccagagaccccagt | cacacaggaaacagctatgaccatgNNNNcatgagcgctgctcagatag |
| | TP53 332 To 366 | 263 | cgacgtaaaacgacggccagtNNNNNNNNNNNNNNcctaggaaggcaggggagt | cacacaggaaacagctatgaccatgNNNNtgcatgttgcttttgtaccg |
| | AKT1 017 to 058 | 279 | cgacgtaaaacgacggccagtNNNNNNNNNNNNNNaccacccgcacgtctgtag | cacacaggaaacagctatgaccatgNNNNagccagtgcttgttgcttg |
| | EGFR 762 to 823 | 251 | cgacgtaaaacgacggccagtNNNNNNNNNNNNNNCACACTGACGTGCCTCTCC | cacacaggaaacagctatgaccatgNNNNttatctcccctccccgtatc |
| | NRAS 001 to 014 | 275 | cgacgtaaaacgacggccagtNNNNNNNNNNNNNNGATTGTCAGTGCGCTTTTCC | cacacaggaaacagctatgaccatgNNNNgctaaggatggggttgcta |
| | PIK3CA 0272 to 347 | 279 | cgacgtaaaacgacggccagtNNNNNNNNNNNNNNTGACTTTACCTTATCAATGTCTCGAA | cacacaggaaacagctatgaccatgNNNNGCTCGCCCCCTTAATCTCT |
| #3 | PPP2R1A 176 to 217 | 277 | cgacgtaaaacgacggccagtNNNNNNNNNNNNNNGGTACTTCCGGAACCTGTGC | cacacaggaaacagctatgaccatgNNNNccgagtcctagggagaggag |
| | PTEN 056 to 070 | 250 | cgacgtaaaacgacggccagtNNNNNNNNNNNNNNttgttaatggtggctttttgttt | cacacaggaaacagctatgaccatgNNNNaaatgatctaacaatgctcttggac |
| | PTEN 165 to 211 | 265 | cgacgtaaaacgacggccagtNNNNNNNNNNNNNNcatggaaggatgagaatttcaag | cacacaggaaacagctatgaccatgNNNNtggctacgacccagttacca |
| | TP53 033 to 102 | 256 | cgacgtaaaacgacggccagtNNNNNNNNNNNNNNAAACCGTAGCTGCCCTGGTA | cacacaggaaacagctatgaccatgNNNNtgactgctcttttcacccatc |
| | TP53 225 to 260 | 257 | cgacgtaaaacgacggccagtNNNNNNNNNNNNNNtcatcttgggcctgtgttatc | cacacaggaaacagctatgaccatgNNNNgatgagaggtggatgggtagtagt |
| | EGFR 830 to 875 | 258 | cgacgtaaaacgacggccagtNNNNNNNNNNNNNNTTCAGGGCATGAACTACTTGG | cacacaggaaacagctatgaccatgNNNNatcctcccctgcatgtgtta |
| | KRAS 038 to 061 | 260 | cgacgtaaaacgacggccagtNNNNNNNNNNNNNNTCCCTCATTGCACTGTACTCC | cacacaggaaacagctatgaccatgNNNNggtgcttagtggccatttgt |
| | NRAS 038 to 062 | 250 | cgacgtaaaacgacggccagtNNNNNNNNNNNNNNTGGTCTCTCATGGCACTGTACT | cacacaggaaacagctatgaccatgNNNNattagcaatttgagggacaaacc |
| #4 | PTEN 071 to 084 | 250 | cgacgtaaaacgacggccagtNNNNNNNNNNNNNNtgtatctcactcgataatctggatgac | cacacaggaaacagctatgaccatgNNNNtgtcacattataaagattcaggcaat |
| | PTEN 213 to 267 | 271 | cgacgtaaaacgacggccagtNNNNNNNNNNNNNNagtttgacagttaaaggcatttcc | cacacaggaaacagctatgaccatgNNNNtgtccttattttggatatttctccc |
| | TP53 063 to 125 | 276 | cgacgtaaaacgacggccagtNNNNNNNNNNNNNNGAAGACCCAGGTCCAGATGA | cacacaggaaacagctatgaccatgNNNNagaaatgcaggggatacg |
| | TP53 262 To 306 | 280 | cgacgtaaaacgacggccagtNNNNNNNNNNNNNNgaggcataactgcacccttg | cacacaggaaacagctatgaccatgNNNNgggagtagatggagcctggt |
| | APC 1254 to 1325 | 269 | cgacgtaaaacgacggccagtNNNNNNNNNNNNNNtgctggatttggttctaggg | cacacaggaaacagctatgaccatgNNNNtgccacttgcaaagtttcttc |
| | APC 1403 to 1476 | 264 | cgacgtaaaacgacggccagtNNNNNNNNNNNNNNggaagaacctggaccctctg | cacacaggaaacagctatgaccatgNNNNttttgagagtcgttcgattgc |
| #5 | APC 1537 to 1617 | 289 | cgacgtaaaacgacggccagtNNNNNNNNNNNNNNtgcaacctgttttgtgatgg | cacacaggaaacagctatgaccatgNNNNaggaaaatgacaatgggaatga |
| | FBXW7 474 to 546 | 296 | cgacgtaaaacgacggccagtNNNNNNNNNNNNNNtgattcatcaggagagcatttaag | cacacaggaaacagctatgaccatgNNNNttgtttttctgtttctccctctg |
| | FBXW7 558 to 618 | 289 | cgacgtaaaacgacggccagtNNNNNNNNNNNNNNGATGGTATCCATGTGGTGAGTG | cacacaggaaacagctatgaccatgNNNNtttgtgatgctaaggctccat |
| | TP53 001 to 24 | 254 | cgacgtaaaacgacggccagtNNNNNNNNNNNNNNactgccttccgggtcact | cacacaggaaacagctatgaccatgNNNNagcccaacccttgtccttac |
| | TP53 368 To 393 | 265 | cgacgtaaaacgacggccagtNNNNNNNNNNNNNNgaggctgtcagtggggaac | cacacaggaaacagctatgaccatgNNNNaacatatttgcatggggtgtg |
| | APC 1326 to 1405 | 283 | cgacgtaaaacgacggccagtNNNNNNNNNNNNNNccactgcatggttcactctg | cacacaggaaacagctatgaccatgNNNNatcctgtgagcgaagttcca |
| | APC 1475 to 1545 | 264 | cgacgtaaaacgacggccagtNNNNNNNNNNNNNNtgcctctttctcttggttttca | cacacaggaaacagctatgaccatgNNNNggacctaagcaagctgcagtaa |
| | FBXW7 243 to 287 | 257 | cgacgtaaaacgacggccagtNNNNNNNNNNNNNNacacccaatgaagaatgtaattgat | cacacaggaaacagctatgaccatgNNNNggtgtgtgtagatgtgagttttcc |
| #6 | FBXW7 329 to 374 | 276 | cgacgtaaaacgacggccagtNNNNNNNNNNNNNNtctgttacattgtgcagagttca | cacacaggaaacagctatgaccatgNNNNtggttttgagcagagagatgg |
| | FBXW7 413 to 472 | 266 | cgacgtaaaacgacggccagtNNNNNNNNNNNNNNggaagaagtcccaaccatga | cacacaggaaacagctatgaccatgNNNNtcacttttccttttctacccaaaag |
| | FBXW7 549 to 593 | 259 | cgacgtaaaacgacggccagtNNNNNNNNNNNNNNGAATCTGCATTCCCAGAGACA | cacacaggaaacagctatgaccatgNNNNcctgtttcccatctctttcc |
| | KRAS 134 to 150 | 267 | cgacgtaaaacgacggccagtNNNNNNNNNNNNNNGACACAAAACAGGCTCAGGAC | cacacaggaaacagctatgaccatgNNNNagaaaccaaagccaaaagca |
| | TP53 026 to 32 | 253 | cgacgtaaaacgacggccagtNNNNNNNNNNNNNNccatgggactgactttctgc | cacacaggaaacagctatgaccatgNNNNtcatctggacctgggtcttc |

Fig. 10

Table S6. Mutations Identified in Pap Smears through Simultaneous Assessment of 12 Genes

| Case # | Tumor Type | Mutated Gene Name | Mutated Gene ID | Nucleotide (genomic)* | Transcript | Nucleotide (transcript)* | Amino Acid (protein) | Mutation Type | Fraction of mutant alleles in Pap smear fluid |
|---|---|---|---|---|---|---|---|---|---|
| PAP 001 | Endometrial | KRAS | ENSG00000133703 | g.chr12:25289551C>G | CCDS8703.1 | c.35G>C | p.G12A | Missense | 12.51% |
| | | PIK3CA | ENSG00000121879 | g.chr3:180434779A>G | CCDS43171.1 | c.3140A>G | p.H1047R | Missense | 5.74% |
| PAP 003 | Endometrial | PIK3CA | ENSG00000121879 | g.chr3:180399570G>A | CCDS43171.1 | c.263G>A | p.R88Q | Missense | 11.60% |
| | | APC | ENSG00000134982 | g.chr5:112203538C>T | CCDS4107.1 | c.4348C>T | p.R1450X | Missense | 12.50% |
| | | PTEN | ENSG00000171862 | g.chr10:89614243A>C | CCDS31238.1 | c.38A>C | p.K13T | Missense | 12.38% |
| PAP 010 | Endometrial | FBXW7 | ENSG00000109670 | g.chr4:153466817G>A | CCDS3777.1 | c.1435C>T | p.R479X | Nonsense | 20.00% |
| PAP 011 | Endometrial | KRAS | ENSG00000133703 | g.chr12:25289551C>G | CCDS8703.1 | c.35G>C | p.G12A | Missense | 3.23% |
| PAP 025 | Endometrial | TP53 | ENSG00000141510 | g.chr17:7520119_7520120delGG | CCDS11118.1 | c.292_293delCC | Frameshift | Indel | 10.42% |
| PAP 033 | Endometrial | PIK3CA | ENSG00000121879 | g.chr3:180404243T>G | CCDS43171.1 | c.1031T>G | p.V344G | Missense | 1.22% |
| | | KRAS | ENSG00000133703 | g.chr12:25289551C>A | CCDS8703.1 | c.35G>T | p.G12V | Missense | 1.13% |
| | | PTEN | ENSG00000171862 | g.chr10:89707637insC | CCDS31238.1 | c.682insC | Frameshift | Indel | 0.87% |
| PAP 34 | Endometrial | PIK3CA | ENSG00000121879 | g.chr3:180399630G>A | CCDS43171.1 | c.323G>A | p.R108H | Missense | 22.78% |
| | | CTNNB1 | ENSG00000168036 | g.chr3:41241107G>A | CCDS2694.1 | c.100G>A | p. G34R | Missense | 18.41% |
| | | PTEN | ENSG00000171862 | g.chr10:89707750delA | CCDS31238.1 | c.795delA | Frameshift | Indel | 13.28% |
| | | PIK3CA | ENSG00000121879 | g.chr3:180399554T>G | CCDS43171.1 | c.247T>G | p.F83V | Missense | 4.49% |
| | | KRAS | ENSG00000133703 | g.chr12:25289551C>T | CCDS8703.1 | c.35G>A | p.G12D | Missense | 0.92% |
| PAP 35 | Endometrial | KRAS | ENSG00000133703 | g.chr12:25289551C>T | CCDS8703.1 | c.35G>A | p.G12D | Missense | 5.83% |
| | | PIK3CA | ENSG00000121879 | g.chr3:180399548G>A | CCDS43171.1 | c.241G>A | p.E81K | Missense | 5.32% |
| | | PTEN | ENSG00000171862 | g.chr10:89675287T>C | CCDS31238.1 | c.202T>C | p.Y68H | Missense | 4.73% |
| PAP 39 | Ovarian | TP53 | ENSG00000141510 | g.chr17:7518244delG | CCDS11118.1 | c.871delC | Frameshift | Indel | 0.73% |
| PAP 67 | Endometrial | TP53 | ENSG00000141510 | g.chr17:7518937G>A | CCDS11118.1 | c.637C>T | p.R213X | Nonsense | 2.31% |
| PAP 69 | Endometrial | TP53 | ENSG00000141510 | g.chr17:7520084G>A | CCDS11118.1 | c.328C>T | p.R110C | Missense | 19.23% |
| | | TP53 | ENSG00000141510 | g.chr17:7517747G>A | CCDS11118.1 | c.916C>T | p.R306X | Nonsense | 13.60% |
| PAP 70 | Endometrial | PIK3CA | ENSG00000121879 | g.chr3:180399570G>A | CCDS43171.1 | c.263G>A | p.R88Q | Missense | 28.05% |
| PAP 71 | Endometrial | KRAS | ENSG00000133703 | g.chr12:25289551C>T | CCDS8703.1 | c.35G>A | p.G12D | Missense | 0.39% |
| | | PIK3CA | ENSG00000121879 | g.chr3:180434779A>G | CCDS43171.1 | c.3140A>G | p.H1047R | Missense | 0.31% |
| PAP 72 | Ovarian | TP53 | ENSG00000141510 | g.chr17:7518272C>T | CCDS11118.1 | c.734G>A | p.G245D | Missense | 0.54% |

*Coordinates refer to the human reference genome hg18 release (NCBI 36.1, March 2006).

Fig. 11

PAPANICOLAOU TEST FOR OVARIAN AND ENDOMETRIAL CANCERS

This invention was made with government support under grant no. CA043460, CA062924, CN043309, and CA129825 awarded by the National Institutes of Health. The government has certain rights in the invention.

This invention was made using funds from the National Cancer Institute and the National Institutes of Health. The U.S. government retains certain rights under the terms of NCI contract N01-CN-43309 and NIH grants CA129825 and CA43460.

TECHNICAL FIELD OF THE INVENTION

This invention is related to the area of cancer screening. In particular, it relates to ovarian and endometrial cancers.

BACKGROUND OF THE INVENTION

Since the introduction of the Papanicolaou test, the incidence and mortality of cervical cancer in screened populations has been reduced by more than 75% (1, 2). In contrast, deaths from ovarian and endometrial cancers have not substantially decreased during that same time period. As a result, more than 69,000 women in the U.S. will be diagnosed with ovarian and endometrial cancer in 2012. Although endometrial cancer is more common than ovarian cancer, the latter is more lethal. In the U.S., approximately 15,000 and 8,000 women are expected to die each year from ovarian and endometrial cancers, respectively (Table 1). World-wide, over 200,000 deaths from these tumors are expected this year alone (3, 4).

In an effort to replicate the success of cervical cancer screening, several approaches for the early detection of endometrial and ovarian cancers have been devised. For endometrial cancers, efforts have focused on cytology and transvaginal ultrasound (TVS). Cytology can indeed indicate a neoplasm within the uterus in some cases, albeit with low specificity (5). TVS is a noninvasive technique to measure the thickness of the endometrium based on the fact that endometria harboring a cancer are thicker than normal endometria (6). As with cytology, screening measurement of the endometrial thickness using TVS lacks sufficient specificity because benign lesions, such as polyps, can also result in a thickened endometrium. Accordingly, neither cytology nor TVS fulfills the requirements for a screening test (5, 7).

Even greater efforts have been made to develop a screening test for ovarian cancer, using serum CA-125 levels and TVS. CA-125 is a high molecular weight transmembrane glycoprotein expressed by coelomic- and Müllerian-derived epithelia that is elevated in a subset of ovarian cancer patients with early stage disease (8). The specificity of CA-125 is limited by the fact that it is also elevated in a variety of benign conditions, such as pelvic inflammatory disease, endometriosis and ovarian cysts (9). TVS can visualize the ovary but can only detect large tumors and cannot definitively distinguish benign from malignant tumors. Several clinical screening trials using serum CA-125 and TVS have been conducted but none has shown a survival benefit. In fact, some have shown an increase in morbidity compared to controls because false positive tests elicit further evaluation by laparoscopy or exploratory laparotomy (10-12).

Accordingly, the U.S. Preventative Services Task Force, the American Cancer Society, the American Congress of Obstetricians and Gynecologists, as well as the National Comprehensive Cancer Network, do not recommend routine screening for endometrial or ovarian cancers in the general population. In fact, these organizations warn that "the potential harms outweigh the potential benefits" (13-16). An exception to this recommendation has been made for patients with a hereditary predisposition to ovarian cancer, such as those with germline mutations in a BRCA gene or those with Lynch syndrome. It is recommended that BRCA mutation carriers be screened every 6 months with TVS and serum CA-125, starting at a relatively early age. Screening guidelines for women with Lynch syndrome include annual endometrial sampling and TVS beginning between age 30 and 35 (15, 17).

The mortality associated with undetected gynecologic malignancies has made the development of an effective screening tool a high priority. An important observation that inspired the current study is that asymptomatic women occasionally present with abnormal glandular cells (AGCs) detected in a cytology specimen as part of their routine cervical cancer screening procedure. Although AGCs are associated with premalignant or malignant disease in some cases (18-22), it is often difficult to distinguish the AGCs arising from endocervical, endometrial or ovarian cancer from one another or from more benign conditions. There is a continuing need in the art to detect these cancers at an earlier stage than done currently.

SUMMARY OF THE INVENTION

According to one aspect of the invention a method is provided for detecting or monitoring endometrial or ovarian cancer. A liquid Pap smear of a patient is tested for a genetic or epigenetic change in one or more genes, mRNAs, or proteins mutated in endometrial or ovarian cancer. Detection of the change indicates the presence of such a cancer in the patient.

According to another aspect of the invention a method is provided for screening for endometrial and ovarian cancers. A liquid Pap smear is tested for one or more mutations in a gene, mRNA, or protein selected from the group consisting of CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2. Detection of the mutation indicates the presence of such a cancer in the patient.

Another aspect of the invention is a kit for testing a panel of genes in Pap smear samples for ovarian or endometrial cancers. The kit comprises at least 10 probes or at least 10 primer pairs. Each probe or primer comprises at least 15 nt of complementary sequence to one of the panel of genes. At least 10 different genes are interrogated. The panel is selected from the group consisting of CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2.

Still another aspect of the invention is a solid support comprising at least 10 attached probes. Each probe comprises at least 15 nt of complementary sequence to one of a panel of genes, wherein the panel is selected from the group consisting of CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2.

Another aspect of the invention is a solid support comprising at least 10 primers attached thereto. Each primer comprises at least 15 nt of complementary sequence to one of a panel of genes. The panel is selected from the group consisting of CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2.

These and other embodiments which will be apparent to those of skill in the art upon reading the specification provide the art with methods for assessing ovarian and endometrial cancers in a screening environment using samples that are already routinely collected.

BRIEF DESCRIPTION OF THE DRAWINGS

FIG. 5. Table 1. Epidemiology of Ovarian and Endometrial Tumors. The estimated numbers of new cases and deaths in the U.S. from the major subtypes of ovarian and endometrial cancers are listed.

FIG. 6. Table 2. Genetic Characteristics of Ovarian and Endometrial Cancers. The frequencies of the commonly mutated genes in ovarian and endometrial cancers are listed.

FIG. 7. Table S1. Endometrial Cancers (Endometrioid Subtype) Studied by Whole-exome Sequencing. The summary characteristics of the 22 cancers used for exome sequencing are listed.

FIG. 8. Table S3. Mutations Assessed in Pap Smears. Clinical characteristics of the 46 tumor samples are listed, along with the mutation identified in each case and the fraction of mutant alleles identified in the Pap smears.

FIG. 9. Table S4. Primers Used to Assess Individual Mutations in Pap Smears. The sequences of the forward and reverse primers used to test each mutation via Safe-SeqS are listed in pairs (SEQ ID NO: 4-99, respectively).

FIG. 10. Table S5. Primers Used to Simultaneously Assess 12 Genes in Pap Smears. The sequences of the forward and reverse primers for each tested region are listed in pairs (SEQ ID NO: 100-191, respectively).

FIG. 11. Table S6. Mutations Identified in Pap Smears through Simultaneous Assessment of 12 Genes. The fraction of mutant alleles identified in the Pap smears using this approach is listed, along with the precise mutations identified.

DETAILED DESCRIPTION OF THE INVENTION

Figure 1:
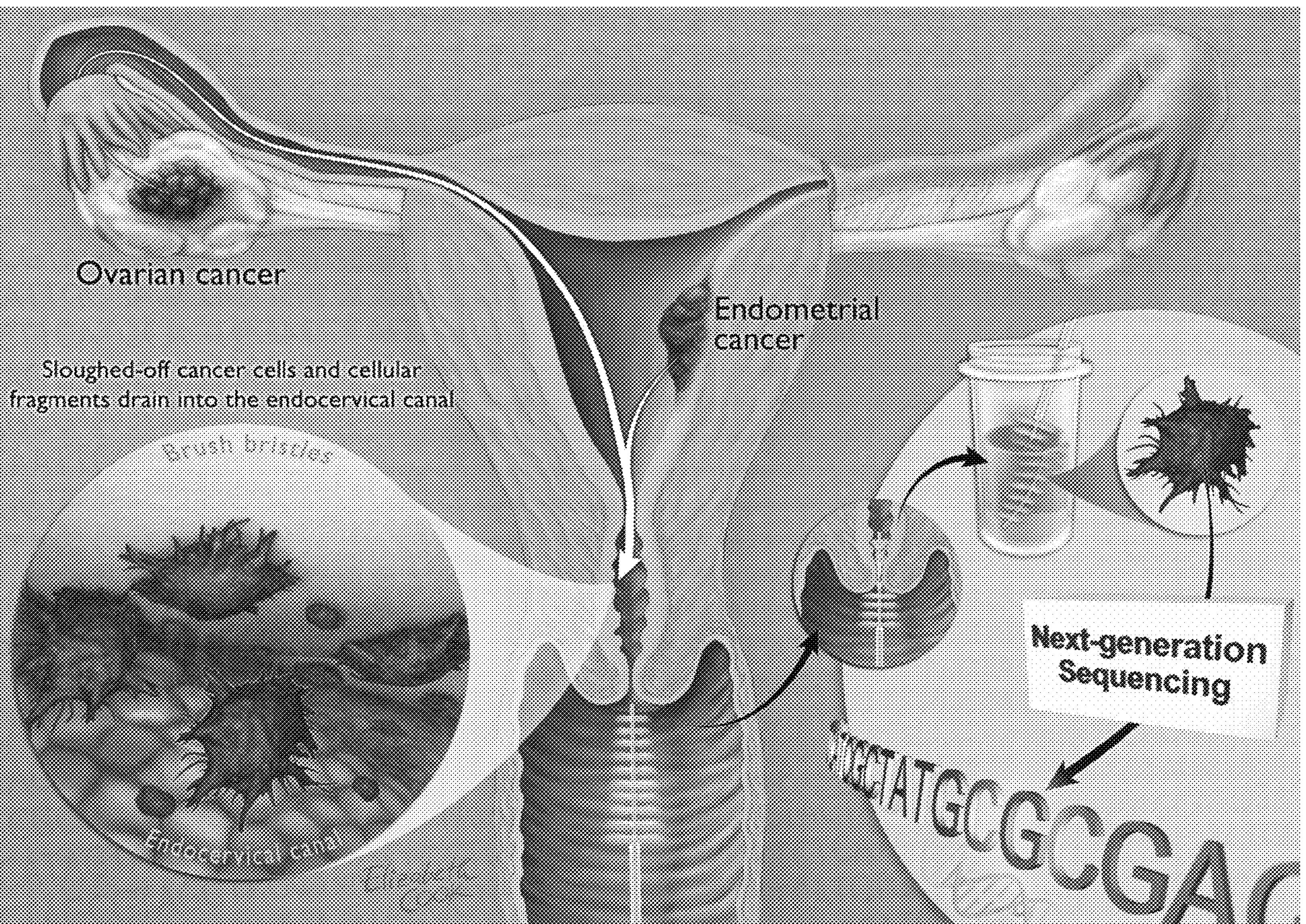
FIG. 1. Schematic demonstrating the principle steps of the procedure described in this study. Tumors cells shed from ovarian or endometrial cancers are carried into the endocervical canal. These cells can be captured by the brush used for performing a routine Pap smear. The brush contents are transferred into a liquid fixative, from which DNA is isolated. Using next-generation sequencing, this DNA is queried for mutations that indicate the presence of a malignancy in the female reproductive tract.

The inventors have developed a test for detecting different cancers using samples that are already routinely collected for diagnosing uterine cancer and HPV (human papilloma virus) infection. Using a panel of genes, a high level of detection of both endometrial and ovarian cancers was achieved.

Certain genes have been identified as mutated in a high proportion of endometrial and ovarian cancers. These include CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2. The test can be performed on at least 3, 4, 5, 6, 7, 8, 9, 10, 11, 12, 13, 14, 15, 16, or 17 of these genes. In addition, other genes can be added or substituted into the panel to achieve a higher rate of detection.

Testing for a mutation may be done by analysis of nucleic acids, such as DNA or mRNA or cDNA. The nucleic acid analytes are isolated from cells or cell fragments found in the liquid PAP smear sample. Suitable tests may include any hybridization or sequencing based assay. Analysis may also be performed on protein encoded by the genes in the panel. Any suitable test may be used including but not limited to mass spectrometry. Other suitable assays may include immunological assays, such as, immunoblotting, immunocytochemistry, immunoprecipitation, enzyme-linked immunosorbent assay (ELISA), radioimmunoassay (RIA), immunoradiometric assays (IRMA) and immunoenzymatic assays (IEMA), including sandwich assays using monoclonal or polyclonal antibodies.

Genetic changes which can be detected are typically mutations such as deletions, insertions, duplications, substitutions (missense or nonsense mutations), rearrangements, etc. Such mutations can be detected inter alia by comparing to a wild type in another (non-tumor) tissue or fluid of an individual or by comparing to reference sequences, for example in databases. Mutations that are found in all tissues of an individual are germline mutations, whereas those that occur only in a single tissue are somatic mutations. Epigenetic changes can also be detected. These may be loss or gain of methylation at specific locations in specific genes, as well as histone modifications, including acetylation, ubiquitylation, phosphorylation and sumoylation.

Tests may be done in a multiplex format, in which a single reaction pot is used to detect multiple analytes. Examples of such tests include amplifications using multiple primer sets, amplifications using universal primers, array based hybridization or amplification, emulsion based amplification.

While probes and primers may be designed to interrogate particular mutations or particular portions of a gene, mRNA, or cDNA, these may not be separate entities. For example, probes and primers may be linked together to form a concatamer, or they may be linked to one or more solid supports, such as a bead or an array.

Kits for use in the disclosed methods may include a carrier for the various components. The carrier can be a container or support, in the form of, e.g., bag, box, tube, rack, and is optionally compartmentalized. The kit also includes various components useful in detecting mutations, using the above-discussed detection techniques. For example, the detection kit may include one or more oligonucleotides useful as primers for amplifying all or a portion of the target nucleic acids. The detection kit may also include one or more oligonucleotide probes for hybridization to the target nucleic acids. Optionally the oligonucleotides are affixed to a solid support, e.g., incorporated in a microarray included in the kit or supplied separately.

Solid supports may contain one single primer or probe or antibody for detecting a single gene, protein, mRNA, or portion of a gene. A solid support may contain multiple primers, probes, or antibodies. They may be provided as a group which will interrogate mutations at least 3, 4, 5, 6, 7, 8, 9, 10, 11, 12, 13, 14, 15, 16, or 17 of the genes of the desired panel. The panel may be selected from or comprise CTNNB1, EGFR, PI3KCA, PTEN, TP53, BRAF, KRAS, AKT1, NRAS, PPP2R1A, APC, FBXW7, ARID1A, CDKN2A, MLL2, RFF43, and FGFR2.

Primer pairs may be used to synthesize amplicons of various sizes. Amplicons may be for example from 50, 60, 75, 100, 125, 150, 200, 140, 180 bp in length. Amplicons may run up to 200, 250, 300, 400, 500, 750, 1000 bp in length, as examples. The size of the amplicon may be limited by the size and/or quality of the template retrieved from the liquid PAP smear. Probes and primers for use in the invention may contain a wild-type sequence or may contain a sequence of a particular mutant.

In one embodiment, the test can be performed using samples that are collected over time. The test results can be compared for quantitative or qualitative changes. Such analysis can be used after a potentially curative therapy, such as surgery.

Georgios Papanicolaou published his seminal work, entitled "Diagnosis of Uterine Cancer by the Vaginal Smear," in 1943 (31). At that time, he suggested that endocervical sampling could, in theory, be used to detect not only cervical cancers but also other cancers arising in the female reproductive tract, including endometrial carcinomas. The research reported here moves us much closer to that goal. In honor of Papanicolaou's pioneering contribution to the field of early cancer detection, we have named the approach described herein as the "PapGene" test.

One of the most important developments over the last several years is the recognition that all human cancers are the result of mutations in a limited set of genes and an even more limited set of pathways through which these genes act (32). The whole-exome sequencing data we present, combined with previous genome-wide studies, provide a striking example of the common genetic features of cancer (FIG. 6, Table 2). Through the analysis of particular regions of only 12 genes (FIG. 11, table S5), we could detect at least one driver mutation in the vast majority of nine different gynecologic cancers (FIG. 5, Table 1). Though several of these 12 genes were tumor suppressors, and therefore difficult to therapeutically target, knowledge of their mutational patterns provides unprecedented opportunities for cancer diagnostics.

The most important finding in this paper is that significant amounts of cells or cell fragments from endometrial and ovarian cancers are present in the cervix and can be detected through molecular genetic approaches. Detection of malignant cells from endometrial and ovarian carcinomas in cervical cytology specimens is relatively uncommon. Microscopic examination cannot always distinguish them from one another, from cervical carcinomas, or from more benign conditions. Our study showed that 100% of endometrial cancers (n=24), even those of low grade, and 41% of ovarian cancers (n=22), shed cells into the cervix that could be detected from specimens collected as part of routine Pap smears. This finding, in conjunction with technical advances allowing the reliable detection of mutations present in only a very small fraction of DNA templates, provided the foundation for the PapGene test.

Figure 3:
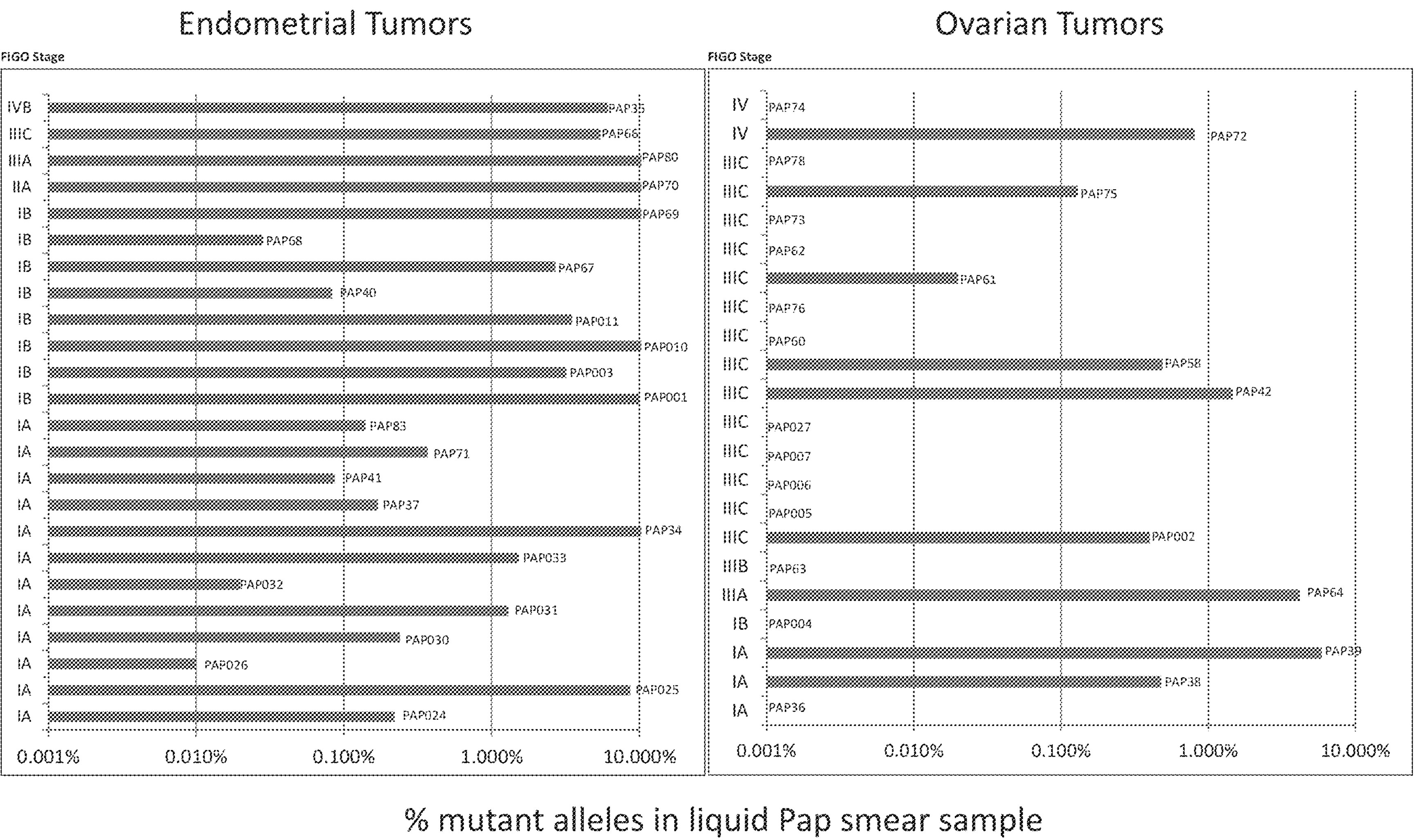
FIG. 3. Mutant allele fractions in Pap smear fluids. The fraction of mutant alleles from each of 46 pap smear fluids is depicted. The stage of each tumor is listed on the Y-axis. The X-axis demonstrates the % mutant allele fraction as determined by Safe-SeqS.

This study demonstrates the value of sensitive endocervical DNA testing but there are many issues that need to be addressed before optimal clinical use is achieved. The test, even in its current format, appears to be promising for screening endometrial cancer, as the data in FIG. 3 show that even the lowest stage endometrial cancers could be detected through the analysis of DNA in Pap smear fluid through Safe-SeqS. However, only 41% of ovarian cancers could be detected in Pap smears even when the mutations in their tumors were known. In eight of the nine Pap smears from ovarian cancer patients that contained detectable mutations, the mutant allele fractions were >0.1% and therefore within the range currently detectable by PapGene testing (FIG. 9, table S3). Further improvements in the technology could increase the technical sensitivity of the PapGene test and allow it to detect more ovarian cancers. Other strategies to increase this sensitivity involve physical maneuvers, such as massaging the adnexal region during the pelvic examination or by performing the PapGene test at specified times during the menstrual cycle. Development of an improved method of collection may also be able to improve sensitivity. The current liquid specimen is designed for the detection of cervical cancer and as such utilizes a brush that collects cells from the ectocervix and only minimally penetrates the endocervical canal. A small cannula that can be introduced into the endometrial cavity similar to the pipelle endometrial biopsy instrument could theoretically obtain a more enriched sample of cells coming from the endometrium, fallopian tube and ovary (33).

The high sensitivity and the quantitative nature of the PapGene test also opens the possibility of utilizing it to monitor the response to hormonal agents (e.g., progestins) used to treat young women with low risk endometrial cancers. Some of these women choose to preserve fertility, undergoing medical therapy rather than hysterectomy (34). The detection of pre-symptomatic ovarian cancers, even if advanced, could also be of benefit. Although not entirely analogous, it has been demonstrated that one of the most important prognostic indicators for ovarian cancer is the amount of residual disease after surgical debulking Initially, debulking was considered optimal if the residual tumor was less than 2 cm. Subsequently, the threshold was reduced to 1 cm and surgeons now attempt to remove any visible tumor. With each improvement in surgical debulking, survival has lengthened (35). A small volume of tumor is likely to be more sensitive to cytotoxic chemotherapy than the large, bulky disease typical of symptomatic high-grade serous carcinoma.

An essential aspect of the screening approach described here is that it should be relatively inexpensive and easily incorporated into the pelvic examination. Evaluation of HPV DNA is already part of routine Pap smear testing because HPV analysis increases the test's sensitivity (36, 37). The DNA purification component of the PapGene test is identical to that used for HPV, so this component is clearly feasible. The preparation of DNA, multiplex amplification, and the retail cost of the sequencing component of the PapGene test can also be performed at a cost comparable to a routine HPV test in the U.S. today. Note that the increased sensitivity provided by the Safe-SeqS component of the PapGene test (see Example 6) can be implemented on any massively parallel sequencing instrument, not just those manufactured by Illumina. With the reduction in the cost of massively parallel sequencing expected in the future, PapGene testing should become even less expensive.

There are millions of Pap smear tests performed annually in the U.S. Could PapGene testing be performed on such a large number of specimens? We believe so, because the entire DNA purification and amplification process can be automated, just as it is for HPV testing. Though it may now seem unrealistic to have millions of these sophisticated sequence-based tests performed every year, it would undoubtedly have seemed unrealistic to have widespread, conventional Pap smear testing performed when Papanicolaou published his original paper (31). Even today, when many cervical cytology specimens are screened using automated technologies, a significant percentage require evaluation by a skilled cytopathologist. In contrast, the analysis of PapGene testing is done completely in silico and the readout of the test is objective and quantitative.

In sum, PapGene testing has the capacity to increase the utility of conventional cytology screening through the unambiguous detection of endometrial and ovarian carcinomas. In addition to the analysis of much larger numbers of patients with and without various types of endometrial, ovarian, and fallopian tube cancers, the next step in this line of research is to include genes altered in cervical cancer as well as HPV amplicons in the multiplexed Safe-SeqS assay (FIG. 11, table S5). These additions will provide information that could be valuable for the management of patients with the early stages of cervical neoplasia, as HPV positivity alone is not specific for the detection of cervical cancer and its precursor lesions, particularly in young, sexually active women who frequently harbor HPV infections in the absence of neoplasia.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

We reasoned that more sophisticated molecular methods might be able to detect the presence of cancer cells in endocervical specimens at higher sensitivities and specificities than possible with conventional methods. In particular, we hypothesized that somatic mutations characteristic of endometrial and ovarian cancers would be found in the DNA purified from routine liquid-based Pap smears (henceforth denoted as "Pap smears"; FIG. 1). Unlike cytologically abnormal cells, such oncogenic DNA mutations are specific, clonal markers of neoplasia that should be absent in non-neoplastic cells. However, we did not know if such DNA would indeed be present in endocervical specimens, and we did not know if they would be present in a sufficient amount to detect them. The experiments described here were carried out to test our hypothesis.

There were four components to this study: I. Determination of the somatic mutations typically present in endometrial and ovarian cancers; II. Identification of at least one mutation in the tumors of 46 patients with these cancers; III. Determination of whether the mutations identified in these tumors could also be detected in Pap smears from the same patients; and IV. Development of a technology that could directly assess cells from Pap smears for mutations commonly found in endometrial or ovarian cancers.

Example 2

Prevalence of Somatically Mutated Genes in Endometrial and Ovarian Cancers

There are five major histopathologic subtypes of ovarian cancers. The most prevalent subtype is high grade serous (60% of total), followed by endometrioid (15%), clear cell (10%), and low-grade serous carcinoma (8%) (Table 1). Genome-wide studies have identified the most commonly mutated genes among the most prevalent ovarian cancer subtypes (Table 2) (23-25).

Such comprehensive studies have not yet been reported for the endometrioid and mucinous subtypes, collectively representing ~20% of ovarian cancer cases (Table 1). However, commonly mutated genes in the endometrioid and mucinous subtypes have been reported (26). In aggregate, the most commonly mutated gene in epithelial ovarian cancers was TP53, which was mutated in 69% of these cancers (Table 2). Other highly mutated genes included ARID1A, BRAF, CTNNB1, KRAS, PIK3CA, and PPP2R1A (Table 2).

Among endometrial cancers, the endometrioid subtype is by far the most common, representing 85% of the total (Table 1). Because cancers of this subtype are so frequent and have not been analyzed at a genome-wide level, we evaluated them through whole-exome sequencing. The DNA purified from 22 sporadic endometrioid carcinomas, as well as from matched non-neoplastic tissues, was used to generate 44 libraries suitable for massively parallel sequencing. The clinical aspects of the patients and histopathologic features of the tumors are listed in table S1. Though the examination of 22 cancers cannot provide a comprehensive genome landscape of a tumor type, it is adequate for diagnostic purposes—as these only require the identification of the most frequently mutated genes.

Among the 44 libraries, the average coverage of each base in the targeted region was 149.1 with 88.4% of targeted bases represented by at least ten reads. Using stringent criteria for the identification of somatic mutations (as described in Materials and Methods), the sequencing data clearly demarcated the tumors into two groups: ten cancers (termed the N Group, for non-highly mutated) harbored <100 somatic mutations per tumor (median 32, range 7 to 50), while 12 cancers (termed the H Group, for highly mutated) harbored >100 somatic mutations per tumor (median 674, range 164 to 4,629) (FIG. 7, table S1).

The high number of mutations in the Group H tumors was consistent with a deficiency in DNA repair. Eight of the 12 Group H tumors had microsatellite instability (MSI-H, table S1), supporting this conjecture. Moreover, six of the Group H tumors contained somatic mutations in the mismatch repair genes MSH2 or MSH6, while none of the Group N cancers contained mutations in mismatch repair genes. Mismatch repair deficiency is known to be common among endometrial cancers and these tumors occur in 19-71% of women with inherited mutations of mismatch repair genes (i.e., patients with the Hereditary Nonpolyposis Colorectal Cancer) (27).

12,795 somatic mutations were identified in the 22 cancers. The most commonly mutated genes included the PIK3 pathway genes PTEN and PIK3CA (28), the APC pathway genes APC and CTNNB1, the fibroblast growth factor receptor FGFR2, the adapter protein FBXW7, and the chromatin-modifying genes ARID1A and MLL2 (Table 2). Genes in these pathways were mutated in both Group N and H tumors. Our results are consistent with prior studies of endometrioid endometrial cancer that had evaluated small numbers of genes, though mutations in FBXW7, MLL2 and APC had not been appreciated to occur as frequently as we found them. It was also interesting that few TP53 mutations (5%) were found in these endometrial cancers (Table 2), a finding also consistent with prior studies.

Papillary serous carcinomas of the endometrium account for 10-15% of endometrial cancers, and a recent genome-wide sequencing study of this tumor subtype has been published (29). The most common mutations in this subtype are listed in Table 2. The least common subtype of endometrial cancers is clear cell carcinomas, which occur in <5%. Genes reported to be mutated in these cancers were garnered from the literature (Table 2).

Example 3

Identification of Mutations in Tumor Tissues

We acquired tumors from 46 cancer patients in whom Pap smears were available. These included 24 patients with endometrial cancers and 22 with ovarian cancers; clinical and histopathologic features are listed in table S3.

Somatic mutations in the 46 tumors were identified through whole-exome sequencing as described above or through targeted sequencing of genes frequently mutated in the most common subtypes of ovarian or endometrial cancer (Table 2). Enrichment for these genes was achieved using a custom solid phase capture assay comprised of oligonucleotides ("capture probes") complementary to a panel of gene regions of interest. For the oncogenes, we only targeted their commonly mutated exons, whereas we targeted the entire coding regions of the tumor suppressor genes.

Illumina DNA sequencing libraries were generated from tumors and their matched non-neoplastic tissues, then captured with the assay described above. Following amplification by PCR, four to eight captured DNA libraries were sequenced per lane on an Illumina GA IIx instrument. In each of the 46 cases, we identified at least one somatic mutation (table S3) that was confirmed by an independent assay, as described below.

Example 4

Identification of Somatic Mutations in Pap Smears

In the liquid-based Pap smear technique in routine use today, the clinician inserts a small brush into the endocervical canal during a pelvic exam and rotates the brush so that it dislodges and adheres to loosely attached cells or cell fragments. The brush is then placed in a vial of fixative solution (e.g., ThinPrep). Some of the liquid from the vial is used to prepare a slide for cytological analysis or for purification of HPV DNA. In our study, an aliquot of the DNA purified from the liquid was used to assess for the presence of DNA from the cancers of the 46 patients described above. Preliminary studies showed that the fixed cells or cell fragments in the liquid, pelleted by centrifugation at 1,000 g for five minutes, contained >95% of the total DNA in the vial. We therefore purified DNA from the cell pellets when the amount of available liquid was greater than 3 mL (as occurs with some liquid-based Pap smear kits) and, for convenience, purified DNA from both the liquid and cells when smaller amounts of liquid were in the kit. In all cases, the purified DNA was of relatively high molecular weight (95%>5 kb). The average amount of DNA recovered from the 46 Pap smears was 49.3±74.4 ng/ml (table S3).

Figure 2:
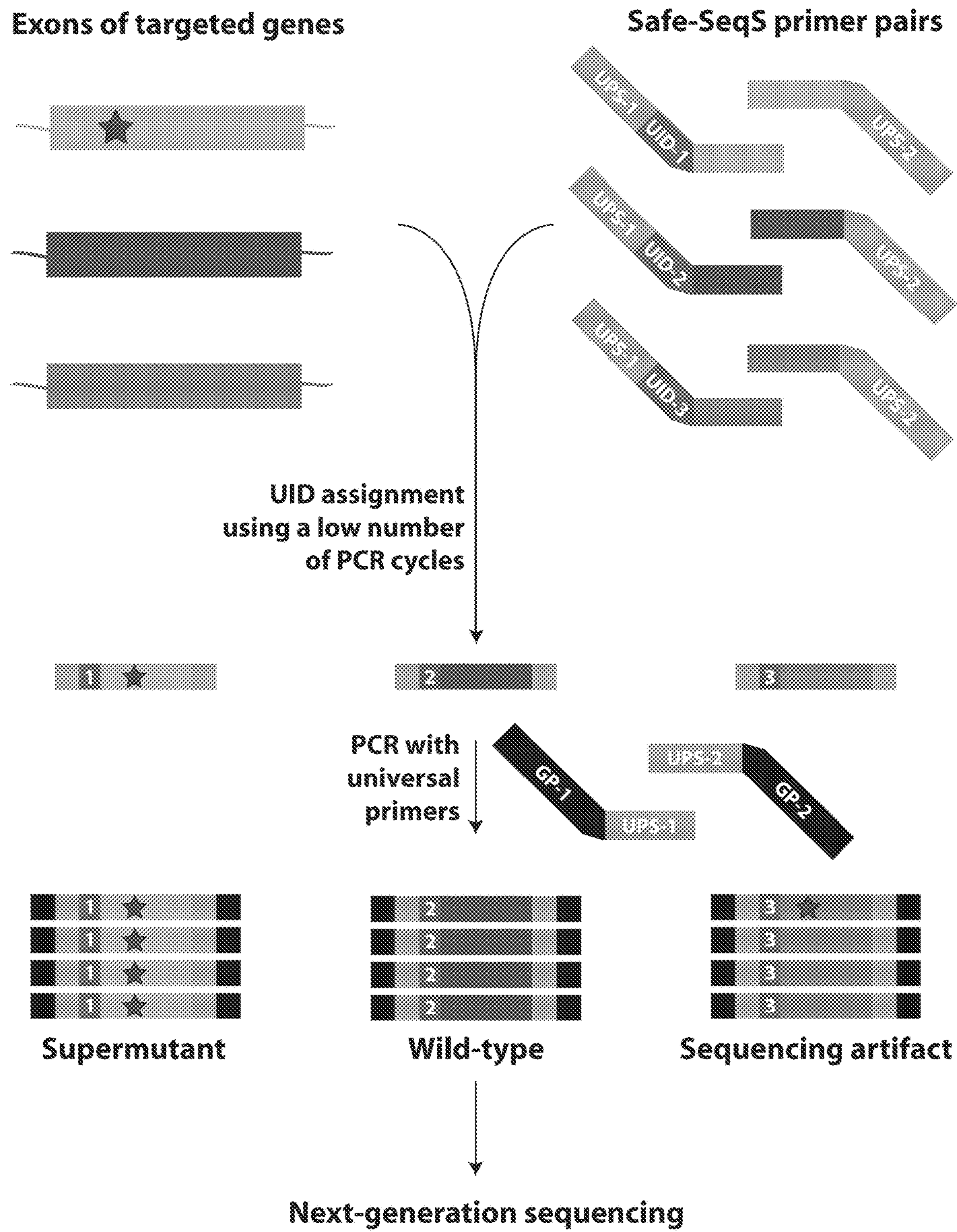
FIG. 2. Diagram of the assay used to simultaneously detect mutations in 12 different genes. A modification of the Safe-SeqS (Safe-Sequencing System) protocol, for simultaneous interrogation of multiple mutations in a single sample, is depicted. In the standard Safe-SeqS procedure, only one amplicon is assessed, while the new system is used to assess multiple amplicons from multiple genes at once.

We anticipated that, if present at all, the amount of DNA derived from neoplastic cells in the Pap smear fluid would be relatively small compared to the DNA derived from normal cells brushed from the endocervical canal. This necessitated the use of an analytic technique that could reliably identify a rare population of mutant alleles among a great excess of wild-type alleles. A modification of one of the Safe-SeqS (Safe-Sequencing System) procedures described in (30) was designed for this purpose (FIG. 2).

In brief, a limited number of PCR cycles was performed with a set of gene-specific primers. One of the primers contained 14 degenerate N bases (equal probability of being an A, C, G, or T) located 5' to its gene-specific sequence, and both primers contained sequences that permitted universal amplification in the next step. The 14 N's formed unique identifiers (UID) for each original template molecule. Subsequent PCR products generated with universal primers were purified and sequenced on an Illumina MiSeq instrument. If a mutation preexisted in a template molecule, that mutation should be present in every daughter molecule containing that UID, and such mutations are called "supermutants" (30). Mutations not occurring in the original templates, such as those occurring during the amplification steps or through errors in base calling, should not give rise to supermutants. The Safe-SeqS approach used here is capable of detecting 1 mutant template among 5,000 to 1,000,000 wild-type templates, depending on the amplicon and the position within the amplicon that is queried (30).

We designed Safe-SeqS primers (table S4) to detect at least one mutation from each of the 46 patients described in table S3. In the 24 Pap smears from patients with endometrial cancers, the mutation present in the tumor was identified in every case (100%). The median fraction of mutant alleles was 2.7%, and ranged from 0.01% to 78% (FIG. 3 and table S3). Amplifications of DNA from non-neoplastic tissues were used as negative controls in these experiments to define the detection limits of each queried mutation. In all cases, the fraction of mutant alleles was significantly different from the background mutation levels determined from the negative controls ($P<0.001$, binomial test). There was no obvious correlation between the fraction of mutant alleles and the histopathologic subtype or the stage of the cancer (FIG. 3 and table S3).

In two endometrial cancer cases, two mutations found in the tumor DNA were evaluated in the Pap smears (table S3). In both cases, the mutations were identified in DNA from the Pap smear (table S3). Moreover, the ratios between the mutant allele fractions of the two mutations in the Pap smears were correlated with those of the corresponding tumor samples. For example, in the Pap smear of case PAP 083 the mutant allele fractions for the CTNNB1 and PIK3CA mutations were 0.143% and 0.064%, respectively—a ratio of 2.2 (=0.14% to 0.064%). In the primary tumor from PAP 083, the corresponding ratio was 2.0 (79.5% to 39.5%).

Similar analysis of Pap smear DNA from ovarian cancer patients revealed detectable mutations in nine of the 22 patients (41%). The fraction of mutant alleles was smaller than in endometrial cancers (median of 0.49%, range 0.021% to 5.9%; see FIG. 3 and table S3). All but one of the cases with detectable mutations were epithelial tumors; the exception was a dysgerminoma, a malignant germ cell tumor of the ovary (table S3). As with endometrial cancers, there was no statistically significant correlation between the fraction of mutant alleles and histopathologic criteria. However, most ovarian cancers are detected only at an advanced stage, and this was reflected in the patients available in our cohort.

Example 5

A Genetic Test for Screening Purposes

The results described above document that mutant DNA molecules from most endometrial cancers and some ovarian cancers can be found in routinely collected Pap smears. However, in all 46 cases depicted in FIG. 3, a specific mutation was known to occur in the tumor, and an assay was subsequently designed to determine whether that mutation was also present in the corresponding Pap smears. In a screening setting, there obviously would be no known tumor prior to the test. We therefore designed a prototype test based on Safe-SeqS that could be used in a screening setting (FIG. 2).

This multiplexed approach included 50 primer pairs that amplified segments of 241 to 296 bp containing frequently mutated regions of DNA. The regions to be amplified were chosen from the results described in Section I and included exons from APC, AKT1, BRAF, CTNNB1, EGFR, FBXW7, KRAS, PIK3CA, PPP2R1A, PTEN, and TP53. In control experiments, 46 of the 50 amplicons were shown to provide information on a minimum of 2,500 templates; the number of templates sequenced can be determined directly from SafeSeqS-based sequencing (FIG. 2). Given the accuracy of SafeSeqS, this number was adequate to comfortably detect mutations existing in >0.1% of template molecules (30). The regions covered by these 46 amplicons (table S5), encompassing 10,257 bp, were predicted to be able to detect at least one mutation in >90% of either endometrial or ovarian cancers.

Figure 4:
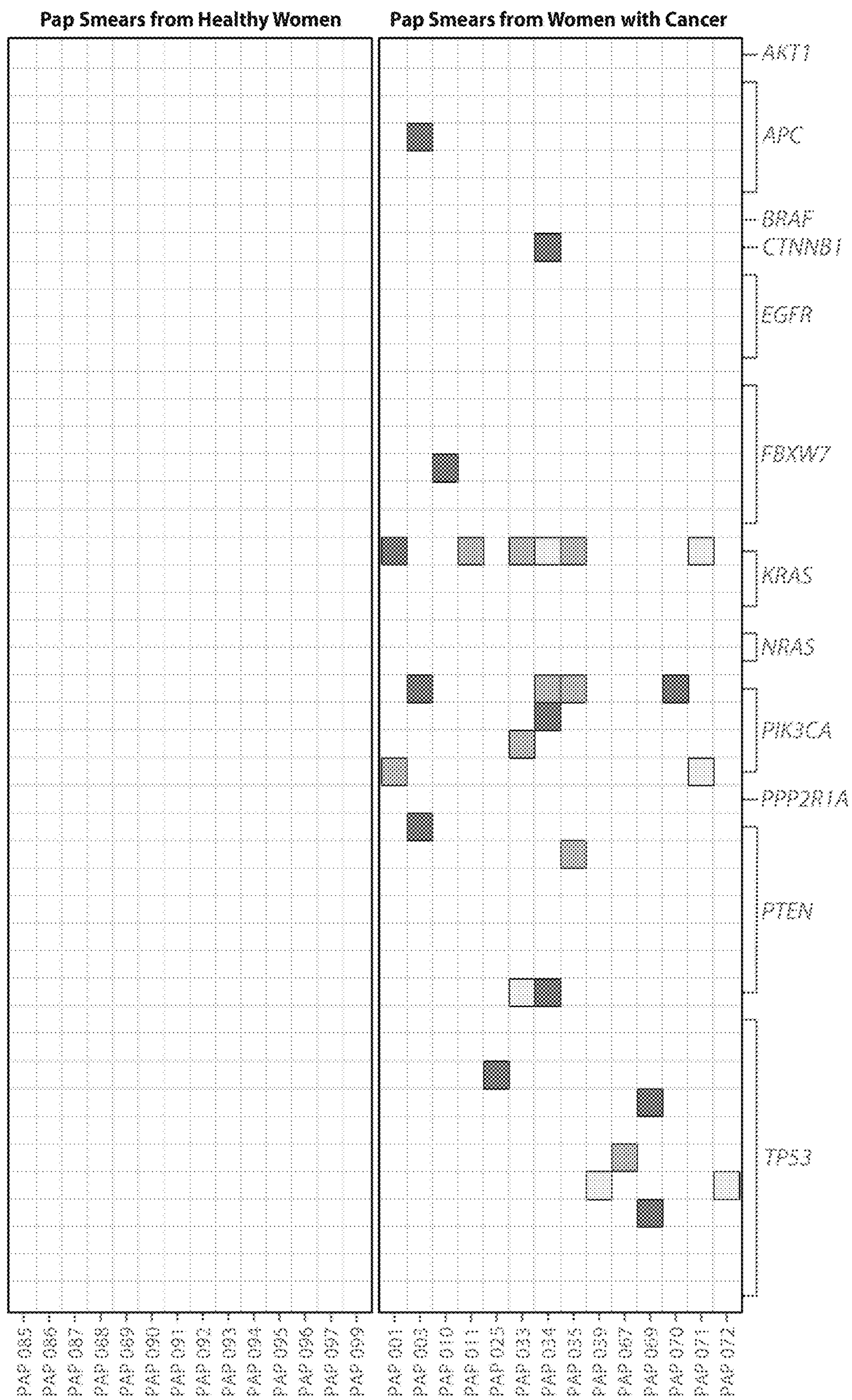
FIG. 4. Heat map depicting the results of multiplex testing of 12 genes in Pap smear fluids. Each block on the y-axis represents a 30-bp block of sequence from the indicated gene. The 28 samples assessed (14 from women with cancer, 14 from normal women without cancer) are indicated on the x-axis. Mutations are indicated as colored blocks, with white indicating no mutation, yellow indicating a mutant fraction of 0.1% to 1%, orange indicate a mutant fraction of 1% to 10%, and red indicating a mutant fraction of >10%.

This test was applied to Pap smears of 14 cases—twelve endometrial and two ovarian—as well as 14 Pap smears collected from normal women. The 14 cancer cases were arbitrarily chosen from those which had mutant allele fractions >0.1% (table S3) and therefore above the detection limit of the multiplexed assay. In all 14 Pap smears from women with cancer, the mutation expected to be present (table S3) was identified (FIG. 4 and table S6). The fraction of mutant alleles in the multiplexed test was similar to that observed in the original analysis of the same samples using only one Safe-SeqS primer pair per amplicon (table S3 and table S6). Importantly, no mutations were detected in the 14 Pap smears from women without cancer (FIG. 4; see Materials and Methods).

Example 6

Materials and Methods

Patient Samples

All samples for this study were obtained using protocols approved by the Institutional Review Boards of The Johns Hopkins Medical Institutions (Baltimore, Md.), Memorial Sloan Kettering Cancer Center (New York, N.Y.), University of Sao Paulo (Sao Paulo, Brazil), and ILSbio, LLC (Chestertown, Md.). Demographic, clinical and pathologic staging data was collected for each case. All histopathology was centrally re-reviewed by board-certified pathologists. Staging was based on 2009 FIGO criteria (38).

Fresh-frozen tissue specimens of surgically resected neoplasms of the ovary and endometrium were analyzed by frozen section to assess neoplastic cellularity by a board-certified pathologist. Serial frozen sections were used to guide the trimming of Optimal Cutting Temperature (OCT) compound embedded frozen tissue blocks to enrich the fraction of neoplastic cells for DNA extraction.

Formalin-fixed paraffin embedded (FFPE) tissue samples were assessed by a board-certified pathologist (Propath LLC, Dallas, Tex.) for tumor cellularity and to demarcate area of high tumor cellularity. Tumor tissue from serial 10 micron sections on slides from the original tumor block were macrodissected with a razorblade to enrich the fraction of neoplastic cells for DNA extraction.

The source of normal DNA was matched whole blood or non-neoplastic normal adjacent tissue.

Liquid-based Pap smears were collected using cervical brushes and transport medium from Digene HC2 DNA Collection Device (Qiagen) or ThinPrep 2000 System (Hologic) and stored using the manufacturer's recommendations.

Unless otherwise indicated, all patient-related values are reported as mean±1 standard deviation.

DNA Extraction

DNA was purified from tumor and normal tissue as well as liquid-based Pap Smears using an AllPrep kit (Qiagen) according to the manufacturer's instructions. DNA was purified from tumor tissue by adding 3 mL RLTM buffer (Qiagen) and then binding to an AllPrep DNA column (Qiagen) following the manufacturer's protocol. DNA was purified from Pap smear liquids by adding five volumes of RLTM buffer when the amount of liquid was less than 3 mL. When the amount of liquid was >3 mL, the cells and cell fragments were pelleted at 1,000×g for five minutes and the pellets were dissolved in 3 mL RLTM buffer. DNA was quantified in all cases with qPCR, employing the primers and conditions previously described (39).

Microsatellite Instability Testing

Microsatellite instability was detected using the MSI Analysis System (Promega), containing five mononucleotide repeats (BAT-25, BAT-26, NR-21, NR-24 and MONO-27) and two pentanucleotide repeat loci, per the manufacturer's instructions. Following amplification, the fluorescent PCR products were sized on an Applied Biosystems 3130 capillary electrophoresis instrument (Invitrogen). Tumor samples were designated as follows: MSI-high if two or more mononucleotides varied in length compared to the germline DNA; MSI-low if only one locus varied; and microsatellite stable (MSS) if there was no variation compared to the germline. Pentanucleotide loci confirmed identity in all cases.

Preparation of Illumina DNA Libraries and Capture for Exomic Sequencing

Preparation of Illumina genomic DNA libraries for exomic and targeted DNA captures was performed according to the manufacturer's recommendations. Briefly, 1-3 μg of genomic DNA was used for library preparation using the TruSeqDNA Sample Preparation Kit (Illumina). The DNA was acoustically sheared (Covaris) to a target size of ~200 bp. The fragments were subsequently end-repaired to convert overhangs into blunt ends. A single "A" nucleotide was then added to the 3' ends of blunt fragments to prevent them from later self-ligation; a corresponding "T" on the 3' end of adaptor molecules provided the complementary overhang. Following ligation to adaptors, the library was amplified with 8-14 cycles of PCR to ensure yields of 0.5 and 4 μg for exomic and targeted gene captures, respectively.

Exomic capture was performed with the SureSelect Human Exome Kit V 4.0 (Agilent) according to the manufacturer's protocol, with the addition of TruSeq index-specific blocks in the hybridization mixture (AGATCG-GAAGAGCACACGTCTGAACTCCAGTCAC-XXXXXX-ATCTCGTATGCCGTCTTCTGCTTGT (SEQ ID NO: 1), where the six base pair "XXXXXX" denotes one of 12 sample-specific indexes).

Targeted Gene Enrichment

Targeted gene enrichment was performed by modifications of previously described methods (40, 41). In brief, targeted regions of selected oncogenes and tumor suppressor genes were synthesized as oligonucleotide probes by Agilent Technologies. Probes of 36 bases were designed to capture both the plus and the minus strand of the DNA and had a 33-base overlap. The oligonucleotides were cleaved from the chip by incubating with 3 mL of 35% ammonium hydroxide at room temperate for five hours. The solution was transferred to two 2-ml tubes, dried under vacuum, and redissolved in 400 μL of ribonuclease (RNase)- and deoxyribonuclease (DNase)-free water. Five microliters of the solution was used for PCR amplification with primers complementary to the 12-base sequence common to all probes: 5'-TGATCCCGCGACGA*C-3' (SEQ ID NO: 2) and 5'-GACCGCGACTCCAG*C-3' (SEQ ID NO: 3), with * indicating a phosphorothioate bond. The PCR products were purified with a MinElute Purification Column (Qiagen), end-repaired with End-IT DNA End-Repair Kit (Epicentre), and then purified with a MinElute Purification Column (Qiagen). The PCR products were ligated to form concatamers as described (40).

The major difference between the protocol described in (40, 41) and the one used in the present study involved the amplification of the ligated PCR products and the solid phase capture method. The modifications were as follows: 50 ng of ligated PCR product was amplified using the REPLI-g Midi Kit (Qiagen) with the addition of 2.5 nmol Biotin-dUTP (Roche) in a 27.5 μL reaction. The reaction was incubated at 30° C. for 16 hours, the polymerase was inactivated at 65° C. for 3 mins. The amplified probes were purified with QiaQuick PCR Purification Columns (Qiagen). For capture, 4-5 μg of library DNA was incubated with 1 μg of the prepared probes in a hybridization mixture as previously described (40). The biotinylated probes and captured library sequences were subsequently purified using 500 μg Dynabeads® MyOne Streptavidin (Invitrogen). After washing as per the manufacturer's recommendations, the captured sequences were eluted with 0.1 M NaOH and then neutralized with 1M Tris-HCl (pH 7.5). Neutralized DNA was desalted and concentrated using a QIAquick MinElute Column (Qiagen) in 20 μL. The elute was amplified in a 100 μL Phusion Hot Start II (Thermo Scientific) reaction containing 1× Phusion HF buffer, 0.25 mM dNTPs, 0.5 μM each forward and reverse TruSeq primers, and 2 U polymerase with the following cycling conditions: 98° C. for 30 s; 14 cycles of 98° C. for 10 s, 60° C. for 30 s, 72° C. for 30 s; and 72° C. for 5 min. The amplified pool containing enriched target sequences was purified using an Agencourt AMPure XP system (Beckman) and quantified using a 2100 Bioanalyzer (Agilent).

Next-Generation Sequencing and Somatic Mutation Identification

After capture of targeted sequences, paired-end sequencing using an Illumina GA IIx Genome Analyzer provided 2×75 base reads from each fragment. The sequence tags that passed filtering were aligned to the human genome reference sequence (hg18) and subsequent variant-calling analysis was performed using the ELANDv2 algorithm in the CASAVA 1.6 software (Illumina). Known polymorphisms recorded in dbSNP were removed from the analysis. Identification of high confidence mutations was performed as described previously (24).

Assessment of Low-Frequency Mutations

Primer Design. We attempted to design primer pairs to detect mutations in the 46 cancers described in the text. Primers were designed as described (30), using Primer3. (42) Sixty percent of the primers amplified the expected fragments; in the other 40%, a second or third set of primers had to be designed to reduce primer dimers or non-specific amplification.

Sequencing Library Preparation. Templates were amplified as described previously (30), with modifications that will be described in full elsewhere. In brief, each strand of each template molecule was encoded with a 14 base unique identifier (UID)—comprised of degenerate N bases (equal probability of being an A, C, G, or T)—using two to four cycles of amplicon-specific PCR (UID assignment PCR cycles, see FIG. 2). While both forward and reverse gene-specific primers contained universal tag sequences at their 5' ends—providing the primer binding sites for the second-round amplification—only the forward primer contained the UID, positioned between the 5' universal tag and the 3' gene-specific sequences (four N's were included in the reverse primer to facilitate sequencing done on paired-end libraries) (table S4). The UID assignment PCR cycles included Phusion Hot Start II (Thermo Scientific) in a 50 μL reaction containing 1× Phusion HF buffer, 0.25 mM dNTPs, 0.5 μM each of forward (containing 14 N's) and reverse primers, and 2 U of polymerase. Carryover of residual UID-containing primers to the second-round amplification, which can complicate template quantification (30), was minimized through exonuclease digestion at 370 C to degrade unincorporated primers and subsequent purification with AMPure XP beads (Beckman) and elution in 10 μL TE (10 mM Tris-HCl, 1 mM EDTA, pH 8.0).

The eluted templates were amplified in a second-round PCR using primers containing the grafting sequences necessary for hybridization to the Illumina GA IIx flow cell at their 5' ends (FIG. 2) and two terminal 3' phosphorothioates to protect them from residual exonuclease activity (30). The reverse amplification primer additionally contained an index sequence between the 5 'grafting and 3' universal tag sequences to enable the PCR products from multiple individuals to be simultaneously analyzed in the same flow cell compartment of the sequencer (30). The second-round amplification reactions contained 1× Phusion HF buffer, 0.25 mM dNTPs, 0.5 μM each of forward and reverse primers, and 2 U of polymerase in a total of 50 μL. After an initial heat activation step at 980 C for 2 minutes, twenty-three cycles of PCR were performed using the following cycling conditions: 980 C for 10 s, 650 C for 15 s, and 720 C for 15 s. The multiplexed assay was performed in similar fashion utilizing six independent amplifications per sample with the primers described in table S5. The PCR products were purified using AMPure XP beads and used directly for sequencing on either the Illumina MiSeq or GA IIx instruments, with equivalent results.

Data Analysis. High quality sequence reads were analyzed as previously described. (30) Briefly, reads in which each of the 14 bases comprising the UID (representing one original template strand; see FIG. 2) had a quality score ≥15 were grouped by their UID. Only the UIDs supported by more than one read were retained for further analysis. The template-specific portion of the reads that contained the sequence of an expected amplification primer was matched to a reference sequence set using a custom script (available from the authors upon request). Artifactual mutations—introduced during the sample preparation and/or sequencing steps—were eliminated by requiring that >50% of reads sharing the same UID contained the identical mutation (a "supermutant;" see FIG. 2). For the 46 assays querying a single amplicon, we required that the fraction of mutant alleles was significantly different from the background mutation levels determined from a negative control (P<0.001, binomial test). As mutations are not known a priori in a screening environment, we used a more agnostic metric to detect mutations in the multiplexed assay. A threshold supermutant frequency was defined for each sample as equaling the mean frequency of all supermutants plus six standard deviations of the mean. Only supermutants exceeding this threshold were designated as mutations and reported in FIG. 4 and table S6.

REFERENCES

The disclosure of each reference cited is expressly incorporated herein.

1. M. Arbyn, A. Anttila, J. Jordan, G. Ronco, U. Schenck, N. Segnan, H. Wiener, A. Herbert, L. von Karsa, European Guidelines for Quality Assurance in Cervical Cancer Screening. Second edition—summary document. *Ann Oncol* 21, 448-458 (2010).
2. R. M. DeMay, *Practical principles of cytopathology*. (ASCP Press, Chicago, 2010), pp. xi, 402 p.
3. F. Bray, J. S. Ren, E. Masuyer, J. Ferlay, Global estimates of cancer prevalence for 27 sites in the adult population in 2008. *Int J Cancer*, (2012).
4. J. Ferlay, H. R. Shin, F. Bray, D. Forman, C. Mathers, D. M. Parkin, *GLOBOCAN* 2008 *v*2.0*, Cancer Incidence and Mortality Worldwide* (IARC CancerBase No. 10, Lyon, France, 2010).
5. S. B. Sams, H. S. Currens, S. S. Raab, Liquid-based Papanicolaou tests in endometrial carcinoma diagnosis. Performance, error root cause analysis, and quality improvement. *Am J Clin Pathol* 137, 248-254 (2012).
6. P. Smith, O. Bakos, G. Heimer, U. Ulmsten, Transvaginal ultrasound for identifying endometrial abnormality. *Acta Obstet Gynecol Scand* 70, 591-594 (1991).
7. H. Mitchell, G. Giles, G. Medley, Accuracy and survival benefit of cytological prediction of endometrial carcinoma on routine cervical smears. *Int J Gynecol Pathol* 12, 34-40 (1993).
8. K. J. Carlson, S. J. Skates, D. E. Singer, Screening for ovarian cancer. *Ann Intern Med* 121, 124-132 (1994).
9. H. Meden, A. Fattahi-Meibodi, CA 125 in benign gynecological conditions. *Int J Biol Markers* 13, 231-237 (1998).
10. S. S. Buys, E. Partridge, A. Black, C. C. Johnson, L. Lamerato, C. Isaacs, D. J. Reding, R. T. Greenlee, L. A. Yokochi, B. Kessel, E. D. Crawford, T. R. Church, G. L. Andriole, J. L. Weissfeld, M. N. Fouad, D. Chia, B. O'Brien, L. R. Ragard, J. D. Clapp, J. M. Rathmell, T. L. Riley, P. Hartge, P. F. Pinsky, C. S. Zhu, G. Izmirlian, B. S. Kramer, A. B. Miller, J. L. Xu, P. C. Prorok, J. K. Gohagan, C. D. Berg, Effect of screening on ovarian cancer mortality: the Prostate, Lung, Colorectal and Ovarian (PLCO) Cancer Screening Randomized Controlled Trial. *JAMA* 305, 2295-2303 (2011).
11. ACOG Practice Bulletin. Clinical Management Guidelines for Obstetrician-Gynecologists. Number 60, March 2005. Pregestational diabetes mellitus. *Obstet Gynecol* 105, 675-685 (2005).
12. E. Partridge, A. R. Kreimer, R. T. Greenlee, C. Williams, J. L. Xu, T. R. Church, B. Kessel, C. C. Johnson, J. L. Weissfeld, C. Isaacs, G. L. Andriole, S. Ogden, L. R. Ragard, S. S. Buys, Results from four rounds of ovarian cancer screening in a randomized trial. *Obstet Gynecol* 113, 775-782 (2009).
13. American Cancer Society. Detailed guide: ovarian cancer—can ovarian cancer be found early? (Available at http://www.cancer.org/Cancer/OvarianCancer/DetailedGuide/ovarian-cancer-detection).
14. Screening for ovarian cancer: recommendation statement. U.S. Preventive Services Task Force. *Am Fam Physician* 71, 759-762 (2005).
15. ACOG Committee Opinion: number 280, December 2002. The role of the generalist obstetrician-gynecologist in the early detection of ovarian cancer. *Obstet Gynecol* 100, 1413-1416 (2002).
16. National Comprehensive Cancer Network Practice Guidelines in Oncology: ovarian cancer and genetic screening. (Available at http://www.nccn.org/professionals/physician_gls/PDF/genetics_screening.pdf).
17. N. M. Lindor, G. M. Petersen, D. W. Hadley, A. Y. Kinney, S. Miesfeldt, K. H. Lu, P. Lynch, W. Burke, N. Press, Recommendations for the care of individuals with an inherited predisposition to Lynch syndrome: a systematic review. *JAMA* 296, 1507-1517 (2006).
18. J. P. Marques, L. B. Costa, A. P. Pinto, A. F. Lima, M. E. Duarte, A. P. Barbosa, P. L. Medeiros, Atypical glandular cells and cervical cancer: systematic review. *Rev Assoc Med Bras* 57, 234-238 (2011).
19. R. P. Insinga, A. G. Glass, B. B. Rush, Diagnoses and outcomes in cervical cancer screening: a population-based study. *Am J Obstet Gynecol* 191, 105-113 (2004).
20. K. E. Sharpless, P. F. Schnatz, S. Mandavilli, J. F. Greene, J. I. Sorosky, Dysplasia associated with atypical glandular cells on cervical cytology. *Obstet Gynecol* 105, 494-500 (2005).
21. C. P. DeSimone, M. E. Day, M. M. Tovar, C. S. Dietrich, 3rd, M. L. Eastham, S. C. Modesitt, Rate of pathology from atypical glandular cell Pap tests classified by the Bethesda 2001 nomenclature. *Obstet Gynecol* 107, 1285-1291 (2006).
22. C. S. Geier, M. Wilson, W. Creasman, Clinical evaluation of atypical glandular cells of undetermined significance. *Am J Obstet Gynecol* 184, 64-69 (2001).
23. Integrated genomic analyses of ovarian carcinoma. *Nature* 474, 609-615 (2011).
24. S. Jones, T. L. Wang, M. Shih Ie, T. L. Mao, K. Nakayama, R. Roden, R. Glas, D. Slamon, L. A. Diaz, Jr., B. Vogelstein, K. W. Kinzler, V. E. Velculescu, N. Papadopoulos, Frequent mutations of chromatin remodeling gene ARID1A in ovarian clear cell carcinoma. *Science* 330, 228-231 (2010).
25. S. Jones, T. L. Wang, R. J. Kurman, K. Nakayama, V. E. Velculescu, B. Vogelstein, K. W. Kinzler, N. Papadopoulos, M. Shih Ie, Low-grade serous carcinomas of the ovary contain very few point mutations. *J Pathol* 226, 413-420 (2012).
26. S. A. Forbes, N. Bindal, S. Bamford, C. Cole, C. Y. Kok, D. Beare, M. Jia, R. Shepherd, K. Leung, A. Menzies, J. W. Teague, P. J. Campbell, M. R. Stratton, P. A. Futreal, COSMIC: mining complete cancer genomes in the Catalogue of Somatic Mutations in Cancer. *Nucleic Acids Res* 39, D945-950 (2011).
27. E. Barrow, L. Robinson, W. Alduaij, A. Shenton, T. Clancy, F. Lalloo, J. Hill, D. G. Evans, Cumulative lifetime incidence of extracolonic cancers in Lynch syndrome: a report of 121 families with proven mutations. *Clin Genet* 75, 141-149 (2009).

28. K. Oda, D. Stokoe, Y. Taketani, F. McCormick, High frequency of coexistent mutations of PIK3CA and PTEN genes in endometrial carcinoma. *Cancer Res* 65, 10669-10673 (2005).

29. E. Kuhn, R. C. Wu, B. Guan, G. Wu, J. Zhang, Y. Wang, L. Song, X. Yuan, L. Wei, R. B. Roden, K. T. Kuo, K. Nakayama, B. Clarke, P. Shaw, N. Olvera, R. J. Kurman, D. A. Levine, T. L. Wang, I. M. Shih, Identification of Molecular Pathway Aberrations in Uterine Serous Carcinoma by Genome-wide Analyses. *J Natl Cancer Inst*, (2012).

30. I. Kinde, J. Wu, N. Papadopoulos, K. W. Kinzler, B. Vogelstein, Detection and quantification of rare mutations with massively parallel sequencing. *Proc Natl Acad Sci USA* 108, 9530-9535 (2011).

31. H. F. Traut, G. N. Papanicolaou, Cancer of the Uterus: The Vaginal Smear in Its Diagnosis. *Cal West Med* 59, 121-122 (1943).

32. B. Vogelstein, K. W. Kinzler, Cancer genes and the pathways they control. *Nat Med* 10, 789-799 (2004).

33. J. M. Cooper, M. L. Erickson, Endometrial sampling techniques in the diagnosis of abnormal uterine bleeding. *Obstet Gynecol Clin North Am* 27, 235-244 (2000).

34. C. C. Gunderson, A. N. Fader, K. A. Carson, R. E. Bristow, Oncologic and reproductive outcomes with progestin therapy in women with endometrial hyperplasia and grade 1 adenocarcinoma: a systematic review. *Gynecol Oncol* 125, 477-482 (2012).

35. R. E. Bristow, R. S. Tomacruz, D. K. Armstrong, E. L. Trimble, F. J. Montz, Survival effect of maximal cytoreductive surgery for advanced ovarian carcinoma during the platinum era: a meta-analysis. *J Clin Oncol* 20, 1248-1259 (2002).

36. M. H. Mayrand, E. Duarte-Franco, I. Rodrigues, S. D. Walter, J. Hanley, A. Ferenczy, S. Ratnam, F. Coutlee, E. L. Franco, Human papillomavirus DNA versus Papanicolaou screening tests for cervical cancer. *N Engl J Med* 357, 1579-1588 (2007).

37. P. Naucler, W. Ryd, S. Tornberg, A. Strand, G. Wadell, K. Elfgren, T. Radberg, B. Strander, B. Johansson, O. Forslund, B. G. Hansson, E. Rylander, J. Dillner, Human papillomavirus and Papanicolaou tests to screen for cervical cancer. *N Engl J Med* 357, 1589-1597 (2007).

38. S. Pecorelli, Revised FIGO staging for carcinoma of the vulva, cervix, and endometrium. *Int J Gynaecol* Obstet 105, 103-104 (2009).

39. C. Rago, D. L. Huso, F. Diehl, B. Karim, G. Liu, N. Papadopoulos, Y. Samuels, V. E. Velculescu, B. Vogelstein, K. W. Kinzler, L. A. Diaz, Jr., Serial assessment of human tumor burdens in mice by the analysis of circulating DNA. *Cancer Res* 67, 9364-9370 (2007).

40. J. Wu, H. Matthaei, A. Maitra, M. Dal Molin, L. D. Wood, J. R. Eshleman, M. Goggins, M. I. Canto, R. D. Schulick, B. H. Edil, C. L. Wolfgang, A. P. Klein, L. A. Diaz, Jr., P. J. Allen, C. M. Schmidt, K. W. Kinzler, N. Papadopoulos, R. H. Hruban, B. Vogelstein, Recurrent GNAS mutations define an unexpected pathway for pancreatic cyst development. *Sci Transl Med* 3, 92ra66 (2011).

41. J. He, J. Wu, Y. Jiao, N. Wagner-Johnston, R. F. Ambinder, L. A. Diaz, Jr., K. W. Kinzler, B. Vogelstein, N. Papadopoulos, IgH gene rearrangements as plasma biomarkers in Non-Hodgkin's lymphoma patients. *Oncotarget* 2, 178-185 (2011).

42. S. Rozen, H. Skaletsky, Primer3 on the WWW for general users and for biologist programmers. Methods *Mol Biol* 132, 365-386 (2000).

43. N. Howlader, A. M. Noone, M. Krapcho, N. Neyman, R. Aminou, S. F. Altekruse, C. L. Kosary, J. Ruhl, Z. Tatalovich, H. Cho, A. Mariotto, M. P. Eisner, D. R. Lewis, H. S. Chen, E. J. Feuer, K. A. Cronin, *SEER Cancer Statistics Review,* 1975-2009 (National Cancer Institute. Bethesda, Md., 2012).

44. A. Malpica, M. T. Deavers, K. Lu, D. C. Bodurka, E. N. Atkinson, D. M. Gershenson, E. G. Silva, Grading ovarian serous carcinoma using a two-tier system. *Am J Surg Pathol* 28, 496-504 (2004).

45, L. A. G. Ries, J. L. Young, G. E. Keel, M. P. Eisner, Y. D. Lin, M-J. Homer, *SEER Survival Monograph: Cancer Survival Among Adults: US SEER Program,* 1988-2001, *Patient and Tumor Characteristics* (NIH Pub. No. 07-6215. National Cancer Institute, Bethesda, Md., 2007).

46. C. A. Hamilton, M. K. Cheung, K. Osann, L. Chen, N. N. Teng, T. A. Longacre, M. A. Powell, M. R. Hendrickson, D. S. Kapp, J. K. Chan, Uterine papillary serous and clear cell carcinomas predict for poorer survival compared to grade 3 endometrioid corpus cancers. *Br J Cancer* 94, 642-646 (2006).

The invention claimed is:

1. A method comprising:

testing a liquid Pap specimen obtained from a human subject for one or more mutations in each of at least seven genes mutated in endometrial cancer, wherein said at least seven genes comprise: CTNNB1, PIK3CA, PTEN, TP53, KRAS, APC, and FBXW7, wherein said one or more mutations in said at least seven genes are single nucleotide polymorphisms chosen from missense mutations, nonsense mutations, and indels;

wherein said one or more mutations in said FBXW7 gene comprises 1435C>T, and detecting the presence of the T allele at position 1435 of FBXW7 gene; and wherein the step of testing is performed on amplicon template molecules from each of said at least seven genes and by increasing the sensitivity of massively parallel sequencing with an error reduction technique that comprises:

a) assignment of a unique identifier (UID) to each of said amplicon template molecules to generate uniquely tagged template molecules;

b) amplification of each uniquely tagged template molecule to create UID-families of amplification products; and c) redundant sequencing of the amplification products.

2. The method of claim 1, wherein the step of testing is performed in a multiplex assay.

3. The method of claim 1, wherein the step of testing is repeated over time.

4. The method of claim 1, wherein the liquid Pap specimen is collected after surgical debulking of an ovarian tumor.

5. The method of claim 1, wherein the liquid Pap specimen is collected from the cervix.

6. The method of claim 1, wherein the liquid Pap specimen comprises cells from the ectocervix.

7. The method of claim 1, wherein said one or more mutations in said APC gene comprises 4348C>T.

8. The method of claim 7, wherein the presence of said 4348C>T mutation in said APC gene is detected.

9. The method of claim 7, wherein said one or more mutations in said CTNNB1 gene comprises 100G>A.

10. The method of claim 9, wherein the presence of said 100G>A mutation in said CTNNB1 gene is detected.

11. The method of claim 10, wherein the presence of said 1435C>T mutation in said FBXW7 gene, and the presence of said 4348C>T mutation in said APC gene, are detected.

12. The method of claim 1, wherein said human subject has an endometrial tumor.

13. The method of claim 11, wherein said human subject has an endometrial tumor.

14. The method of claim 1, wherein said human subject has endometrial cancer.

15. The method of claim 11, wherein said human subject has endometrial cancer.

* * * * *

UNITED STATES PATENT AND TRADEMARK OFFICE

CERTIFICATE OF CORRECTION

PATENT NO. : 11,525,163 B2
APPLICATION NO. : 14/439041
DATED : December 13, 2022
INVENTOR(S) : Isaac Kinde et al.

It is certified that error appears in the above-identified patent and that said Letters Patent is hereby corrected as shown below:

In the Specification

In Column 1, Lines 4-12, please delete "This invention was made with government support under grant no. CA043460, CA062924, CN043309, and CA129825 awarded by the National Institutes of Health. The government has certain rights in the invention. This invention was made using funds from the National Cancer Institute and the National Institutes of Health. The U.S. government retains certain rights under the terms of NCI contract N01-CN-43309 and NIH grants CA129825 and CA43460.", and insert -- This invention was made with Government support under grant nos. CA043460, CA062924, and CA129825, and under contract no. HHSN261200433009C, all awarded by the National Institutes of Health. The government has certain rights in the invention. --

Signed and Sealed this
Thirtieth Day of May, 2023

Katherine Kelly Vidal

Katherine Kelly Vidal
*Director of the United States Patent and Trademark Office*

SEQUENCE LISTING

```
<160> NUMBER OF SEQ ID NOS: 191

<210> SEQ ID NO 1
<211> LENGTH: 65
<212> TYPE: DNA
<213> ORGANISM: Artificial Sequence
<220> FEATURE:
<223> OTHER INFORMATION: capture sequence
<221> NAME/KEY: misc_feature
<222> LOCATION: (1)...(65)
<223> OTHER INFORMATION: n = A,T,C or G

<400> SEQUENCE: 1

agatcggaag agcacacgtc tgaactccag tcacnnnnnn atctcgtatg ccgtcttctg     60

cttgt                                                                 65


<210> SEQ ID NO 2
<211> LENGTH: 15
```

```
<212> TYPE: DNA
<213> ORGANISM: Artificial Sequence
<220> FEATURE:
<223> OTHER INFORMATION: Primers

<400> SEQUENCE: 2

tgatcccgcg acgac                                                    15


<210> SEQ ID NO 3
<211> LENGTH: 15
<212> TYPE: DNA
<213> ORGANISM: Artificial Sequence
<220> FEATURE:
<223> OTHER INFORMATION: Primers

<400> SEQUENCE: 3

gaccgcgact ccagc                                                    15


<210> SEQ ID NO 4
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 4

cgacgtaaaa cgacggccag tnnnnnnnnn nnnnngatcc aatccatttt tgttgtccag     60


<210> SEQ ID NO 5
<211> LENGTH: 45
<212> TYPE: DNA
<213> ORGANISM: Artificial Sequence
<220> FEATURE:
<223> OTHER INFORMATION: Primers

<400> SEQUENCE: 5

cacacaggaa acagctatga ccatgtgagc aagaggcttt ggagt                   45


<210> SEQ ID NO 6
<211> LENGTH: 52
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(52)
<223> OTHER INFORMATION: n = A,T,C or G

<400> SEQUENCE: 6

cgacgtaaaa cgacggccag tnnnnnnnnn nnnnnggcca agacctgccc tg             52


<210> SEQ ID NO 7
<211> LENGTH: 47
<212> TYPE: DNA
<213> ORGANISM: Artificial Sequence
<220> FEATURE:
<223> OTHER INFORMATION: Primers

<400> SEQUENCE: 7

cacacaggaa acagctatga ccatgtgctg tgactgcttg tagatgg                 47


<210> SEQ ID NO 8
<211> LENGTH: 56
<212> TYPE: DNA
```

<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 8
cgacgtaaaa cgacggccag tnnnnnnnnn nnnnnccacc tcctcaaaca gctcaa 56

<210> SEQ ID NO 9
<211> LENGTH: 46
<212> TYPE: DNA
<213> ORGANISM: Artificial Sequence
<220> FEATURE:
<223> OTHER INFORMATION: Primers

<400> SEQUENCE: 9
cacacaggaa acagctatga ccatgtgcag cttgcttagg tccact 46

<210> SEQ ID NO 10
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 10
cgacgtaaaa cgacggccag tnnnnnnnnn nnnnntggcc atctacaagc agtca 55

<210> SEQ ID NO 11
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 11
cacacaggaa acagctatga ccatgnnnnt caccatcgct atctgagca 49

<210> SEQ ID NO 12
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 12
cgacgtaaaa cgacggccag tnnnnnnnnn nnnnncattg gtgatgattc gatgg 55

<210> SEQ ID NO 13
<211> LENGTH: 45
<212> TYPE: DNA
<213> ORGANISM: Artificial Sequence
<220> FEATURE:
<223> OTHER INFORMATION: Primers

<400> SEQUENCE: 13
cacacaggaa acagctatga ccatgctgcc tggctcagaa ttcac 45

<210> SEQ ID NO 14
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 14
cgacgtaaaa cgacggccag tnnnnnnnnn nnnnnccctt tcttgcggag attc 54

<210> SEQ ID NO 15
<211> LENGTH: 45
<212> TYPE: DNA
<213> ORGANISM: Artificial Sequence
<220> FEATURE:
<223> OTHER INFORMATION: Primers

<400> SEQUENCE: 15
cacacaggaa acagctatga ccatgctact gggacggaac agctt 45

<210> SEQ ID NO 16
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 16
cgacgtaaaa cgacggccag tnnnnnnnnn nnnnnggaag agaatctccg caaga 55

<210> SEQ ID NO 17
<211> LENGTH: 45
<212> TYPE: DNA
<213> ORGANISM: Artificial Sequence
<220> FEATURE:
<223> OTHER INFORMATION: Primers

<400> SEQUENCE: 17
cacacaggaa acagctatga ccatggcttc ttgtcctgct tgctt 45

<210> SEQ ID NO 18
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 18
cgacgtaaaa cgacggccag tnnnnnnnnn nnnnnggcct gtctcaatat cccaaa 56

<210> SEQ ID NO 19
<211> LENGTH: 48
<212> TYPE: DNA
<213> ORGANISM: Artificial Sequence
<220> FEATURE:
<223> OTHER INFORMATION: Primers

<400> SEQUENCE: 19
cacacaggaa acagctatga ccatgttgtt tttctgtttc tccctctg 48

<210> SEQ ID NO 20
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 20
cgacgtaaaa cgacggccag tnnnnnnnnn nnnnncaagg cactcttgcc tacg 54

<210> SEQ ID NO 21
<211> LENGTH: 54
<212> TYPE: DNA
<213> ORGANISM: Artificial Sequence
<220> FEATURE:
<223> OTHER INFORMATION: Primers

<400> SEQUENCE: 21
cacacaggaa acagctatga ccatgcattt tcattatttt tattataagg cctg 54

<210> SEQ ID NO 22
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 22
cgacgtaaaa cgacggccag tnnnnnnnnn nnnnnctgtg gtagtggcac cagaa 55

<210> SEQ ID NO 23
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 23
cacacaggaa acagctatga ccatgnnnna agcggctgtt agtcactgg 49

<210> SEQ ID NO 24
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 24
cgacgtaaaa cgacggccag tnnnnnnnnn nnnnnggccc ctgtcatctt ctgt 54

<210> SEQ ID NO 25
<211> LENGTH: 45
<212> TYPE: DNA

```
<213> ORGANISM: Artificial Sequence
<220> FEATURE:
<223> OTHER INFORMATION: Primers

<400> SEQUENCE: 25

cacacaggaa acagctatga ccatggactt ggctgtccca gaatg                    45


<210> SEQ ID NO 26
<211> LENGTH: 58
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(58)
<223> OTHER INFORMATION: n = A,T,C or G

<400> SEQUENCE: 26

cgacgtaaaa cgacggccag tnnnnnnnnn nnnnncaaga aatcgatagc atttgcag      58


<210> SEQ ID NO 27
<211> LENGTH: 52
<212> TYPE: DNA
<213> ORGANISM: Artificial Sequence
<220> FEATURE:
<223> OTHER INFORMATION: Primers

<400> SEQUENCE: 27

cacacaggaa acagctatga ccatgtttat ttgctttgtc aagatcattt tt            52


<210> SEQ ID NO 28
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 28

cgacgtaaaa cgacggccag tnnnnnnnnn nnnnnaggaa atatctgctt gctcattcaa    60


<210> SEQ ID NO 29
<211> LENGTH: 54
<212> TYPE: DNA
<213> ORGANISM: Artificial Sequence
<220> FEATURE:
<223> OTHER INFORMATION: Primers

<400> SEQUENCE: 29

cacacaggaa acagctatga ccatggaagc agatactaag caggacacta tatc          54


<210> SEQ ID NO 30
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 30

cgacgtaaaa cgacggccag tnnnnnnnnn nnnnnttccc ttggattctg acaca         55


<210> SEQ ID NO 31
```

<211> LENGTH: 45
<212> TYPE: DNA
<213> ORGANISM: Artificial Sequence
<220> FEATURE:
<223> OTHER INFORMATION: Primers

<400> SEQUENCE: 31
cacacaggaa acagctatga ccatgagcac cattcgttga taggc 45

<210> SEQ ID NO 32
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 32
cgacgtaaaa cgacggccag tnnnnnnnnn nnnnncactg gcagcaacag tcttacc 57

<210> SEQ ID NO 33
<211> LENGTH: 49
<212> TYPE: DNA
<213> ORGANISM: Artificial Sequence
<220> FEATURE:
<223> OTHER INFORMATION: Primers

<400> SEQUENCE: 33
cacacaggaa acagctatga ccatggattg cctttaccac tcagagaag 49

<210> SEQ ID NO 34
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 34
cgacgtaaaa cgacggccag tnnnnnnnnn nnnnnttgca gcaattcact gtaaagc 57

<210> SEQ ID NO 35
<211> LENGTH: 55
<212> TYPE: DNA
<213> ORGANISM: Artificial Sequence
<220> FEATURE:
<223> OTHER INFORMATION: Primers

<400> SEQUENCE: 35
cacacaggaa acagctatga ccatgccgat gtaataaata tgcacatatc attac 55

<210> SEQ ID NO 36
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 36
cgacgtaaaa cgacggccag tnnnnnnnnn nnnnncaagg cactcttgcc tacg 54

```
<210> SEQ ID NO 37
<211> LENGTH: 54
<212> TYPE: DNA
<213> ORGANISM: Artificial Sequence
<220> FEATURE:
<223> OTHER INFORMATION: Primers

<400> SEQUENCE: 37

cacacaggaa acagctatga ccatgcattt tcattatttt tattataagg cctg          54


<210> SEQ ID NO 38
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 38

cgacgtaaaa cgacggccag tnnnnnnnnn nnnnncactg gcagcaacag tcttacc       57


<210> SEQ ID NO 39
<211> LENGTH: 49
<212> TYPE: DNA
<213> ORGANISM: Artificial Sequence
<220> FEATURE:
<223> OTHER INFORMATION: Primers

<400> SEQUENCE: 39

cacacaggaa acagctatga ccatggattg cctttaccac tcagagaag                49


<210> SEQ ID NO 40
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 40

cgacgtaaaa cgacggccag tnnnnnnnnn nnnnncaagg cactcttgcc tacg          54


<210> SEQ ID NO 41
<211> LENGTH: 54
<212> TYPE: DNA
<213> ORGANISM: Artificial Sequence
<220> FEATURE:
<223> OTHER INFORMATION: Primers

<400> SEQUENCE: 41

cacacaggaa acagctatga ccatgcattt tcattatttt tattataagg cctg          54


<210> SEQ ID NO 42
<211> LENGTH: 58
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(58)
<223> OTHER INFORMATION: n = A,T,C or G

<400> SEQUENCE: 42
```

cgacgtaaaa cgacggccag tnnnnnnnnn nnnnnagctc aaagcaattt ctacacga 58

<210> SEQ ID NO 43
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 43
cacacaggaa acagctatga ccatgnnnng cacttacctg tgactccata gaa 53

<210> SEQ ID NO 44
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 44
cgacgtaaaa cgacggccag tnnnnnnnnn nnnnntcttt tgatgacatt gcatacattc 60

<210> SEQ ID NO 45
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 45
cacacaggaa acagctatga ccatgnnnna ctccaaagcc tcttgctca 49

<210> SEQ ID NO 46
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 46
cgacgtaaaa cgacggccag tnnnnnnnnn nnnnncagtt gcaaaccaga cctca 55

<210> SEQ ID NO 47
<211> LENGTH: 49
<212> TYPE: DNA
<213> ORGANISM: Artificial Sequence
<220> FEATURE:
<223> OTHER INFORMATION: Primers

<400> SEQUENCE: 47
cacacaggaa acagctatga ccatgtgtgg agtatttgga tgacagaaa 49

<210> SEQ ID NO 48
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 48
cgacgtaaaa cgacggccag tnnnnnnnnn nnnnngtggc aagtggctcc tga 53

<210> SEQ ID NO 49
<211> LENGTH: 45
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(45)
<223> OTHER INFORMATION: n = A,T,C or G

<400> SEQUENCE: 49
cacacaggaa acagctatga ccatgnnnnc atgggcggca tgaac 45

<210> SEQ ID NO 50
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 50
cgacgtaaaa cgacggccag tnnnnnnnnn nnnnnactgg cagcaacagt cttacct 57

<210> SEQ ID NO 51
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 51
cacacaggaa acagctatga ccatgnnnnc ctcaggattg cctttacca 49

<210> SEQ ID NO 52
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 52
cgacgtaaaa cgacggccag tnnnnnnnnn nnnnnagtcc ggcttggagg atg 53

<210> SEQ ID NO 53
<211> LENGTH: 45
<212> TYPE: DNA
<213> ORGANISM: Artificial Sequence
<220> FEATURE:
<223> OTHER INFORMATION: Primers

<400> SEQUENCE: 53
cacacaggaa acagctatga ccatgtcccc actcctcctt tcttc 45

<210> SEQ ID NO 54
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 54
cgacgtaaaa cgacggccag tnnnnnnnnn nnnnnggaaa gggacgaact ggtg 54

<210> SEQ ID NO 55
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 55
cacacaggaa acagctatga ccatgnnnnt agggcctctt gtgccttta 49

<210> SEQ ID NO 56
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 56
cgacgtaaaa cgacggccag tnnnnnnnnn nnnnntcttc tgtcccttcc cagaa 55

<210> SEQ ID NO 57
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 57
cacacaggaa acagctatga ccatgnnnng acttggctgt cccagaatg 49

<210> SEQ ID NO 58
<211> LENGTH: 58
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(58)
<223> OTHER INFORMATION: n = A,T,C or G

<400> SEQUENCE: 58
cgacgtaaaa cgacggccag tnnnnnnnnn nnnnntcata ccaatttctc gattgagg 58

<210> SEQ ID NO 59
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 59
cacacaggaa acagctatga ccatgnnnnc ggctttttca accctttt 49

<210> SEQ ID NO 60
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 60
cgacgtaaaa cgacggccag tnnnnnnnnn nnnnntggcc atctacaagc agtca 55

<210> SEQ ID NO 61
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 61
cacacaggaa acagctatga ccatgnnnnt caccatcgct atctgagca 49

<210> SEQ ID NO 62
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 62
cgacgtaaaa cgacggccag tnnnnnnnnn nnnnngggac ggaacagctt tgag 54

<210> SEQ ID NO 63
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 63
cacacaggaa acagctatga ccatgnnnng cggagattct cttcctctgt 50

<210> SEQ ID NO 64
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 64
cgacgtaaaa cgacggccag tnnnnnnnnn nnnnncggtg taggagctgc tggt 54

<210> SEQ ID NO 65
<211> LENGTH: 48
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(48)
<223> OTHER INFORMATION: n = A,T,C or G

<400> SEQUENCE: 65
cacacaggaa acagctatga ccatgnnnna cccaggtcca gatgaagc 48

<210> SEQ ID NO 66
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 66
cgacgtaaaa cgacggccag tnnnnnnnnn nnnnntggcc atctacaagc agtca 55

<210> SEQ ID NO 67
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 67
cacacaggaa acagctatga ccatgnnnnt caccatcgct atctgagca 49

<210> SEQ ID NO 68
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 68
cgacgtaaaa cgacggccag tnnnnnnnnn nnnnngtggc aagtggctcc tga 53

<210> SEQ ID NO 69
<211> LENGTH: 45
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(45)

<223> OTHER INFORMATION: n = A,T,C or G

<400> SEQUENCE: 69
cacacaggaa acagctatga ccatgnnnnc atgggcggca tgaac 45

<210> SEQ ID NO 70
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 70
cgacgtaaaa cgacggccag tnnnnnnnnn nnnnncgaaa agtgtttctg tcatcca 57

<210> SEQ ID NO 71
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 71
cacacaggaa acagctatga ccatgnnnng cccctcctca gcatcttat 49

<210> SEQ ID NO 72
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 72
cgacgtaaaa cgacggccag tnnnnnnnnn nnnnncagtt gcaaaccaga cctca 55

<210> SEQ ID NO 73
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 73
cacacaggaa acagctatga ccatgnnnnt gtggagtatt tggatgacag aaa 53

<210> SEQ ID NO 74
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 74
cgacgtaaaa cgacggccag tnnnnnnnnn nnnnnttata tttccccatg ccaatg 56

<210> SEQ ID NO 75
<211> LENGTH: 59
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(59)
<223> OTHER INFORMATION: n = A,T,C or G

<400> SEQUENCE: 75
cacacaggaa acagctatga ccatgnnnng gtgttttgaa atgtgtttta taatttaga 59

<210> SEQ ID NO 76
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 76
cgacgtaaaa cgacggccag tnnnnnnnnn nnnnntcttc tgtcccttcc cagaa 55

<210> SEQ ID NO 77
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 77
cacacaggaa acagctatga ccatgnnnng acttggctgt cccagaatg 49

<210> SEQ ID NO 78
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 78
cgacgtaaaa cgacggccag tnnnnnnnnn nnnnngaaaa agccgaaggt cacaa 55

<210> SEQ ID NO 79
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 79
cacacaggaa acagctatga ccatgnnnnc tcaagaagca gaaagggaag a 51

<210> SEQ ID NO 80

<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 80
cgacgtaaaa cgacggccag tnnnnnnnnn nnnnngatcc aatccatttt tgttgtccag 60

<210> SEQ ID NO 81
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 81
cacacaggaa acagctatga ccatgnnnnt gagcaagagg ctttggagt 49

<210> SEQ ID NO 82
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 82
cgacgtaaaa cgacggccag tnnnnnnnnn nnnnntgtga tgatggtgag gatgg 55

<210> SEQ ID NO 83
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 83
cacacaggaa acagctatga ccatgnnnnt ccactacaac tacatgtgta acagttc 57

<210> SEQ ID NO 84
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 84
cgacgtaaaa cgacggccag tnnnnnnnnn nnnnnctccg tcatgtgctg tgact 55

<210> SEQ ID NO 85
<211> LENGTH: 48
<212> TYPE: DNA
<213> ORGANISM: Artificial Sequence
<220> FEATURE:

<223> OTHER INFORMATION: Primers
<221> NAME/KEY: misc_feature
<222> LOCATION: (1)...(48)
<223> OTHER INFORMATION: n = A,T,C or G

<400> SEQUENCE: 85
cacacaggaa acagctatga ccatgnnnnc agctgtgggt tgattcca 48

<210> SEQ ID NO 86
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 86
cgacgtaaaa cgacggccag tnnnnnnnnn nnnnntggcc atctacaagc agtca 55

<210> SEQ ID NO 87
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 87
cacacaggaa acagctatga ccatgnnnnt caccatcgct atctgagca 49

<210> SEQ ID NO 88
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 88
cgacgtaaaa cgacggccag tnnnnnnnnn nnnnnccaat ccatttttgt tgtcca 56

<210> SEQ ID NO 89
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 89
cacacaggaa acagctatga ccatgnnnnt gagcaagagg ctttggagt 49

<210> SEQ ID NO 90
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 90
cgacgtaaaa cgacggccag tnnnnnnnnn nnnnnctgca cagggcaggt ctt 53

<210> SEQ ID NO 91
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 91
cacacaggaa acagctatga ccatgnnnnc tctgtctcct tcctcttcct aca 53

<210> SEQ ID NO 92
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 92
cgacgtaaaa cgacggccag tnnnnnnnnn nnnnntggcc atctacaagc agtca 55

<210> SEQ ID NO 93
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 93
cacacaggaa acagctatga ccatgnnnnt caccatcgct atctgagca 49

<210> SEQ ID NO 94
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 94
cgacgtaaaa cgacggccag tnnnnnnnnn nnnnncacgc aaatttcctt ccact 55

<210> SEQ ID NO 95
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 95
cacacaggaa acagctatga ccatgnnnng gcctctgatt cctcactgat 50

<210> SEQ ID NO 96
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 96
cgacgtaaaa cgacggccag tnnnnnnnnn nnnnngatcc aatccatttt tgttgtccag 60

<210> SEQ ID NO 97
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 97
cacacaggaa acagctatga ccatgnnnnt gagcaagagg ctttggagt 49

<210> SEQ ID NO 98
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 98
cgacgtaaaa cgacggccag tnnnnnnnnn nnnnnactgg cagcaacagt cttacct 57

<210> SEQ ID NO 99
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 99
cacacaggaa acagctatga ccatgnnnnc ctcaggattg cctttacca 49

<210> SEQ ID NO 100
<211> LENGTH: 62
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(62)
<223> OTHER INFORMATION: n = A,T,C or G

<400> SEQUENCE: 100
gacgtaaaac gacggccagt nnnnnnnnnn nnnnaaagta acatttccaa tctactaatg 60
ct 62

<210> SEQ ID NO 101
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 101
cacacaggaa acagctatga ccatgnnnnt gagaaaatcc ctgttcccac 50

<210> SEQ ID NO 102
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 102
cgacgtaaaa cgacggccag tnnnnnnnnn nnnnntggag cctcttacac ccagt 55

<210> SEQ ID NO 103
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 103
cacacaggaa acagctatga ccatgnnnna aaaacactgg agtttcccaa a 51

<210> SEQ ID NO 104
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 104
cgacgtaaaa cgacggccag tnnnnnnnnn nnnnngaaaa agccgaaggt cacaa 55

<210> SEQ ID NO 105
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 105
cacacaggaa acagctatga ccatgnnnna tgcccccaag aatcctagt 49

<210> SEQ ID NO 106
<211> LENGTH: 55
<212> TYPE: DNA
<213> ORGANISM: Artificial Sequence

```
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 106

cgacgtaaaa cgacggccag tnnnnnnnnn nnnnncatcc gtctactccc acgtt         55


<210> SEQ ID NO 107
<211> LENGTH: 48
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(48)
<223> OTHER INFORMATION: n = A,T,C or G

<400> SEQUENCE: 107

cacacaggaa acagctatga ccatgnnnna tcagctaccg ccaagtcc                 48


<210> SEQ ID NO 108
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 108

cgacgtaaaa cgacggccag tnnnnnnnnn nnnnnttcgt ccctttccag cttta         55


<210> SEQ ID NO 109
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 109

cacacaggaa acagctatga ccatgnnnng gaatccagtg tttcttttaa atacct        56


<210> SEQ ID NO 110
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 110

cgacgtaaaa cgacggccag tnnnnnnnnn nnnnnaccag ccctgtcgtc tctc          54


<210> SEQ ID NO 111
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
```

<223> OTHER INFORMATION: n = A,T,C or G

<400> SEQUENCE: 111
cacacaggaa acagctatga ccatgnnnng ccctgacttt caactctgtc t 51

<210> SEQ ID NO 112
<211> LENGTH: 59
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(59)
<223> OTHER INFORMATION: n = A,T,C or G

<400> SEQUENCE: 112
cgacgtaaaa cgacggccag tnnnnnnnnn nnnnngcctc agattcactt ttatcacct 59

<210> SEQ ID NO 113
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 113
cacacaggaa acagctatga ccatgnnnna ccaggagcca ttgtctttg 49

<210> SEQ ID NO 114
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 114
cgacgtaaaa cgacggccag tnnnnnnnnn nnnnntcacc acattacata cttaccatgc 60

<210> SEQ ID NO 115
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 115
cacacaggaa acagctatga ccatgnnnna aggggatctc ttcctgtatc c 51

<210> SEQ ID NO 116
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 116
cgacgtaaaa cgacggccag tnnnnnnnnn nnnnntctgg atcccagaag gtgag 55

<210> SEQ ID NO 117
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 117
cacacaggaa acagctatga ccatgnnnng gccagtgctg tctctaagg 49

<210> SEQ ID NO 118
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 118
cgacgtaaaa cgacggccag tnnnnnnnnn nnnnngtcca caaaatgatt ctgaattagc 60

<210> SEQ ID NO 119
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 119
cacacaggaa acagctatga ccatgnnnna cgatacacgt ctgcagtcaa c 51

<210> SEQ ID NO 120
<211> LENGTH: 62
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(62)
<223> OTHER INFORMATION: n = A,T,C or G

<400> SEQUENCE: 120
cgacgtaaaa cgacggccag tnnnnnnnnn nnnnnacaga aatattttag aaagggacaa 60
ca 62

<210> SEQ ID NO 121
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 121
cacacaggaa acagctatga ccatgnnnna gaaaataccc cctccatcaa c 51

<210> SEQ ID NO 122
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 122
cgacgtaaaa cgacggccag tnnnnnnnnn nnnnngatcc aatccatttt tgttgtccag 60

<210> SEQ ID NO 123
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 123
cacacaggaa acagctatga ccatgnnnnt ccaaactgac caaactgttc tta 53

<210> SEQ ID NO 124
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 124
cgacgtaaaa cgacggccag tnnnnnnnnn nnnnngaaac ccaaaatctg ttttcca 57

<210> SEQ ID NO 125
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 125
cacacaggaa acagctatga ccatgnnnng accataaccc accacagcta 50

<210> SEQ ID NO 126
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 126
cgacgtaaaa cgacggccag tnnnnnnnnn nnnnnctcct cccagagacc ccagt 55

<210> SEQ ID NO 127
<211> LENGTH: 49
<212> TYPE: DNA

<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 127
cacacaggaa acagctatga ccatgnnnnc atgagcgctg ctcagatag 49

<210> SEQ ID NO 128
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 128
cgacgtaaaa cgacggccag tnnnnnnnnn nnnnncctag gaaggcaggg gagt 54

<210> SEQ ID NO 129
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 129
cacacaggaa acagctatga ccatgnnnnt gcatgttgct tttgtaccg 49

<210> SEQ ID NO 130
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 130
cgacgtaaaa cgacggccag tnnnnnnnnn nnnnnaccac ccgcacgtct gtag 54

<210> SEQ ID NO 131
<211> LENGTH: 48
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(48)
<223> OTHER INFORMATION: n = A,T,C or G

<400> SEQUENCE: 131
cacacaggaa acagctatga ccatgnnnna gccagtgctt gttgcttg 48

<210> SEQ ID NO 132
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 132
cgacgtaaaa cgacggccag tnnnnnnnnn nnnnncacac tgacgtgcct ctcc 54

<210> SEQ ID NO 133
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 133
cacacaggaa acagctatga ccatgnnnnt tatctcccct ccccgtatc 49

<210> SEQ ID NO 134
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 134
cgacgtaaaa cgacggccag tnnnnnnnnn nnnnngattg tcagtgcgct tttcc 55

<210> SEQ ID NO 135
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 135
cacacaggaa acagctatga ccatgnnnng ctaaggatgg gggttgcta 49

<210> SEQ ID NO 136
<211> LENGTH: 61
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(61)
<223> OTHER INFORMATION: n = A,T,C or G

<400> SEQUENCE: 136
cgacgtaaaa cgacggccag tnnnnnnnnn nnnnntgact ttaccttatc aatgtctcga 60
a 61

<210> SEQ ID NO 137
<211> LENGTH: 48
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(48)
<223> OTHER INFORMATION: n = A,T,C or G

<400> SEQUENCE: 137
cacacaggaa acagctatga ccatgnnnng ctcgccccct taatctct 48

<210> SEQ ID NO 138
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 138
cgacgtaaaa cgacggccag tnnnnnnnnn nnnnnggtac ttccggaacc tgtgc 55

<210> SEQ ID NO 139
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 139
cacacaggaa acagctatga ccatgnnnnc cgagtcctag ggagaggag 49

<210> SEQ ID NO 140
<211> LENGTH: 58
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(58)
<223> OTHER INFORMATION: n = A,T,C or G

<400> SEQUENCE: 140
cgacgtaaaa cgacggccag tnnnnnnnnn nnnnnttgtt aatggtggct ttttgttt 58

<210> SEQ ID NO 141
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 141
cacacaggaa acagctatga ccatgnnnna aatgatctaa caatgctctt ggac 54

<210> SEQ ID NO 142
<211> LENGTH: 58
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(58)
<223> OTHER INFORMATION: n = A,T,C or G

<400> SEQUENCE: 142
cgacgtaaaa cgacggccag tnnnnnnnnn nnnnncatgg aaggatgaga atttcaag 58

<210> SEQ ID NO 143
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 143
cacacaggaa acagctatga ccatgnnnnt ggctacgacc cagttacca 49

<210> SEQ ID NO 144
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 144
cgacgtaaaa cgacggccag tnnnnnnnnn nnnnnaaacc gtagctgccc tggta 55

<210> SEQ ID NO 145
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 145
cacacaggaa acagctatga ccatgnnnnt gactgctctt ttcacccatc 50

<210> SEQ ID NO 146
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 146
cgacgtaaaa cgacggccag tnnnnnnnnn nnnnntcatc ttgggcctgt gttatc 56

<210> SEQ ID NO 147
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 147
cacacaggaa acagctatga ccatgnnnng atgagaggtg gatgggtagt agt 53

<210> SEQ ID NO 148
<211> LENGTH: 56

```
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 148

cgacgtaaaa cgacggccag tnnnnnnnnn nnnnnttcag ggcatgaact acttgg        56


<210> SEQ ID NO 149
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 149

cacacaggaa acagctatga ccatgnnnna tcctccccctg catgtgtta                49


<210> SEQ ID NO 150
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 150

cgacgtaaaa cgacggccag tnnnnnnnnn nnnnntccct cattgcactg tactcc        56


<210> SEQ ID NO 151
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 151

cacacaggaa acagctatga ccatgnnnng gtgcttagtg gccatttgt                49


<210> SEQ ID NO 152
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 152

cgacgtaaaa cgacggccag tnnnnnnnnn nnnnntggtc tctcatggca ctgtact       57


<210> SEQ ID NO 153
<211> LENGTH: 52
<212> TYPE: DNA
<213> ORGANISM: Artificial Sequence
<220> FEATURE:
<223> OTHER INFORMATION: Primers
```

<221> NAME/KEY: misc_feature
<222> LOCATION: (1)...(52)
<223> OTHER INFORMATION: n = A,T,C or G

<400> SEQUENCE: 153
cacacaggaa acagctatga ccatgnnnna ttagcaattt gagggacaaa cc 52

<210> SEQ ID NO 154
<211> LENGTH: 62
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(62)
<223> OTHER INFORMATION: n = A,T,C or G

<400> SEQUENCE: 154
cgacgtaaaa cgacggccag tnnnnnnnnn nnnnntgtat ctcactcgat aatctggatg 60
ac 62

<210> SEQ ID NO 155
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 155
cacacaggaa acagctatga ccatgnnnnt gtcacattat aaagattcag gcaat 55

<210> SEQ ID NO 156
<211> LENGTH: 59
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(59)
<223> OTHER INFORMATION: n = A,T,C or G

<400> SEQUENCE: 156
cgacgtaaaa cgacggccag tnnnnnnnnn nnnnnagttt gacagttaaa ggcatttcc 59

<210> SEQ ID NO 157
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 157
cacacaggaa acagctatga ccatgnnnnt gtccttattt tggatatttc tccc 54

<210> SEQ ID NO 158
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)

<223> OTHER INFORMATION: n = A,T,C or G

<400> SEQUENCE: 158
cgacgtaaaa cgacggccag tnnnnnnnnn nnnnngaaga cccaggtcca gatga 55

<210> SEQ ID NO 159
<211> LENGTH: 48
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(48)
<223> OTHER INFORMATION: n = A,T,C or G

<400> SEQUENCE: 159
cacacaggaa acagctatga ccatgnnnna gaaatgcagg gggatacg 48

<210> SEQ ID NO 160
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 160
cgacgtaaaa cgacggccag tnnnnnnnnn nnnnngaggc ataactgcac ccttg 55

<210> SEQ ID NO 161
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 161
cacacaggaa acagctatga ccatgnnnng ggagtagatg gagcctggt 49

<210> SEQ ID NO 162
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 162
cgacgtaaaa cgacggccag tnnnnnnnnn nnnnntgctg gatttggttc taggg 55

<210> SEQ ID NO 163
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 163

```
cacacaggaa acagctatga ccatgnnnnt gccacttgca aagtttcttc              50


<210> SEQ ID NO 164
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 164

cgacgtaaaa cgacggccag tnnnnnnnnn nnnnnggaag aacctggacc ctctg         55


<210> SEQ ID NO 165
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 165

cacacaggaa acagctatga ccatgnnnnt tttgagagtc gttcgattgc              50


<210> SEQ ID NO 166
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 166

cgacgtaaaa cgacggccag tnnnnnnnnn nnnnntgcaa cctgttttgt gatgg         55


<210> SEQ ID NO 167
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 167

cacacaggaa acagctatga ccatgnnnna ggaaaatgac aatgggaatg a            51


<210> SEQ ID NO 168
<211> LENGTH: 59
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(59)
<223> OTHER INFORMATION: n = A,T,C or G

<400> SEQUENCE: 168

cgacgtaaaa cgacggccag tnnnnnnnnn nnnnntgatt catcaggaga gcatttaag     59


<210> SEQ ID NO 169
```

<211> LENGTH: 52
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(52)
<223> OTHER INFORMATION: n = A,T,C or G

<400> SEQUENCE: 169
cacacaggaa acagctatga ccatgnnnnt tgtttttctg tttctccctc tg 52

<210> SEQ ID NO 170
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 170
cgacgtaaaa cgacggccag tnnnnnnnnn nnnnngatgg tatccatgtg gtgagtg 57

<210> SEQ ID NO 171
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 171
cacacaggaa acagctatga ccatgnnnnt ttgtgatgct aaggctccat 50

<210> SEQ ID NO 172
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 172
cgacgtaaaa cgacggccag tnnnnnnnnn nnnnnactgc cttccgggtc act 53

<210> SEQ ID NO 173
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 173
cacacaggaa acagctatga ccatgnnnna gcccaaccct tgtccttac 49

<210> SEQ ID NO 174
<211> LENGTH: 54
<212> TYPE: DNA
<213> ORGANISM: Artificial Sequence
<220> FEATURE:

<223> OTHER INFORMATION: Primers
<221> NAME/KEY: misc_feature
<222> LOCATION: (1)...(54)
<223> OTHER INFORMATION: n = A,T,C or G

<400> SEQUENCE: 174
cgacgtaaaa cgacggccag tnnnnnnnnn nnnnngaggc tgtcagtggg gaac 54

<210> SEQ ID NO 175
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 175
cacacaggaa acagctatga ccatgnnnna acatatttgc atggggtgtg 50

<210> SEQ ID NO 176
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 176
cgacgtaaaa cgacggccag tnnnnnnnnn nnnnnccact gcatggttca ctctg 55

<210> SEQ ID NO 177
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 177
cacacaggaa acagctatga ccatgnnnna tcctgtgagc gaagttcca 49

<210> SEQ ID NO 178
<211> LENGTH: 57
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(57)
<223> OTHER INFORMATION: n = A,T,C or G

<400> SEQUENCE: 178
cgacgtaaaa cgacggccag tnnnnnnnnn nnnnntgcct ctttctcttg gttttca 57

<210> SEQ ID NO 179
<211> LENGTH: 51
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(51)
<223> OTHER INFORMATION: n = A,T,C or G

<400> SEQUENCE: 179
cacacaggaa acagctatga ccatgnnnng gacctaagca agctgcagta a 51

<210> SEQ ID NO 180
<211> LENGTH: 60
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(60)
<223> OTHER INFORMATION: n = A,T,C or G

<400> SEQUENCE: 180
cgacgtaaaa cgacggccag tnnnnnnnnn nnnnnacacc caatgaagaa tgtaattgat 60

<210> SEQ ID NO 181
<211> LENGTH: 54
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(54)
<223> OTHER INFORMATION: n = A,T,C or G

<400> SEQUENCE: 181
cacacaggaa acagctatga ccatgnnnng gttgtgtgta gatgtgagtt ttcc 54

<210> SEQ ID NO 182
<211> LENGTH: 59
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(59)
<223> OTHER INFORMATION: n = A,T,C or G

<400> SEQUENCE: 182
cgacgtaaaa cgacggccag tnnnnnnnnn nnnnnttctg ttacattgtg cagagttca 59

<210> SEQ ID NO 183
<211> LENGTH: 50
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(50)
<223> OTHER INFORMATION: n = A,T,C or G

<400> SEQUENCE: 183
cacacaggaa acagctatga ccatgnnnnt ggttttgagc agagagatgg 50

<210> SEQ ID NO 184
<211> LENGTH: 55
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 184
cgacgtaaaa cgacggccag tnnnnnnnnn nnnnnggaag aagtcccaac catga 55

<210> SEQ ID NO 185
<211> LENGTH: 53
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(53)
<223> OTHER INFORMATION: n = A,T,C or G

<400> SEQUENCE: 185
cacacaggaa acagctatga ccatgnnnnt cacttttcct ttctacccaa aag 53

<210> SEQ ID NO 186
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 186
cgacgtaaaa cgacggccag tnnnnnnnnn nnnnngaatc tgcattccca gagaca 56

<210> SEQ ID NO 187
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 187
cacacaggaa acagctatga ccatgnnnnc ctgtttccca tcctcttcc 49

<210> SEQ ID NO 188
<211> LENGTH: 56
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(56)
<223> OTHER INFORMATION: n = A,T,C or G

<400> SEQUENCE: 188
cgacgtaaaa cgacggccag tnnnnnnnnn nnnnngacac aaaacaggct caggac 56

<210> SEQ ID NO 189
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 189
cacacaggaa acagctatga ccatgnnnna gaaaccaaag ccaaaagca 49

<210> SEQ ID NO 190
<211> LENGTH: 55

-continued

```
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(55)
<223> OTHER INFORMATION: n = A,T,C or G

<400> SEQUENCE: 190

cgacgtaaaa cgacggccag tnnnnnnnnn nnnnnccatg ggactgactt tctgc         55


<210> SEQ ID NO 191
<211> LENGTH: 49
<212> TYPE: DNA
<213> ORGANISM: Artificial Sequence
<220> FEATURE:
<223> OTHER INFORMATION: Primers
<221> NAME/KEY: misc_feature
<222> LOCATION: (1)...(49)
<223> OTHER INFORMATION: n = A,T,C or G

<400> SEQUENCE: 191

cacacaggaa acagctatga ccatgnnnnt catctggacc tgggtcttc                49
```